US008642772B2

(12) United States Patent
Chung et al.

(10) Patent No.: US 8,642,772 B2
(45) Date of Patent: Feb. 4, 2014

(54) PIPERIDINE COMPOUNDS, PHARMACEUTICAL COMPOSITION COMPRISING THE SAME AND ITS USE

(75) Inventors: Coo-Min Chung, Daejeon (KR); Hyung-Jin Jun, Daejeon (KR); Jin-Sung Kim, Daejeon (KR); Hui-Ho Kim, Daejeon (KR); Hye-Kyung Min, Daejeon (KR); Yong-Gil Kim, Daejeon (KR); Jong-Gil Choi, Daejeon (KR); Hongwook Kim, Montville, NJ (US)

(73) Assignee: SK Biopharmaceuticals Co., Ltd., Seoul (KR)

( * ) Notice: Subject to any disclaimer, the term of this patent is extended or adjusted under 35 U.S.C. 154(b) by 596 days.

(21) Appl. No.: 12/576,494

(22) Filed: Oct. 9, 2009

(65) Prior Publication Data

US 2010/0093801 A1    Apr. 15, 2010

Related U.S. Application Data

(60) Provisional application No. 61/105,070, filed on Oct. 14, 2008.

(51) Int. Cl.
*C07D 211/22*    (2006.01)
*A61K 31/445*    (2006.01)

(52) U.S. Cl.
USPC ............................ 546/234; 546/200; 514/331

(58) Field of Classification Search
USPC .................................. 546/200, 234; 514/331
See application file for complete search history.

(56) References Cited

U.S. PATENT DOCUMENTS

| 5,705,640 | A | 1/1998 | Choi et al. |
| 5,756,817 | A | 5/1998 | Choi et al. |
| 5,955,499 | A | 9/1999 | Choi et al. |
| 6,002,009 | A | 12/1999 | Cereda et al. |
| 6,140,532 | A | 10/2000 | Choi et al. |

FOREIGN PATENT DOCUMENTS

| WO | 99/02494 | 1/1999 |
| WO | 99/55674 | 11/1999 |
| WO | 02/50071 | 6/2002 |
| WO | 02/080928 | 10/2002 |
| WO | 02/100352 | 12/2002 |
| WO | 2004/026868 | 4/2004 |
| WO | 2004/094418 | 11/2004 |
| WO | 2005/021539 | 3/2005 |
| WO | 2005/092882 | 10/2005 |
| WO | 2006090279 | 8/2006 |
| WO | 2006/106425 | 10/2006 |
| WO | 2007149929 | 12/2007 |

OTHER PUBLICATIONS

Sonda et al., Bioorganic & Medicinal Chemistry 13 (2005) 3295-3308.*

PCT/KR2009/005863 International Search Report and Written Opinion dated May 28, 2010 (9 pages).
Nisell, Magnus, et al., "Nicotine Dependence, Midbrain Dopamine Systems and Psychiatric Disorders", Pharmacology & Toxicology, vol. 76, pp. 157-162, 1995.
Pontieri, Francesco, E. et al., "Effects of Nicotine on the Nucleus Accumbens and Similarity to Those of Addictive Drugs", Letters to Nature, vol. 382, pp. 255-257, Jul. 18, 1996.
Damsma, Geert, et al., "Lack of Tolerance to Nicotine-Induced Dopamine Release in the Nucleus Accumbens", European Journal of Pharmacology, vol. 168, pp. 363-368, 1989.
Di Chiara, Gaetano, et al., "Drugs Abused by Humans Preferentially Increase Synaptic Dopamine Concentrations in the Mesolimbic System of Freely Moving Rats", Proc. Natl. Acad. Sci. USA, vol. 85, pp. 5274-5278, Jul. 1988.
Imperato, Assunta, et al., "Nicotine preferentially Stimulates Dopamine Release in the Limbic System of Freely Moving Rats", European Journal of Pharmacology, vol. 132, pp. 337-338, 1986.
Nissell, Magnus, et al., "Infusion of Nicotine in the Ventral Tegmental Area or the Nucleus Accumbens of the Rat Differentially Affects Accumbal Dopamine Release", Pharmacology & Toxicology, vol. 75, pp. 348-352, 1994.
Nissell, Magnus, et al., "Systemic Nicotine-Induced Dopamine Release in the Rat Nucleus Accumbens Is Regulated by Nicotinic Receptors in the Ventral Tegmental Area", Synapse, pp. 36-44, 1994.
Henningfield, Jack, E. Ph.D., "Nicotine Medications for Smoking Cessation", The New England Journal of Medicine, vol. 333, No. 18, pp. 1196-1203, Nov. 2, 1995.
Hurt, Richard, D., et al, "A Comparison of Sustained-Release Bupropion and Placebo for Smoking Cessation", The New England Journal of Medicine, vol. 337, No. 17, pp. 1195-1202, Oct. 23, 1997.
Allen, R.P., PhD, et al., "MRI Measurement of Brain Iron in Patients with Restless Legs Syndrome", Neurology, vol. 56, pp. 263-265, Jan. 2001.
Miklowitz, David, J., et al., "The Psychopathology and Treatment of Bipolar Disorder", Annu. Rev. Clin. Psychol., vol. 2, 2006.
Miller, Christopher, J., et al., "Assessment Tools for Adult Bipolar Disorder", Clin Psychol. (New York), vol. 16, No. 2, pp. 188-201, Jun. 1, 2009.
Minto, Charles, F., et al., "Pharmacokinetics and Pharmacodynamics of Nandrolone Esters in Oil Vehicle: Effects of Ester, Injection Site and Injection Volume", The Journal of Pharmacology and Experimental Therapeutics, vol. 281, No. 1, pp. 93-102, 1997.
Ostro, Marc, J., et al., "Use of Liposomes as Injectable-Drug Delivery Systems", American Journal of Hospital Pharmacy, vol. 46, pp. 1576-1587, Aug. 1989.
Rao, K, "Recent Developments of Collagen-Based Materials for Medical Applications and Drug Delivery Systems", J. Biomater. Sci. Polymer Edn., vol. 7, No. 7, pp. 623-645, 1995.
Rapoport, Stanley, I., et al., "Bipolar Disorder and Mechanisms of Action of Mood Stabilizers", Brain Research Reviews, vol. 61, pp. 185-209, 2009.

(Continued)

*Primary Examiner* — Yong Chu
*Assistant Examiner* — Sonya Wright
(74) *Attorney, Agent, or Firm* — Harness, Dickey & Pierce, P.L.C.

(57) ABSTRACT

Piperidine compounds and pharmaceutically useful salts thereof, a pharmaceutical composition including an effective amount of the racemic or enantiomerically enriched piperidine compounds to treat gastrointestinal diseases, and a method of treating gastrointestinal diseases in a mammal are provided.

20 Claims, No Drawings

(56) References Cited

OTHER PUBLICATIONS

Rohatagi, Shashank, PhD, et al., "Pharmacokinetic and Pharmacodynamic Evaluation of Triamcinolone Acetonide After Intravenous, Oral, and Inhaled Administration", J. Clin. Pharmacol., vol. 35, pp. 1187-1193, 1995.

Tjwa, Martin, K. T., MD, "Budesonide Inhaled Via Turbuhaler: A More Effective Treatment for Asthma than Beclomethasone Dipropionate Via Rotahaler", Annals of Allergy, Asthma, & Immunology, vol. 75, pp. 107-111, 1995.

Vieta, Eduard, et al., "Evolving Trends in the Long-Term Treatment of Bipolar Disorder", The World Journal of Biological Psychiatry, vol. 8, No. 1, pp. 4-11, 2007.

Al-Muhammed, J., et al., "In-Vivo Studies on Dexamethasone Sodium Phosphate Liposomes", J. Microencapsulation, vol. 13, No. 3, pp. 293-306, 1996.

Azorin, Jean-Michel, et al., "An Update on the Treatment of Bipolar Depression", Expert Opin. Pharmacother., vol. 10, No. 2, pp. 161-172, 2009.

Chengappa, KNR, et al., "Barriers to the Effective Management of Bipolar Disorder: A Survey of Psychiatrists Based in the UK and USA", Bipolar Disorders, vol. 7, suppl.1, pp. 38-42, 2005.

Chonn, Arcadio, et al., "Recent Advances in Liposomal Drug-Delivery Systems", Current Opinion in Biotechnology, vol. 6, pp. 698-708, 1995.

Cousins, David, A., et al., "The Role of Dopamine in Bipolar Disorder", Bipolar Disorders, vol. 11, pp. 787-806, 2009.

Cuellar, Amy, K., et al., "Distinctions Between Bipolar and Unipolar Depression", Clin. Psychol. Rev., vol. 25, No. 3, pp. 307-339, May 2005.

Eyles, J.E., et al., "Oral Delivery and Fate of Poly(lactic acid) Microsphere-encapsulated Interferon in Rats", J. Pharm. Pharmacol, vol. 49, pp. 669-674, 1997.

Frye, Mark, A., et al., "Unmet Needs in Bipolar Depression", Depression and Anxiety, vol. 19, pp. 1999-208, 2004.

Gao, Zhi-Hui, et al., "Controlled Release of a Contraceptive Steroid from Biodegradable and Injectable Gel Formulations: In Vitro Evaluation", Pharmaceutical Research, vol. 12, No. 6, pp. 857-863, 1995.

Harel, Eiran Vadim, MD, et al., "Effectiveness and Safety of Adjunctive Antidepressants in the Treatment of Bipolar Depression: A Review", Isr J Psychiatry Relat Sci, vol. 45, No. 2, pp. 121-128, 2008.

Kessler, Ronald, C., et al., "Lifetime Prevalence and Age-of-Onset Distributions of DSM-IV Disorders in the National Comorbidity Survey Replication", Arch Gen Psychiatry, vol. 62, pp. 593-602 & 768, Jun. 2005.

Kessler, Ronald, C., et al., "Prevalence, Severity and Comorbidity of Twelve-month DSM-IV Disorders in the National Comorbidity Survey Replication (NCS-R)", Arch Gen Psychiatry, vol. 62, No. 6, pp. 617-627, Jun. 2005.

Bayard, Max, MD, et al., "Restless Legs Syndrome", American Family Physician, vol. 78, No. 2, pp. 235-240, Jul. 15, 2008.

Ferini-Strambi, Luigi, "Treatment Options for Restless Legs Syndrome", Expert Opin. Pharmacother., vol. 10, No. 4, pp. 545-554, 2009.

Fulda, Stephany, et al., "Dopamine Agonists for the Treatment of Restless Legs Syndrome", Expert Opin. Pharmacother., vol. 6, No. 15, pp. 2655-2666, 2005.

Garcia-Borreguero, Diego, MD, et al., "Circadian Variation in Neuroendocrine Response to L-dopa in Patients with Restless Legs Syndrome", Sleep, vol. 27, No. 4, pp. 669-673, 2004.

Hornyak, Magdolna, "Depressive Disorders in Restless Legs Syndrome", CNS Drugs, vol. 24, No. 2, pp. 89-98, 2010.

Kim, Sung-Wan, MD, et al., "Bupropion May Improve Restless Legs Syndrome", Clin Neuropharmacol, vol. 28, No. 6, pp. 298-301, Nov.-Dec. 2005.

Ondo, William, G., MD, "Restless Legs Syndrome", Neurol Clin, vol. 27, pp. 779-799, 2009.

Stiasny-Kolster, K., et al., "Static Mechanical Hyperalgesia Without Dynamic Tactile Allodynia in Patients with Restless Legs Syndrome", Brain, vol. 127, No. 4, pp. 773-782, 2004.

Search Report from the European Patent Office for Application No. 09820735.0 dated Mar. 21, 2012 (4 pages).

* cited by examiner

PIPERIDINE COMPOUNDS, PHARMACEUTICAL COMPOSITION COMPRISING THE SAME AND ITS USE

This application claims the benefit of U.S. Provisional Application No. 61/105,070, filed Oct. 14, 2008, which is incorporated by reference herein in its entirety for any purpose.

TECHNICAL FIELD

The present invention relates, in general, to a piperidine compound and pharmaceutically useful salts thereof, a pharmaceutical composition including an effective amount of racemic or enantiomerically enriched piperidine compounds to treat gastrointestinal diseases, and a method of treating gastrointestinal diseases in a mammal. More particularly, the present invention relates to racemic or enantiomerically enriched O-carbamoyl and hydroxyl piperidine compounds and pharmaceutically useful salts thereof, that are useful to treat irritable bowel syndrome (IBS), gastric motility disorder, and visceral pain.

BACKGROUND

Many reports have disclosed that piperidine compounds are effectively used for controlling various gastrointestinal diseases, especially for irritable bowel syndrome and gastric motility disorders.

For example, cis-4-amino-5-chloro-N-[1-[3-(4-fluorophenoxy)-propyl]-3-methoxy-4-piperidinyl]-2-methoxybenzamide (general name: Cisapride) has been widely used in the clinical field as a gastrointestinal motility enhancer or as a gastrointestinal prokinetic agent, and other piperidine compounds have been disclosed in many patents (WO2005/092882, WO1999/055674, WO2005/021539, WO04/026868, WO04/094418, WO99/02494) as therapeutic medicines for managing gastrointestinal diseases.

Active research and development efforts have continued to be directed to the application of piperidine compounds for the treatment of gastrointestinal diseases.

SUMMARY

Certain embodiments provide a piperidine compound and/or a pharmaceutically-acceptable salt thereof, a pharmaceutical composition including an effective amount of a piperidine compound and/or a pharmaceutically-acceptable salt thereof for treating a gastrointestinal disease, and a method of treating diseases in a mammal, such as irritable bowel syndrome (IBS), gastric motility disorder, and/or visceral pain.

Certain embodiments provide a method of treating disorders in a mammal by administering an effective amount of racemic or enantiomerically enriched piperidine compound represented by the below structural formula (I), in particular, the compounds represented by the below structural formulae (IV) and (V), and a pharmaceutically acceptable carrier to a mammal in need of irritable bowel syndrome (IBS) or gastric motility disorder therapy.

DESCRIPTION

A more complete appreciation of the invention, and many of the attendant advantages thereof, will be readily apparent as the same becomes better understood by reference to the following detailed description.

In an embodiment, a piperidine compound, represented by the following structural formula (I), and pharmaceutically acceptable salts thereof are provided,

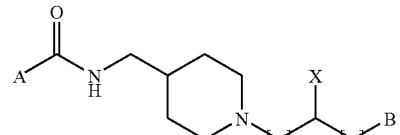

(I)

wherein:

m is an integer of 1 or 2;

n is an integer of 0 to 2, preferably 0;

A is selected from the group consisting of a phenyl group and a benzimidazole group, wherein the phenyl group may be substituted with one or more identical or different groups independently selected from the group consisting of hydrogen, a C1-C6 linear or branched alkyl group, a C1-C6 linear or branched alkoxy group, an amino group, and a halogen, and the benzimidazole group may be substituted with one or more identical or different groups independently selected from the group consisting of hydrogen, a C1-C6 linear or branched alkyl group, a C1-C6 linear or branched alkoxy group, a C3-C7 cyclic alkyl group, an amino group, a halogen, and an oxo group;

X is a hydroxy or $OCONR_1R_2$ wherein $R_1$ and $R_2$ may be the same or different and independently selected from the group consisting of hydrogen, a C1-C6 linear or branched alkyl group, a benzyl group, and a 5- to 7-membered cyclic or heterocyclic compound that may be substituted with one or more identical or different groups independently selected from the group consisting of a C1 to C6 alkyl, or $R_1$ and $R_2$ may form a 5- to 7-membered heterocyclic ring together with a nitrogen atom to which they are attached; and B is selected from the group consisting of a phenyl group, a phenoxy group, a thienyl group, and a naphthyl group, wherein the phenyl group, phenoxy group, thienyl group, or naphthyl group may be substituted with one or more identical or different groups independently selected from the group consisting of hydrogen, halogen, nitro, cyano, methanesulfonyl, trifluoromethyl, trifluoromethoxy, difluoromethoxy, phenyl, a C1-C6 linear or branched alkyl group, and a C1-C6 linear or branched alkoxy group.

In the definition of the substituents, the alkyl group may be selected from the group consisting of a methyl, an ethyl, a linear or branched propyl, a linear or branched butyl, a cyclopropyl, a cyclobutyl, a cyclopentyl, a cyclohexyl, and a benzyl. The halogen is selected from fluoro, chloro, bromo, and iodo atoms.

In an embodiment, substituent A in structural formula (I) may be a phenyl group that may be substituted with one or more identical or different groups independently selected from the group consisting of hydrogen, a halogen, an amino group, a C1-C6 linear or branched alkyl group, or a C1-C6 linear and branched alkoxy group.

Substituent A may be represented by structural formula (II):

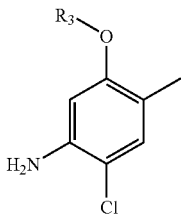

(II)

wherein R3 is a substituted or unsubstituted C1 to C6 linear or branched alkyl.

When substituent A in structural formula (I) has structural formula (II), the piperidine compound is represented by the following structural formula (IV):

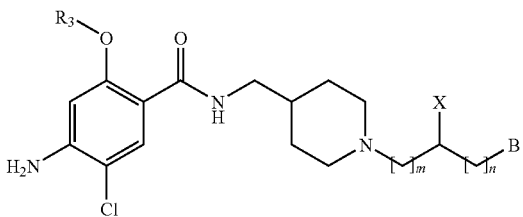

(IV)

wherein m, n, X, B, and R3 are defined as above.

The examples of the compound having the chemical formula (IV) may include of 4-amino-5-chloro-N-[[1-(2-hydroxy-2-phenylethyl)piperidin-4-yl]methyl]-2-methoxybenzamide;
4-amino-5-chloro-N-[[1-[2-(4-fluorophenyl)-2-hydroxyethyl]piperidin-4-yl]methyl]-2-methoxybenzamide:hydrochloride;
4-amino-5-chloro-N-[[1-[2-hydroxy-2-(4-methylphenyl)ethyl]piperidin-4-yl]methyl]-2-methoxybenzamide:hydrochloride;
4-amino-5-chloro-N-[[1-[2-hydroxy-2-(4-methoxyphenyl)ethyl]piperidin-4-yl]methyl]-2-methoxybenzamide:hydrochloride;
4-amino-5-chloro-N-[[1-[2-(4-chlorophenyl)-2-hydroxyethyl]piperidin-4-yl]methyl]-2-methoxybenzamide:hydrochloride;
4-amino-5-chloro-N-[[1-[2-(3,4-dichlorophenyl)-2-hydroxyethyl]piperidin-4-yl]methyl]-2-methoxybenzamide:hydrochloride;
4-amino-5-chloro-N-[[1-[2-hydroxy-2-[4-(trifluoromethyl)phenyl]ethyl]piperidin-4-yl]methyl]-2-methoxybenzamide:hydrochloride;
4-amino-5-chloro-N-[[1-[2-(3,4-difluorophenyl)-2-hydroxyethyl]piperidin-4-yl]methyl]-2-methoxybenzamide:hydrochloride;
[2-[4-[[(4-amino-5-chloro-2-methoxybenzoyl)amino]methyl]piperidin-1-yl]-1-phenylethyl]carbamate:hydrochloride;
[2-[4-[[(4-amino-5-chloro-2-methoxybenzoyl)amino]methyl]piperidin-1-yl]-1-(4-fluorophenyl)ethyl]carbamate:hydrochloride;
[2-[4-[[(4-amino-5-chloro-2-methoxybenzoyl)amino]methyl]piperidin-1-yl]-1-(3,4-dichlorophenyl)ethyl]carbamate:hydrochloride;
[2-[4-[[(4-amino-5-chloro-2-methoxybenzoyl)amino]methyl]piperidin-1-yl]-1-(3,4-difluorophenyl)ethyl]carbamate:hydrochloride;
[2-[4-[[(4-amino-5-chloro-2-methoxybenzoyl)amino]methyl]piperidin-1-yl]-1-[4-(trifluoromethyl)phenyl]ethyl]carbamate:hydrochloride;
4-amino-5-chloro-N-[[1-(3-hydroxy-3-phenylpropyl)piperidin-4-yl]methyl]-2-methoxybenzamide:hydrochloride;
4-amino-5-chloro-N-[[1-[3-(4-fluorophenyl)-3-hydroxypropyl]piperidin-4-yl]methyl]-2-methoxybenzamide:hydrochloride;
4-amino-5-chloro-N-[[1-[3-(3,4-dichlorophenyl)-3-hydroxypropyl]piperidin-4-yl]methyl]-2-methoxybenzamide:hydrochloride;
4-amino-5-chloro-N-[[1-(3-hydroxy-3-thiophen-2-ylpropyl)piperidin-4-yl]methyl]-2-methoxybenzamide:hydrochloride;
4-amino-5-chloro-N-[[1-[4-(4-fluorophenyl)-3-hydroxybutyl]piperidin-4-yl]methyl]-2-methoxybenzamide:hydrochloride;
4-amino-5-chloro-N-[[1-[5-(4-fluorophenyl)-3-hydroxypentyl]piperidin-4-yl]methyl]-2-methoxybenzamide:hydrochloride;
[3-[4-[[(4-amino-5-chloro-2-methoxybenzoyl)amino]methyl]piperidin-1-yl]-1-(4-chlorophenyl)propyl]carbamate:hydrochloride;
[4-[4-[[(4-amino-5-chloro-2-methoxybenzoyl)amino]methyl]piperidin-1-yl]-1-(4-fluorophenyl)butan-2-yl]carbamate:hydrochloride;
[1-[4-[[(4-amino-5-chloro-2-methoxybenzoyl)amino]methyl]piperidin-1-yl]-5-(4-fluorophenyl)pentan-3-yl]carbamate:hydrochloride;
4-amino-5-chloro-N-[[1-(2-hydroxy-3-phenoxypropyl)piperidin-4-yl]methyl]-2-methoxybenzamide:hydrochloride;
4-amino-5-chloro-N-[[1-[3-(4-chlorophenoxy)-2-hydroxypropyl]piperidin-4-yl]methyl]-2-methoxybenzamide:hydrochloride;
4-amino-5-chloro-N-[[1-[2-hydroxy-3-[4-(trifluoromethyl)phenoxy]propyl]piperidin-4-yl]methyl]-2-methoxybenzamide:hydrochloride;
[1-[4-[[(4-amino-5-chloro-2-methoxybenzoyl)amino]methyl]piperidin-1-yl]-3-phenoxypropan-2-yl]carbamate:hydrochloride;
[1-[4-[[(4-amino-5-chloro-2-methoxybenzoyl)amino]methyl]piperidin-1-yl]-3-(4-fluorophenoxy)propan-2-yl]3,5-dimethylpiperidine-1-carboxylate:hydrochloride
[1-[4-[[(4-amino-5-chloro-2-methoxybenzoyl)amino]methyl]piperidin-1-yl]-3-(4-methoxyphenoxy)propan-2-yl]carbamate:hydrochloride;
[1-[4-[[(4-amino-5-chloro-2-methoxybenzoyl)amino]methyl]piperidin-1-yl]-3-(2,3-dichlorophenoxy)propan-2-yl]azepane-1-carboxylate:hydrochloride;
4-amino-5-chloro-N-[[1-[(2S)-2-hydroxy-2-phenylethyl]piperidin-4-yl]methyl]-2-methoxybenzamide;
4-amino-5-chloro-N-[[1-[(2R)-2-hydroxy-2-phenylethyl]piperidin-4-yl]methyl]-2-methoxybenzamide;
4-amino-5-chloro-N-[[1-[3-(4-chlorophenyl)-3-hydroxypropyl]piperidin-4-yl]methyl]-2-methoxybenzamide;
[3-[4-[[(4-amino-5-chloro-2-methoxybenzoyl)amino]methyl]piperidin-1-yl]-1-(4-fluorophenyl)propyl]carbamate;

(R)-[3-[4-[[(4-amino-5-chloro-2-methoxybenzoyl)amino]methyl]piperidin-1-yl]-1-(4-fluorophenyl)propyl]carbamate;

(S)-[3-[4-[[(4-amino-5-chloro-2-methoxybenzoyl)amino]methyl]piperidin-1-yl]-1-(4-fluorophenyl)propyl]carbamate;

4-amino-5-chloro-N-[[1-[2-hydroxy-3-(4-methoxyphenoxy)propyl]piperidin-4-yl]methyl]-2-methoxybenzamide;

[1-[4-[[(4-amino-5-chloro-2-methoxybenzoyl)amino]methyl]piperidin-1-yl]-3-phenoxypropan-2-yl]piperidine-1-carboxylate; and 4-amino-5-chloro-N-[[1-[3-(2,5-dichlorophenoxy)-2-hydroxypropyl]piperidin-4-yl]methyl]-2-methoxybenzamide.

In another embodiment, substituent A may be a benzimidazole group that may be substituted with one or more identical or different groups independently selected from the group consisting of hydrogen, a C1-C6 linear or branched alkyl group, a C1-C6 linear or branched alkoxy group, a C3-C7 cyclic alkyl group, an amino group, a halogen, and an oxo group.

Substituent A in structural formula (I) is represented by structural formula (III):

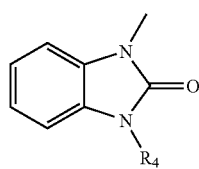

(III)

wherein R4 is C1-C6 linear or branched alkyl group, or a C3-C7 cyclic alkyl that may be substituted or unsubstituted.

When substituent A in structural formula (I) has structural formula (III), the piperidine compound is represented by the following structural formula (V):

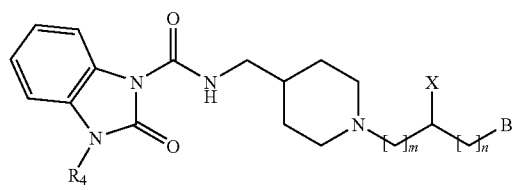

(V)

The examples of the compound having the chemical formula (V) may include [1-(2-methylphenoxy)-3-[4-[[(2-oxo-3-propan-2-ylbenzimidazole-1-carbonyl)amino]methyl]piperidin-1-yl]propan-2-yl]carbamate;

N-[[1-[2-hydroxy-3-(4-nitrophenoxy)propyl]piperidin-4-yl]methyl]-2-oxo-3-propan-2-ylbenzimidazole-1-carboxamide:hydrochloride;

N-[[1-[2-hydroxy-3-(4-methoxyphenoxy)propyl]piperidin-4-yl]methyl]-2-oxo-3-propan-2-ylbenzimidazole-1-carboxamide:hydrochloride;

N-[[1-[3-(4-fluorophenoxy)-2-hydroxypropyl]piperidin-4-yl]methyl]-3-methyl-2-oxobenzimidazole-1-carboxamide:hydrochloride;

3-ethyl-N-[[1-[2-hydroxy-3-(4-methoxyphenoxy)propyl]piperidin-4-yl]methyl]-2-oxobenzimidazole-1-carboxamide:hydrochloride;

[1-[4-[[(2-oxo-3-propan-2-ylbenzimidazole-1-carbonyl)amino]methyl]piperidin-1-yl]-3-phenoxypropan-2-yl]carbamate:hydrochlorid;

[1-(4-fluorophenoxy)-3-[4-[[(2-oxo-3-propan-2-ylbenzimidazole-1-carbonyl)amino]methyl]piperidin-1-yl]propan-2-yl]carbamate:hydrochloride;

[1-(4-methoxyphenoxy)-3-[4-[[(3-methyl-2-oxobenzimidazole-1-carbonyl)amino]methyl]piperidin-1-ium-1-yl]propan-2-yl]carbamate:hydrochloride;

[1-[4-[[(3-ethyl-2-oxobenzimidazole-1-carbonyl)amino]methyl]piperidin-1-yl]-3-phenoxypropan-2-yl]carbamate:hydrochloride;

[1-(4-chlorophenoxy)-3-[4-[[(3-ethyl-2-oxobenzimidazole-1-carbonyl)amino]methyl]piperidin-1-yl]propan-2-yl]carbamate:hydrochloride;

3-cyclopropyl-N-[[1-(3-hydroxy-3-phenylpropyl)piperidin-4-yl]methyl]-2-oxobenzimidazole-1-carboxamide:hydrochloride;

3-cyclopropyl-N-[[1-[3-(4-fluorophenyl)-3-hydroxypropyl]piperidin-1-ium-4-yl]methyl]-2-oxobenzimidazole-1-carboxamide:hydrochloride;

[3-[4-[[(3-cyclopropyl-2-oxobenzimidazole-1-carbonyl)amino]methyl]piperidin-1-ium-1-yl]-1-phenylpropyl]carbamate:hydrochloride;

[1-(4-fluorophenyl)-3-[4-[[(2-oxo-3-propan-2-ylbenzimidazole-1-carbonyl)amino]methyl]piperidin-1-ium-1-yl]propyl]carbamate:hydrochloride;

[1-(4-methoxyphenyl)-3-[4-[[(2-oxo-3-propan-2-ylbenzimidazole-1-carbonyl)amino]methyl]piperidin-1-ium-1-yl]propyl]carbamate:hydrochloride;

N-[[1-[2-(4-fluorophenyl)-2-hydroxyethyl]piperidin-4-yl]methyl]-2-oxo-3-propan-2-ylbenzimidazole-1-carboxamide:hydrochloride;

[1-(4-fluorophenyl)-2-[4-[[(2-oxo-3-propan-2-ylbenzimidazole-1-carbonyl)amino]methyl]piperidin-1-ium-1-yl]ethyl]carbamate:hydrochloride;

[[2-[4-[[(3-cyclopropyl-2-oxobenzimidazole-1-carbonyl)amino]methyl]piperidin-1-ium-1-yl]-1-(3-methoxyphenyl)ethyl]carbamate:hydrochloride;

[1-[4-[[(3-methyl-2-oxobenzimidazole-1-carbonyl)amino]methyl]piperidin-1-yl]-3-phenoxypropan-2-yl]carbamate;

N-[[1-(2-hydroxy-3-phenoxypropyl)piperidin-4-yl]methyl]-2-oxo-3-propan-2-ylbenzimidazole-1-carboxamide; and

[3-[4-[[(2-oxo-3-propan-2-ylbenzimidazole-1-carbonyl)amino]methyl]piperidin-1-yl]-1-phenylpropyl]carbamate.

In accordance with an embodiment of the present invention, the compound represented by the structural formula (I) and pharmaceutical acceptable salts thereof can be prepared by the following steps, starting from amino alcohol compounds represented by the following general structural formula (VI):

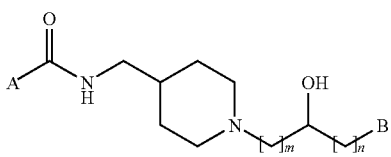

wherein A, B, m, and n are as described above.

The method for preparing the O-carbamoyl compounds represented by the following general structural formula (VII) will be described below in detail:

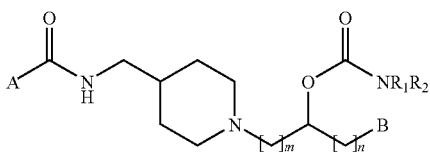

wherein A, B, R1, R2, m, and n are described as above.

The O-carbamoyl compounds represented by the general structural formula (VII) are prepared by reacting, an amino alcohol represented by the general structural formula (VI) with 1,1'-carbonyldiimidazole (CDI) and then with an amine base represented by the following general structural formula (VIII):

NHR1R2    (VIII)

where R1 and R2 are described as above.

This procedure is summarized as set forth in Reaction Scheme 1 below.

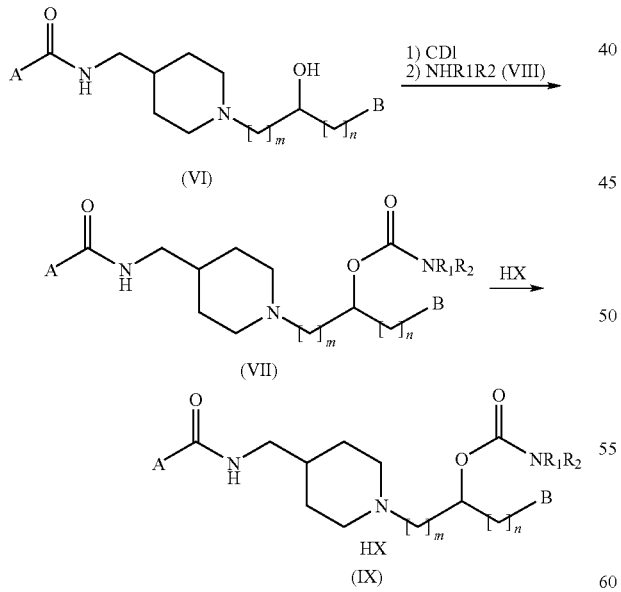

The reaction conditions described in Reaction Scheme I are described in detail as follows. For the conversion of the compound (VI) to the compound (VII), the concentration of the starting material (VI) is about 0.005 to 0.1 moles with 1,1'-carbonyldiimidazole (CDI) ranging from about 2.0 to 3.0 equivalents. This reaction is preferably carried out at a temperature of 10 to 30° C. Without purification, the resulting intermediate is treated with 1 to 1000 equivalents of an amine base represented by the general structural formula (VIII) at a temperature of 10 to 30° C. to give the compound of the general structural formula (VII). For this carbamoylation, ethereal solvents such as diethyl ether and tetrahydrofuran, a halogenated hydrocarbon solvent such as dichloromethane and chloroform, or a mixture thereof may be used.

In Reaction Scheme I, HX represents an acid that is capable of forming a pharmaceutically useful salt with the basic nitrogen atom. Specific examples of the acid used for the preparation of the compound (IX) from the compound (VII) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid, hydroxyethane sulfonic acid, and the like. Additional acids can be found by referring to "Pharmaceutical Salts", J. Pharm. Sci., 1977; 66(1): 1-19. This preparation is executed in a reaction media that can be exemplified by an ethereal solvent such as tetrahydrofuran, an alcoholic solvent such as methanol, an ester solvent such as ethyl acetate, a halogenated hydrocarbon solvent, and mixtures thereof. An ethereal solvent is recommended as an addition solution, including ethyl ether, propyl ether, isopropyl ether, butyl ether, and isobutyl ether. The concentration of the compound (VII) is in the order of about 0.01 to 5 moles.

The piperidine compounds of structural formula (I) may have all the possible isomeric forms, such as the racemic, enantiomeric, and diastereoisomeric forms, and the pharmaceutically acceptable addition salts with inorganic and/or organic acids or with inorganic and/or organic bases of said compound of structural formula (I), for the preparation of medicines intended for the prevention or treatment of diseases of the gastrointestinal tract such as irritable bowel syndrome (IBS), gastric motility disorder and/or visceral pain.

The method for preparing the amino alcohol benzamide compounds represented by following structural formula (X) will be described below in detail:

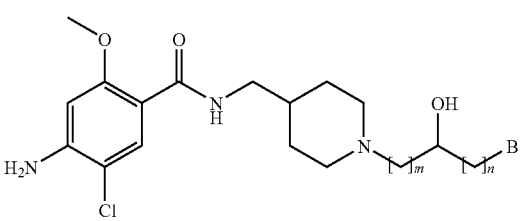

wherein B, m, and n are as described above.

The amino alcohol benzamide compounds represented by the general structural formula (X) are prepared by reacting piperidine benzamide represented by the general structural formula (XI) with an alkyl halide represented by the following general structural formula (XII), an epoxide represented by the following general structural formula (XIII), or a Weinreb amide represented by the following general structural formula (XIV):

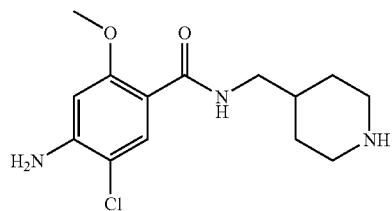
(XI)

(XII-1)

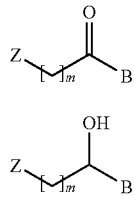
(XII-2)

wherein m is an integer of 1 or 2, Z is a halogen, and B is the same as defined above;

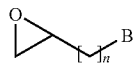
(XIII)

wherein n is an integer of 0 to 2, preferably 0, and B is the same as defined above; and

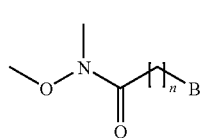
(XIV)

wherein n is an integer of 0 to 2, preferably 0, and B is the same as defined above.

This procedure is summarized as set forth in Reaction Scheme II below.

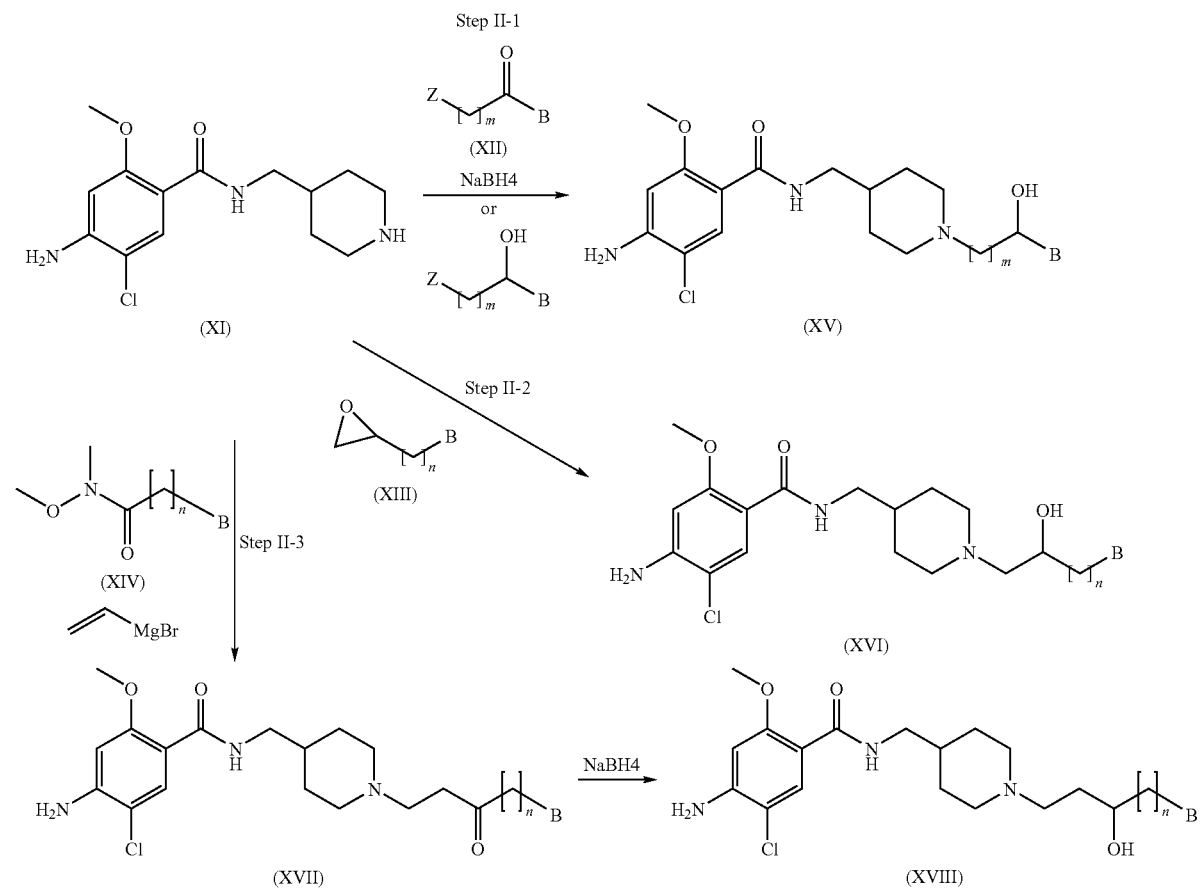

Step II-1

In this step, the desired piperidine compound of structural formula (XV) is prepared by the alkylation of a compound of structural formula (XI) with an alkyl halide (XII) and reduction of the resulting ketone. Details of the reaction conditions described in Step II-1 are as follows. For the conversion of the compounds (XI to the compounds (XV), the concentration of the starting material (XI) is about 0.005 to 0.1 moles with compound (XII-1) ranging from about 1.1 to 3.0 equivalents and a base such as potassium carbonate, cesium carbonate, and triethylamine ranging from about 1.5 to 5.0 equivalents. This reaction is preferably carried out at a temperature of 20 to 80° C. Without purification, the resulting intermediate ketone is treated with 1.0 to 10.0 equivalents of NaBH$_4$ at a temperature of 0 to 30° C. to give the compound of the general structural formula (XV).

For an alternative conversion of compound (XI) to the compound (XV) in which alkyl halide is represented by structural formula (XII-2), the concentration of the starting material (XI) is about 0.005 to 0.1 moles with compound (XII-2) ranging from about 1.1 to 3.0 equivalents and a base such as potassium carbonate, cesium carbonates and triethylamine ranging from about 1.5 to 5.0 equivalents. This reaction is preferably carried out at a temperature of 20 to 80° C. For this reaction, an ethereal solvent such as diethyl ether and tetrahydrofuran, a halogenated hydrocarbon solvent such as dichloromethane and chloroform, an alcohol solvent such as methanol, ethanol, and isopropanol, or acetonitrile may be used.

Step II-2

In this step, the piperidine compound (XVI) is prepared by the epoxide ring opening reaction.

Details of the reaction conditions described in Step II-2 are as follows. For the conversion of the compound (XI) to the compound (XVI), the concentration of the starting material (XI) is about 0.005 to 0.1 moles with compound (XIII) ranging from about 1.1 to 3.0 equivalents. This reaction is preferably carried out at a temperature of 20 to 80° C. For this reaction, ethereal solvents such as diethyl ether and tetrahydrofuran, a halogenated hydrocarbon solvent such as dichloromethane and chloroform, an alcohol solvent such as methanol, ethanol, and isopropanol, or acetonitrile may be used.

Step II-3

In this step, the piperidine compound (XVIII) is prepared by a coupling reaction of a compound of structural formula (XI) with a Weinreb amide compound of structural formula (XIV), and reduction of a resulting ketone compound of structural formula (XVII). Details of the reaction conditions described in Step II-3 are as follows. For the conversion of the compounds (XI) to the compounds (XVIII), the concentration of the Weinreb amide (XIV) is about 0.005 to 0.1 moles with vinyl magnesium bromide ranging from about 1.1 to 2.0 equivalents. Next, the resulting intermediate is treated with a piperidine compound represented by the general compound (XI) and excess water at a temperature 0 to 30° C. to give the compound of the general structural formula (XVII). Without purification, the resulting intermediate ketone is treated with 1.0 to 10.0 equivalents of NaBH$_4$ at a temperature of 0 to 30° C. to give the compound of the general structural formula (XVIII). For this reaction, an ethereal solvent such as diethyl ether and tetrahydrofuran, a halogenated hydrocarbon sol-vent such as dichloromethane and chloroform, an alcohol solvent such as methanol, ethanol, and isopropanol, or acetonitrile may be used.

The method for preparing the amino alcohol benzimidazole compounds represented by the following general structural formula (XIX) will be described below in detail.

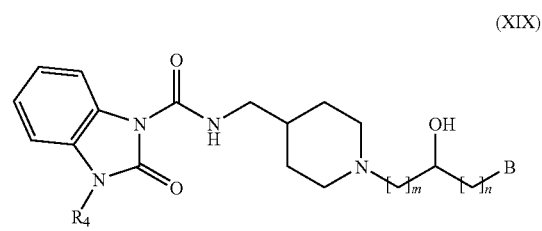

(XIX)

Herein, B, R4, m, and n are as defined above.

The amino alcohol benzimidazole compounds represented by the general structural formula (XIX) are prepared by reacting piperidine benzimidazole represented by the general structural formula (XX) with an alkyl halide represented by the following general structural formula (XII) or an epoxide represented by the following general structural formula (XIII):

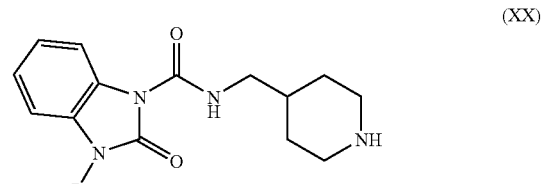

(XX)

(XII-1)

(XII-2)

wherein m is an integer of 1 or 2, Z is a halogen, and B is the same as defined above; and

(XIII)

wherein n is an integer of 0 to 2, and B is the same as defined above.

This procedure is summarized as set forth in Reaction Scheme III below.

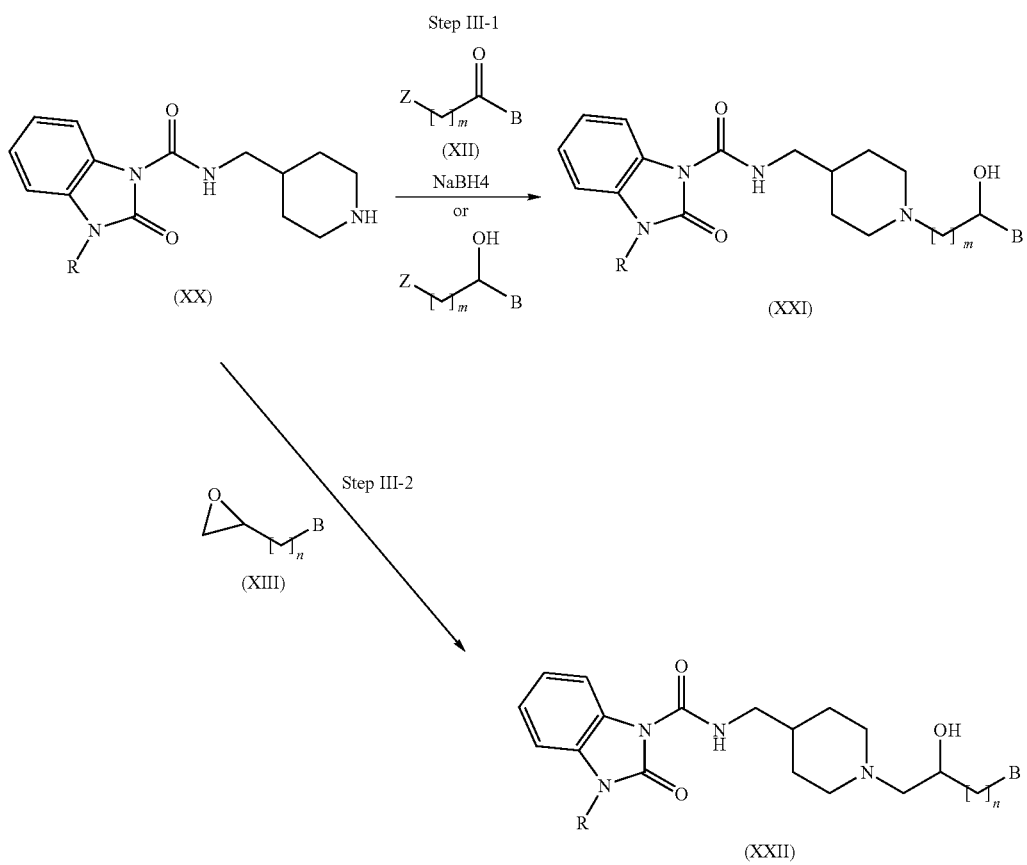

Step III-1

In this step, the piperidine compound of structural formula (XXI) is prepared by the alkylation of a compound of structural formula (XX) with an alkyl halide and reduction. The reaction may be carried out under the same conditions as described in Step II-1.

Step III-2

In this step, the piperidine compound of structural formula (XXII) is prepared by the epoxide ring opening reaction. The reaction may be carried out under the same conditions as described in Step II-2.

It should be noted that the stereochemistry of the product (I, IV, or V) depends solely on that of the starting material (XII or XIII); a starting material (XII or XIII) with an (S)-enantiomer yields only a product with an (S)-enantiomer, and a starting material (XII or XIII) with an (R)-enantiomer yields only a product with an (R)-enantiomer.

Based on the therapeutic activities of the novel piperidine compounds as shown in the following examples, another embodiment provides a pharmaceutical composition including the piperidine compounds represented by structural formula (I), in particular, the compounds represented by structural formula (IV) and (V), as an active ingredient.

In another embodiment, provided is a pharmaceutical composition including an effective amount of the piperidine compounds represented by structural formula (I), in particular, the compounds represented by structural formula (IV) and (V), for treating disorders of gastrointestinal tract such as irritable bowel syndrome, gastrointestinal motility disorder (e.g., gastric motility disorder), constipation, visceral pain, and the like.

Another embodiment provides a method of treating disorders of gastrointestinal tract, such as irritable bowel syndrome (IBS), gastrointestinal motility disorder (e.g., gastric motility disorder), constipation, and visceral pain, in a mammal including administering the composition of the compound of structural formula (I) to a mammal in need of gastrointestinal tract disorder therapy.

The compounds of structural formula (I) are useful in treating IBS, specifically constipation-predominant IBS, constipation, and other gastrointestinal disorders associated with gastrointestinal motility disorder, because they can increase gastrointestinal motility.

Additionally, the compounds of structural formula (I) are useful in alleviating visceral pain caused by IBS and/or other gastrointestinal disorders, because they can reduce visceral pain and discomfort associated with IBS and the like.

The compounds of structural formula (I) may be administered orally or parenterally, and alone or in combination with conventional pharmaceutical carriers. Applicable solid carriers can include one or more substances that may also act as flavoring agents, lubricants, solubilizers, suspending agents, fillers, glidants, compression aids, binders, tablet-disintegrating agents, or encapsulating materials. In powders, the carrier may be a finely divided solid that is in admixture with the finely divided active ingredient. In tablets, the active ingredient is mixed with a carrier having necessary compression properties in suitable proportions and compacted in the shape and size desired. The powders and tablets may contain up to 99% of the active ingredient.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins. Liquid carriers may be used in preparing solutions, suspensions, emulsions, syrups, and elixirs.

The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g., cellulose derivatives, preferably a sodium carboxymethyl cellulose solution), alcohols (including monohydric alcohols and polyhydric alcohols, e.g., glycols) and their derivatives, and oils (e.g., fractionated coconut oil and arachis oil).

For parenteral administration, the carrier can also be an oily ester such as ethyl oleate and isopropyl myristate. Sterile liquid carriers are used in sterile liquid form compositions for parenteral administration. Liquid pharmaceutical compositions that are sterile solutions or suspensions can be utilized by, for example, intramuscular, intraperitoneal, or subcutaneous injection. Sterile solutions can also be administered intravenously.

Oral administration may be either in liquid or solid composition form. Preferably, the pharmaceutical compositions containing the present compounds are in unit dosage form, e.g., as tablets or capsules. In such form, the composition is sub-divided in unit dosages containing appropriate quantities of the active ingredients. The unit dosage forms can be packaged compositions, for example, packaged powders, vials, ampoules, prefilled syringes, or sachets containing liquids. Alternatively, the unit dosage form can be, for example, a capsule or tablet itself, or it can be an appropriate number of any such compositions in package form. The therapeutically effective dosage to be used may be varied or adjusted by the administering physician, and generally ranges from 0.5 mg to 750 mg, according to the specific condition(s) being treated and the size, age, and response pattern of the patient.

The compounds of structural formula (I) may be administered to patients at a dosage of from 0.7 to 7000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of the patient's condition, and the activity of the compound. The determination of optimum dosages for a particular situation must be clinically done, and is within the skill of the art.

A better understanding of the present invention may be obtained in light of the following examples that are set forth to illustrate, but are not to be construed to limit, the present invention.

Example 1

4-amino-5-chloro-N-[[1-(2-hydroxy-2-phenylethyl)piperidin-4-yl]methyl]-2-methoxybenzamide; Hydrochloride A mixture of 4-amino-5-chloro-2-methoxy-N-((piperidin-4-yl)methyl)benzamide (5.0 mmol), 2-bromoacetophenone (6.0 mmol), and potassium carbonate (7.6 mmol) was stirred in 15 mL of acetonitrile for 2 h. This solution was then concentrated in a rotary evaporator and diluted with ethyl acetate. This mixture was then washed with brine, and the resulting organic layer was dried and purified by column chromatography. This was dissolved in ethanol (10 mL) and was added with sodium borohydride (10.0 mmol) at 0° C. and stirred at 25° C. for 2 h. This solution was concentrated on a rotary evaporator and diluted with ethylacetate. This mixture was washed with brine, dried, and concentrated in vacuo. The residue was purified by column chromatography. The resulting 4-amino-5-chloro-N-((1-(2-hydroxy-2-phenylethyl)piperidin-4-yl)methyl)-2-methoxybenzamide was dissolved in methylene chloride (MC) and the solution was treated with a solution of HCl in ether. The resulting precipitate was filtered to give the title compound.

1H-NMR (CDCl3, 200 MHz) δ8.15 (s, 1H), 7.8 (m, 1H), 7.4-7.2 (m, 5H), 6.35 (s, 1H), 4.95 (m, 1H), 4.4 (s, 2H), 3.9 (s, 3H), 3.4-3.3 (m, 3H), 3.0 (m, 1H), 2.6 (m, 2H), 2.4 (m, 1H), 2.2 (m, 1H), 1.9-1.6 (m, 3H), 1.6-1.4 (m, 2H)

Example 2

4-amino-5-chloro-N-[[1-[2-(4-fluorophenyl)-2-hydroxyethyl]piperidin-4-yl]methyl]-2-methoxybenzamide; hydrochloride The procedure given in Example 1 was followed using 2-bromo-4'-fluoroacetophenone as a reactant, instead of 2-bromoacetophenone, to give the title compound.

1H-NMR (CDCl3, 200 MHz) δ8.1 (s, 1H), 7.8 (m, 1H), 7.4-7.15 (m, 2H), 7.1-6.95 (m, 2H), 6.35 (s, 1H), 4.9 (m, 1H), 4.4 (s, 2H), 3.9 (m, 3H), 3.4-3.2 (m, 3H), 3.1-2.9 (m, 1H), 2.6-2.3 (m, 3H), 2.3-2.1 (m, 1H), 1.9-1.7 (m, 3H), 1.6-1.4 (m, 2H)

Example 3

4-amino-5-chloro-N-[[1-[2-hydroxy-2-(4-methylphenyl)ethyl]piperidin-4-yl]methyl]-2-methoxybenzamide; hydrochloride The procedure given in Example 1 was followed using 2-bromo-4'-methylacetophenone as a reactant, instead of 2-bromoacetophenone, to give the title compound.

1H-NMR (CDCl3, 200 MHz) δ8.1 (s, 1H), 7.8 (m, 1H), 7.3-7.1 (m, 4H), 6.35 (s, 1H), 4.9 (m, 1H), 4.4 (s, 2H), 3.9 (m, 3H), 3.5-3.3 (m, 3H), 3.3-3.1 (m, 1H), 2.7 (m, 2H), 2.6-2.5 (m, 1H), 2.4 (m, 4H), 1.9-1.7 (m, 3H), 1.6-1.5 (m, 2H)

Example 4

4-amino-5-chloro-N-[[1-[2-hydroxy-2-(4-methoxyphenyl)ethyl]piperidin-4-yl]methyl]-2-methoxybenzamide; hydrochloride The procedure given in Example 1 was followed using 2-bromo-4'-methoxyacetophenone as a reactant, instead of 2-bromoacetophenone, to give the title compound.

1H NMR (CDCl3, 200 MHz) δ8.1 (s, 1H), 7.8 (m, 1H), 7.4-7.2 (m, 2H), 6.95-6.85 (m, 2H), 6.35 (s, 1H), 4.9 (m, 1H), 4.4 (s, 2H), 3.9 (m, 3H), 3.8 (s, 3H), 3.4-3.2 (m, 3H), 3.1-3.0 (m, 1H), 2.6 (m, 2H), 2.5 (m, 1H), 2.3-2.1 (m, 1H), 1.9-1.7 (m, 3H), 1.6-1.4 (m, 2H)

Example 5

4-amino-5-chloro-N-[[1-[2-(4-cyanophenyl)-2-hydroxyethyl]piperidin-4-yl]methyl]-2-methoxybenzamide; hydrochloride The procedure given in Example 1 was followed using 2-bromo-4'-cyanoacetophenone as a reactant, instead of 2-bromoacetophenone, to give the title compound.

1H-NMR (CDCl3, 200 MHz) δ8.1 (s, 1H), 7.8 (m, 1H), 7.65 (m, 2H), 7.55 (m, 2H), 6.35 (s, 1H), 4.9 (m, 1H), 4.45 (s, 2H), 3.9 (m, 3H), 3.4 (m, 2H), 3.2 (m, 1H), 2.95 (m, 1H), 2.7-2.33 (m, 3H), 2.2 (m, 1H), 1.9-1.7 (m, 3H), 1.6-1.4 (m, 2H)

Example 6

4-amino-5-chloro-N-[[1-[2-(4-chlorophenyl)-2-hydroxyethyl]piperidin-4-yl]methyl]-2-methoxybenzamid; hydrochloride The procedure given in Example 1 was followed using 2-bromo-4'-chloroacetophenone as a reactant, instead of 2-bromoacetophenone, to give the title compound.

1H-NMR (CDCl3, 200 MHz) δ8.15 (m, 1H), 7.8 (m, 1H), 7.3 (m, 4H), 6.35 (s, 1H), 4.8 (m, 1H), 4.4 (s, 2H), 3.9 (s, 3H), 3.4-3.2 (m, 3H), 3.05-2.9 (m, 1H), 2.6-2.3 (m, 3H), 2.2 (m, 1H), 1.9-1.6 (m, 3H), 1.6-1.4 (m, 2H)

Example 7

4-amino-5-chloro-N-[[1-[2-hydroxy-2-(4-phenylphenyl)ethyl]piperidin-4-yl]methyl]-2-methoxybenzamide; hydrochloride The procedure given in Example 1 was followed using 2-bromo-4'-phenylacetophenone as a reactant, instead of 2-bromoacetophenone, to give the title compound.

1H-NMR (CDCl3, 200 MHz) δ8.15 (m, 1H), 7.85 (m, 1H), 7.6-7.3 (m, 9H), 6.35 (s, 1H), 5.3 (m, 1H), 4.4 (s, 2H), 3.9 (s, 3H), 3.8-3.4 (m, 4H), 3.2-3.0 (m, 2H), 3.0-2.7 (m, 2H), 2.4-1.6 (m, 3H), 1.6-1.4 (m, 2H)

Example 8

4-amino-5-chloro-N-[[1-[2-hydroxy-2-(2-methoxyphenyl)ethyl]piperidin-4-yl]methyl]-2-methoxybenzamide; hydrochloride The procedure given in Example 1 was followed using 2-bromo-2'-methoxyacetophenone as a reactant, instead of 2-bromoacetophenone, to give the title compound.

1H-NMR (CDCl3, 200 MHz) δ8.15 (m, 1H), 7.85 (m, 1H), 7.6 (m, 1H), 7.3 (m, 1H), 7.0 (m, 1H), 6.9 (m, 1H), 6.35 (s, 1H), 5.25 (m, 1H), 4.4 (s, 2H), 3.9 (s, 3H), 3.8 (s, 3H), 3.6 (m, 2H), 3.1-3.0 (m, 2H), 2.9-2.7 (m, 4H), 1.9-1.7 (m, 3H), 1.7-1.4 (m, 2H)

Example 9

4-amino-5-chloro-N-[[1-[2-hydroxy-2-(3-methoxyphenyl)ethyl]piperidin-4-yl]methyl]-2-methoxybenzamide; hydrochloride The procedure given in Example 1 was followed using 2-bromo-3% methoxyacetophenone as a reactant, instead of 2-bromoacetophenone, to give the title compound.

1H-NMR (CDCl3, 200 MHz) δ8.15 (m, 1H), 7.85 (m, 1H), 7.3-7.2 (m, 1H), 7.0-6.9 (m, 2H), 6.85 (m, 1H), 6.35 (s, 1H), 4.8 (m, 1H), 4.4 (s, 2H), 3.9 (s, 3H), 3.8 (s, 3H), 3.4-3.2 (m, 3H), 3.0 (m, 1H), 2.6 (m, 2H), 2.4 (m, 1H), 2.2 (m, 1H), 1.9-1.6 (m, 3H), 1.6-1.4 (m, 2H)

Example 10

4-amino-5-chloro-N-[[1-[2-(3,4-dichlorophenyl)-2-hydroxyethyl]piperidin-4-yl]methyl]-2-methoxybenzamide; hydrochloride The procedure given in Example 1 was followed using 2-bromo-3',4'-dichloroacetophenone as a reactant, instead of 2-bromoacetophenone, to give the title compound.

1H-NMR (CDCl3, 200 MHz) δ8.15 (s, 1H), 7.8 (m, 14), 7.5 (s, 1H), 7.45 (m, 1H), 7.2 (m, 1H), 6.35 (s, 1H), 4.8 (m, 1H), 4.4 (s, 2H), 3.9 (s, 3H), 3.4 (m, 2H), 3.3-3.2 (m, 1H), 3.0 (m, 1H), 2.6-2.3 (m, 3H), 2.2 (m, 1H), 1.9-1.6 (m, 3H), 1.6-1.3 (m, 2H)

Example 11

4-amino-5-chloro-N-[[1-[2-(2,4-difluorophenyl)-2-hydroxyethyl]piperidin-4-yl]methyl]-2-methoxybenzamide; hydrochloride The procedure given in Example 1 was followed using 2-bromo-2',4'-difluoroacetophenone as a reactant, instead of 2-bromoacetophenone, to give the title compound.

1H-NMR (CDCl3, 200 MHz) δ8.15 (s, 1H), 7.85 (m, 1H), 7.65 (m, 1H), 7.0-6.7 (m, 2H), 6.35 (s, 1H), 5.3 (m, 1H), 4.4 (s, 2H), 3.9 (s, 3H), 3.5 (m, 1H), 3.4 (m, 2H), 3.2 (m, 2H), 2.9-2.2 (m, 4H), 2.7-2.4 (m, 2H), 2.0-1.8 (m, 3H), 1.8-1.6 (m, 2H)

Example 12

4-amino-N-[[1-[2-(4-tert-butylphenyl)-2-hydroxyethyl]piperidin-4-yl]methyl]-5-chloro-2-methoxybenzamide; hydrochloride The procedure given in Example 1 was followed using 2-bromo-4'-tert-butylacetophenone as a reactant, instead of 2-bromoacetophenone, to give the title compound.

1H-NMR (CDCl3, 200 MHz) δ8.15 (s, 1H), 7.8 (m, 1H), 7.45-7.3 (m, 4H), 6.35 (s, 1H), 4.8 (m, 1H), 4.4 (s, 2H), 3.9 (s, 3H), 3.4-3.2 (m, 3H), 3.0 (m, 1H), 2.6 (m, 2H), 2.4 (m, 1H), 2.15 (m, 1H), 1.9-1.6 (m, 3H), 1.55 (m, 2H), 1.3 (s, 9H)

Example 13

4-amino-5-chloro-N-[[1-[2-(2-chlorophenyl)-2-hydroxyethyl]piperidin-4-yl]methyl]-2-methoxybenzamide; hydrochloride The procedure given in Example 1 was followed using 2-bromo-2'-chloroacetophenone as a reactant, instead of 2-bromoacetophenone, to give the title compound.

1H-NMR (CDCl3, 200 MHz) δ8.15 (s, 1H), 7.85 (m, 1H), 7.75 (m, 1H), 7.3 (m, 3H), 6.35 (s, 1H), 5.3 (m, 1H), 4.4 (s,

2H), 3.9 (s, 3H), 3.4 (m, 3H), 3.05 (m, 1H), 2.85 (m, 1H), 2.5 (m, 2H), 2.3 (m, 1H), 1.9-1.7 (m, 3H), 1.6 (m, 2H)

Example 14

4-amino-5-chloro-N-[[1-[2-(2,4-dimethylphenyl)-2-hydroxyethyl]piperidin-4-yl]methyl]-2-methoxybenzamide; hydrochloride The procedure given in Example 1 was followed using 2-bromo-2',4'-dimethylacetophenone as a reactant, instead of 2-bromoacetophenone, to give the title compound.
1H-NMR (CDCl3, 200 MHz) δ8.15 (s, 1H), 7.8 (m, 1H), 7.45 (m, 1H), 7.05 (m, 1H), 6.95 (m, 1H), 6.35 (m, 1H), 5.05 (m, 1H), 4.4 (s, 2H), 3.9 (s, 3H), 3.4-3.3 (m, 3H), 3.0 (m, 1H), 2.6-2.4 (m 3H), 2.35 (m, 6H), 2.2 (m, 1H), 1.9-1.6 (m, 3H), 1.55 (m, 2H)

Example 15

4-amino-5-chloro-N-[[1-[2-(2,5-dimethoxyphenyl)-2-hydroxyethyl]piperidin-4-yl]methyl]-2-methoxybenzamide; hydrochloride The procedure given in Example 1 was followed using 2-bromo-2',5'-dimethoxyacetophenone as a reactant, instead of 2-bromoacetophenone, to give the title compound.
1H-NMR (CDCl3, 200 MHz) δ8.15 (s, 1H), 7.8 (m, 1H), 7.2 (m, 1H), 6.8 (s, 2H), 6.35 (m, 1H), 5.2 (m, 1H), 4.45 (s, 2H), 3.9 (s, 3H), 3.8 (m, 6H), 3.35 (m, 2H), 3.0 (m, 1H), 2.8 (m, 1H), 2.55 (m 2H), 2.2 (m, 1H), 1.9-1.7 (m, 3H), 1.5 (m 2H)

Example 16

4-amino-5-chloro-N-[[1-[2-[4-(difluoromethoxy)phenyl]-2-hydroxyethyl]piperidin-4-yl]methyl]-2-methoxybenzamide; hydrochloride The procedure given in Example 1 was followed using 2-bromo-4'-(difluoromethoxy)acetophenone as a reactant, instead of 2-bromoacetophenone, to give the title compound.
1H-NMR (CDCl3, 200 MHz) δ8.15 (s, 1H), 7.8 (m, 1H), 7.4 (m, 2H), 7.1 (m, 2H), 6.35 (m, 1H), 4.85 (m, 1H), 4.45 (s, 2H), 3.9 (s, 3H), 3.4-3.2 (m, 3H), 3.0 (m, 1H), 2.7-2.4 (m, 3H), 2.2 (m 1H), 1.9-1.7 (m, 3H), 1.5 (m 2H)

Example 17

4-amino-5-chloro-N-[[1-[2-(3,4-difluorophenyl)-2-hydroxyethyl]piperidin-4-yl]methyl]-2-methoxybenzamide; hydrochloride The procedure given in Example 1 was followed using 2-bromo-3',4'-difluoroacetophenone as a reactant, instead of 2-bromoacetophenone, to give the title compound.
1H-NMR (CDCl3, 200 MHz) δ8.15 (s, 1H), 7.8 (m, 1H), 7.3-7.1 (m, 3H), 6.35 (m, 1H), 4.85 (m, 1H), 4.45 (s, 2H), 3.9 (s, 3H), 3.5-3.2 (m, 3H), 3.0 (m, 1H), 2.7-2.4 (m, 3H), 2.2 (m 1H), 1.9-1.7 (m, 3H), 1.5 (m 2H)

Example 18

4-amino-5-chloro-N-[[1-[2-hydroxy-2-[4-(trifluoromethyl)phenyl]ethyl]piperidin-4-yl]methyl]-2-methoxybenzamide; hydrochloride The procedure given in Example 1 was followed using 2-bromo-4'-(trifluoromethyl)acetophenone as a reactant, instead of 2-bromoacetophenone, to give the title compound.
1H-NMR (CDCl3, 200 MHz) δ8.15 (s, 1H), 7.8 (m, 1H), 7.6 (m, 2H), 7.5 (m, 2H), 6.35 (m, 1H), 4.9 (m, 1H), 4.45 (s, 2H), 3.9 (s, 3H), 3.4 (m, 2H), 3.3 (m, 1H), 3.0 (m, 1H), 2.7-2.3 (m, 3H), 2.2 (m 1H), 1.9-1.7 (m, 3H), 1.5 (m 2H)

Example 19

4-amino-5-chloro-N-[[1-[2-(2,4-dichlorophenyl)-2-hydroxyethyl]piperidin-4-yl]methyl]-2-methoxybenzamide; hydrochloride The procedure given in Example 1 was followed using 2-bromo-2',4'-dichloroacetophenone as a reactant, instead of 2-bromoacetophenone, to give the title compound.
1H-NMR (CDCl3, 200 MHz) δ8.15 (s, 1H), 7.8 (m, 1H), 7.65 (m, 2H), 7.35 (m, 2H), 6.35 (m, 1H), 5.25 (m, 1H), 4.45 (s, 2H), 3.9 (s, 3H), 3.4 (m, 2H), 3.0 (m, 1H), 2.8 (m, 1H), 2.6-2.2 (m, 3H), 1.9-1.7 (m, 3H), 1.5 (m 2H)

Example 20

4-amino-5-chloro-N-[[1-[(2S)-2-hydroxy-2-phenylethyl]piperidin-4-yl]methyl]-2-methoxybenzamide; hydrochloride A mixture of 4-amino-5-chloro-2-methoxy-N-((piperidin-4-yl)methyl)benzamide (5.0 mmol), (S)-styrene oxide (6.0 mmol) was refluxed in 30 ml of isopropanol for 4 h. This solution was then concentrated on a rotary evaporator and diluted with ethyl acetate. This mixture was then washed with brine, and the resulting organic layer was dried and purified by column chromatography. The resulting 4-amino-5-chloro-N-[[1-[(2S)-2-hydroxy-2-phenylethyl]piperidin-4-yl]methyl]-2-methoxybenzamide was dissolved in MC and the solution treated with a solution of HCl in ether. The resulting precipitate was filtered to give the title compound.
1H-NMR (CDCl3, 200 MHz) δ8.15 (m, 1H), 8.0-7.9 (br, 1H), 7.5-7.3 (m, 5H), 6.35 (s, 1H), 5.45 (br, 1H), 4.4 (s, 2H), 3.9 (s, 3H), 3.5-2.7 (m, 6H), 2.2-2.0 (m, 2H), 1.9-1.4 (m, 5H)

Example 21

4-amino-5-chloro-N-[[1-[(2R)-2-hydroxy-2-phenylethyl]piperidin-4-yl]methyl]-2-methoxybenzamide; hydrochloride The procedure given in Example 20 was followed using (R)-styrene oxide as a reactant, instead of (S)-styrene oxide, to give the title compound.
1H-NMR (CDCl3, 200 MHz) δ8.15 (, 1H), 8.0-7.9 (br, 1H), 7.5-7.3 (m, 5H), 6.35 (s, 1H), 5.2 (br, 1H), 4.4 (s, 2H), 3.9 (s, 3H), 3.5-2.7 (m, 6H), 2.2-2.0 (m, 2H), 1.9-1.4 (m, 5H)

Example 22

[2-[4-[[(4-amino-5-chloro-2-methoxybenzoyl)amino]methyl]piperidin-1-yl]-1-phenylethyl]carbamate; hydrochloride 4-amino-5-chloro-N-[[1-(2-hydroxy-2-phenylethyl)piperidin-4-yl]methyl]-2-methoxybenzamide (1.5 mmol) from Example 1 was dissolved in 10 mL of THF and added with 1,1'-carbonyl diimidazole (12 mmol) at 0° C. The reaction mixture was stirred at room temperature for 2 h, followed by the addition of excess ammonium hydroxide (3 ml) at room temperature. After 2 h stirring at room temperature, water was added to terminate the reaction. The organic layer was extracted 3 times with dichloromethane, dried, and concentrated in vacuo. The resulting carbamate was dissolved in MC and the solution treated with a solution of HCl in ether. The resulting precipitate was filtered to give the title compound.

1H-NMR (CDCl3, 200 MHz) δ8.1 (s, 1H), 7.8 (m, 1H), 7.4-7.2 (m, 5H), 6.35 (s, 1H), 5.9 (m, 1H), 4.7 (m, 2H), 4.4 (s, 2H), 3.9 (m, 3H), 3.3 (m, 2H), 3.1-2.8 (m, 3H), 2.6-2.5 (m, 1H), 2.2-2.0 (m, 2H), 1.8-1.3 (m, 5H)

Example 23

[2-[4-[[(4-amino-5-chloro-2-methoxybenzoyl)amino]methyl]piperidin-1-yl]-1-(4-fluorophenyl)ethyl]carbamate; hydrochloride The procedure given in Example 22 was followed using 4-amino-5-chloro-N-[[1-[2-(4-fluorophenyl)-2-hydroxyethyl]piperidin-4-yl]methyl]-2-methoxybenzamide from Example 2 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.1 (s, 1H), 7.8 (m, 1H), 7.4-7.2 (m, 2H), 7.15-7.0 (m, 2H), 6.35 (s, 1H), 5.9-5.8 (m, 1H), 5.1-4.8 (br, 2H), 4.4 (s, 2H), 3.9 (m, 3H), 3.4 (m, 2H), 3.3-3.0 (m, 3H), 2.8-2.6 (m, 2H), 2.5-2.3 (m, 2H), 1.9-1.5 (m, 5H)

Example 24

[2-[4-[[(4-amino-5-chloro-2-methoxybenzoyl)amino]methyl]piperidin-1-yl]-1-(4-methylphenyl)ethyl]carbamate; hydrochloride The procedure given in Example 22 was followed using 4-amino-5-chloro-N-[[1-[2-hydroxy-2-(4-methylphenyl)ethyl]piperidin-4-yl]methyl]-2-methoxybenzamide from Example 3 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.1 (s, 1H), 7.8 (m, 1H), 7.3-7.1 (m, 4H), 6.35 (s, 1H), 5.9-5.8 (m, 1H), 4.9 (m, 2H), 4.4 (s, 2H), 3.9 (m, 3H), 3.4 (m, 2H), 3.2-2.9 (m, 3H), 2.6 (m, 1H), 2.35 (s, 3H), 2.3-2.1 (m, 2H), 1.9-1.5 (m, 5H)

Example 25

[2-[4-[[(4-amino-5-chloro-2-methoxybenzoyl)amino]methyl]piperidin-1-yl]-1-(4-cyanophenyl)ethyl]carbamate; hydrochloride The procedure given in Example 22 was followed using 4-amino-5-chloro-N-[[1-[2-(4-cyanophenyl)-2-hydroxyethyl]piperidin-4-yl]methyl]-2-methoxybenzamide from Example 5 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.1 (s, 1H), 7.8 (m, 1H), 7.7 (m, 2H), 7.5 (m, 2H), 6.35 (s, 1H), 5.9-5.8 (m, 1H), 5.0-4.8 (br, 2H), 4.4 (s, 2H), 3.9 (m, 3H), 3.4 (m, 2H), 3.1-2.9 (m, 3H), 2.7-2.6 (m, 1H), 2.4-2.2 (m, 2H), 1.9-1.7 (m, 3H), 1.5 (m, 2H)

Example 26

[2-[4-[[(4-amino-5-chloro-2-methoxybenzoyl)amino]methyl]piperidin-1-yl]-1-(4-phenylphenyl)ethyl]carbamate; hydrochloride The procedure given in Example 22 was followed using 4-amino-5-chloro-N-[[1-[2-hydroxy-2-(4-phenylphenyl)ethyl]piperidin-4-yl]methyl]-2-methoxybenzamide from Example 7 as a reactant, instead of 4-amino-5-chloro-N-[[1-(2-hydroxy-2-phenylethyl)piperidin-4-yl]methyl]-2-methoxybenzamide, to give the title compound.

1H-NMR (DMSO-d6, 200 MHz) δ10.2 (br, 1H), 8.05 (s, 1H), 7.7 (m, 5H), 7.5-7.3 (m, 4H), 6.9-6.8 (m, 2H), 6.5 (s, 1H), 6.05 (m, 1H), 3.9 (s, 3H), 3.6 (m, 2H), 3.4 (m, 3H), 3.2 (m, 1H), 3.0 (m, 2H), 1.9-1.4 (m, 5H)

Example 27

[2-[4-[[(4-amino-5-chloro-2-methoxybenzoyl)amino]methyl]piperidin-1-yl]-1-(3-methoxyphenyl)ethyl]carbamate; hydrochloride The procedure given in Example 22 was followed using 4-amino-5-chloro-N-[[1-[2-hydroxy-2-(3-methoxyphenyl)ethyl]piperidin-4-yl]methyl]-2-methoxybenzamide from Example 9 as a reactant, instead of 4-amino-5-chloro-N-[[1-(2-hydroxy-2-phenylethyl)piperidin-4-yl]methyl]-2-methoxybenzamide, to give the title compound.

1H-NMR (DMSO-d6, 200 MHz) δ10.1 (br, 1H), 8.05 (s, 1H), 7.65 (m, 1H), 7.4-7.3 (m, 1H), 7.0-6.8 (m, 5H), 6.5 (s, 1H), 6.0 (m, 1H), 3.9 (s, 3H), 3.85 (s, 3H), 3.6 (m, 2H), 3.4 (m, 3H), 3.2 (m, 1H), 3.0 (m, 2H), 1.9-1.4 (m, 5H)

Example 28

[2-[4-[[(4-amino-5-chloro-2-methoxybenzoyl)amino]methyl]piperidin-1-yl]-1-(3,4-dichlorophenyl)ethyl]carbamate; hydrochloride The procedure given in Example 22 was followed using 4-amino-5-chloro-N-[[1-[2-(3,4-dichlorophenyl)-2-hydroxyethyl]piperidin-4-yl]methyl]-2-methoxybenzamide from Example 10 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.85 (m, 1H), 7.5 (m, 2H), 7.3 (m, 1H), 6.35 (s, 1H), 5.95 (m, 1H), 4.4 (s, 2H), 3.9 (s, 3H), 3.4 (m, 2H), 3.3-3.0 (m, 3H), 2.7 (m, 1H), 2.6-2.3 (m, 2H), 1.9-1.6 (m, 5H)

Example 29

[2-[4-[[(4-amino-5-chloro-2-methoxybenzoyl)amino]methyl]piperidin-1-yl]-1-(2-chlorophenyl)ethyl]carbamate; hydrochloride The procedure given in Example 22 was followed using 4-amino-5-chloro-N-[[1-[2-(2-chlorophenyl)-2-hydroxyethyl]piperidin-4-yl]methyl]-2-methoxybenzamide from Example 13 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.8 (m, 1H), 7.5-7.2 (m, 4H), 6.35 (m, 1H), 6.3 (m, 1H), 5.1 (m, 2H), 4.45 (s, 2H), 3.9 (s, 3H), 3.4-3.2 (m, 3H), 3.0 (m, 1H), 2.9 (m 1H), 2.7 (m, 1H), 2.3 (m, 2H), 1.9-1.6 (m, 3H), 1.55 (m, 2H)

Example 30

[2-[4-[[(4-amino-5-chloro-2-methoxybenzoyl)amino]methyl]piperidin-1-yl]-1-(2,4-dimethylphenyl)ethyl]carbamate; hydrochloride The procedure given in Example 22 was followed using 4-amino-5-chloro-N-[[1-[2-(2,4-dimethylphenyl)-2-hydroxyethyl]piperidin-4-yl]methyl]-2-methoxybenzamide from Example 14 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.8 (m, 1H), 7.05 (m, 1H), 7.0 (m, 2H), 6.35 (s, 1H), 6.1 (m, 1H), 4.9 (br, 2H), 4.45 (s, 2H), 3.9 (s, 3H), 3.4 (m, 2H), 3.2 (m, 1H), 3.05-2.9 (m, 2H), 2.6 (m, 2H), 2.5-2.1 (m, 7H), 1.9-1.5 (m, 5H)

Example 31

[2-[4-[[(4-amino-5-chloro-2-methoxybenzoyl)amino]methyl]piperidin-1-yl]-1-(2,5-dimethoxyphenyl)ethyl]carbamate; hydrochloride The procedure given in Example 22 was followed using 4-amino-5-chloro-N-[[1-[2-(2,5-dimethoxyphenyl)-2-hydroxyethyl]piperidin-4-yl]methyl]-2-methoxybenzamide from Example 15 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.8 (m, 1H), 6.95 (s, 1H), 6.8 (s, 2H), 6.35 (s, 1H), 6.3 (m, 1H), 4.95 (br, 2H), 4.45 (s, 2H), 3.9 (s, 3H), 3.8 (d, 6H), 3.4-3.2 (m, 3H), 3.0 (m, 1H), 2.9 (m, 1H), 2.7 (m, 1H), 2.4-2.2 (m, 2H), 1.9-1.7 (m, 3H), 1.5 (m 2H)

Example 32

[2-[4-[[(4-amino-5-chloro-2-methoxybenzoyl)amino]methyl]piperidin-1-yl]-1-[4-(difluoromethoxy)phenyl]ethyl]carbamate; hydrochloride The procedure given in Example 22 was followed using 4-amino-5-chloro-N-[[1-[2-[4-(difluoromethoxy)phenyl]-2-hydroxyethyl]piperidin-4-yl]methyl]-2-methoxybenzamide from Example 16 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.8 (m, 1H), 7.4 (m, 2H), 7.15 (m, 2H), 6.65 (s, 1H), 6.35 (s, 1H), 5.9 (m, 1H), 5.1-4.8 (br, 2H), 4.45 (s, 2H), 3.9 (s, 3H), 3.4-3.2 (m, 2H), 3.3-3.0 (m, 3H), 2.7 (m, 1H), 2.5-2.2 (m, 2H), 1.9-1.5 (m, 5H)

Example 33

[2-[4-[[(4-amino-5-chloro-2-methoxybenzoyl)amino]methyl]piperidin-1-yl]-1-(3,4-difluorophenyl)ethyl]carbamate; hydrochloride The procedure given in Example 22 was followed using 4-amino-5-chloro-N-[[1-[2-(3,4-difluorophenyl)-2-hydroxyethyl]piperidin-4-yl]methyl]-2-methoxybenzamide from Example 17 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.8 (m, 1H), 7.3-7.0 (m, 3H), 6.35 (s, 1H), 5.8 (m, 1H), 5.1-4.8 (br, 2H), 4.4 (s, 2H), 3.9 (s, 3H), 3.35 (m, 2H), 3.2-2.9 (m, 2H), 2.6 (m, H), 2.4-2.1 (m, 3H), 1.9-1.4 (m, 5H)

Example 34

[2-[4-[[(4-amino-5-chloro-2-methoxybenzoyl)amino]methyl]piperidin-1-yl]-1-[4-(trifluoromethyl)phenyl]ethyl]carbamate; hydrochloride The procedure given in Example 22 was followed using 4-amino-5-chloro-N-[[1-[2-hydroxy-2-[4-(trifluoromethyl)phenyl]ethyl]piperidin-4-yl]methyl]-2-methoxybenzamide from Example 18 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.8 (m, 1H), 7.65 (m, 2H), 7.5 (m, 2H), 6.35 (s, 1H), 5.9 (m, 1H), 5.1-4.8 (br, 2H), 4.4 (s, 2H), 3.9 (s, 3H), 3.35 (m, 2H), 3.2-2.9 (m, 3H), 2.6 (m, H), 2.4-2.1 (m, 2H), 1.9-1.4 (m, 5H)

Example 35

[2-[4-[[(4-amino-5-chloro-2-methoxybenzoyl)amino]methyl]piperidin-1-yl]-1-(2,4-dichlorophenyl)ethyl]carbamate; hydrochloride The procedure given in Example 22 was followed using 4-amino-5-chloro-N-[[1-[2-(2,4-dichlorophenyl)-2-hydroxyethyl]piperidin-4-yl]methyl]-2-methoxybenzamide from Example 19 as a reactant, instead of 4-amino-5-chloro-N-[[1-(2-hydroxy-2-phenylethyl)piperidin-4-yl]methyl]-2-methoxybenzamide, to give the title compound.

1H-NMR (CDCl3, 200 MHz) δ8.15 (s, 1H), 7.8 (m, 1H), 7.5-7.2 (m, 3H), 6.35 (s, 1H), 6.2 (m, 1H), 5.1-4.8 (br, 2H), 4.4 (s, 2H), 3.9 (s, 3H), 3.35 (m, 2H), 3.2 (m, 1H), 3.0 (m, 1H), 2.8 (m, 1H), 2.65 (m, 1H), 2.35 (m, 2H), 1.9-1.4 (m, 5H)

Example 36

4-amino-5-chloro-N-[[1-(3-hydroxy-3-phenylpropyl)piperidin-4-yl]methyl]-2-methoxybenzamide; hydrochloride A mixture of 4-amino-5-chloro-2-methoxy-N-((piperidin-4-yl)methyl)benzamide (5.0 mmol), 3-chloropropiophenone (6.0 mmol), potassium carbonate (7.6 mmol), and potassium iodide (7.6 mmol) was refluxed in 15 mL of acetonitrile for 12 h. This solution was then concentrated on a rotary evaporator and diluted with ethyl acetate. This mixture was then washed with brine, and the resulting organic layer was dried and purified by column chromatography. This was dissolved in ethanol (10 mL) and was added with sodium borohydride (10.0 mmol) at 0° C. and stirred at 25° C. for 2 h. This solution was concentrated on a rotary evaporator and diluted with ethylacetate. This mixture was washed with brine, dried, and concentrated in vacuo. The residue was purified by column chromatography. The resulting 4-amino-5-chloro-N-[[1-(3-hydroxy-3-phenylpropyl)piperidin-4-yl]methyl]-2-methoxybenzamide was dissolved in MC and the solution treated with a solution of HCl in ether. The resulting precipitate was filtered to give the title compound.

1H-NMR (CDCl3, 200 MHz) δ8.15 (s, 1H), 7.8 (m, 1H), 7.4-7.2 (m, 5H), 6.35 (s, 1H), 4.95 (m, 1H), 4.4 (s, 2H), 3.9 (s, 3H), 3.4-3.1 (m, 4H), 2.75 (m, 2H), 2.3-1.7 (m, 7H), 1.5 (m, 2H)

Example 37

4-amino-5-chloro-N-[[1-[3-(4-fluorophenyl)-3-hydroxypropyl]piperidin-4-yl]methyl]-2-methoxybenzamide; hydrochloride The procedure given in Example 36 was followed using 3-chloro-4'-fluoropropiophenone as a reactant, instead of 3-chloropropiophenone, to give the title compound.

1H-NMR (CDCl3, 200 MHz) δ8.1 (s, 1H), 7.8 (m, 1H), 7.4-7.3 (m, 2H), 7.1-7.0 (m, 2H), 6.35 (s, 1H), 4.9 (m, 1H), 4.4 (s, 2H), 3.9 (s, 3H), 3.4-3.1 (m, 4H), 2.9-2.7 (m, 2H), 2.4-2.0 (m, 2H), 1.9-1.7 (m, 5H), 1.7-1.5 (m, 2H)

Example 38

4-amino-5-chloro-N-[[1-[3-(4-chlorophenyl)-3-hydroxypropyl]piperidin-4-yl]methyl]-2-methoxybenzamide; hydrochloride The procedure given in Example 36 was followed using 3-chloro-4'-chloropropiophenone as a reactant, instead of 3-chloropropiophenone, to give the title compound.

1H-NMR (CDCl3, 200 MHz) δ8.15 (s, 1H), 7.8 (m, 1H), 7.4-7.35 (m, 2H), 7.1-6.9 (m, 2H), 6.35 (s, 1H), 4.9 (m, 1H), 4.4 (s, 2H), 3.9 (s, 3H), 3.4 (m, 2H), 3.3-3.1 (m, 2H), 2.8-2.6 (m, 2H), 2.3-1.7 (m, 7H), 1.5 (m, 2H)

Example 39

4-amino-5-chloro-N-[[1-[3-hydroxy-3-(4-methylphenyl)propyl]piperidin-4-yl]methyl]-2-methoxybenzamide; hydrochloride The procedure given in Example 36 was followed using 3-chloro-4'-methylpropiophenone as a reactant, instead of 3-chloropropiophenone, to give the title compound.

1H-NMR (CDCl3, 200 MHz) δ8.15 (m, 1H), 7.85 (m, 1H), 7.3 (m, 2H), 7.2 (m, 2H), 6.35 (s, 1H), 4.95 (t, 1H), 4.4 (s, 2H), 3.9 (s, 3H), 3.4 (m, 2H), 3.2 (m, 2H), 2.8-2.7 (m, 2H), 2.4 (s, 3H), 2.2 (m, 1H), 2.05-1.7 (m, 6H), 1.4-1.2 (m, 2H)

Example 40

4-amino-5-chloro-N-[[1-[3-hydroxy-3-(4-methoxyphenyl)propyl]piperidin-4-yl]methyl]-2-methoxybenzamide; hydrochloride The procedure given in Example 36 was followed using 3-chloro-4'-methoxypropiophenone as a reactant, instead of 3-chloropropiophenone, to give the title compound.

1H-NMR (CDCl3, 200 MHz) δ8.15 (m, 1H), 7.85 (m, 1H), 7.3 (m, 2H), 6.9 (m, 2H), 6.35 (s, 1H), 4.95 (t, 1H), 4.4 (s, 2H), 3.9 (s, 3H), 3.8 (s, 3H), 3.4 (m, 2H), 3.3-3.1 (m, 2H), 2.8-2.6 (m, 2H), 2.2 (m, 1H), 2.2-1.7 (m, 6H), 1.6-1.4 (m, 2H)

Example 41

4-amino-5-chloro-N-[[1-[3-(2-chlorophenyl)-3-hydroxypropyl]piperidin-4-yl]methyl]-2-methoxybenzamide; hydrochloride A mixture of 2-chlorobenzoic acid (5 mmol) and 1,1'-carbonyl diimidazole was stirred in 30 ml of THF for 30 min, and N,O-dimethylhydroxylamie hydrochloride (6.5 mmol) and triethylamie (5 mmol) were added. After 12 h stirring at room temperature, water was added to terminate the reaction. The organic layer was extracted 2 times with ethylacetate and the organic layer was washed with 5% HCl solution and brine, dried, and concentrated in vacuo. The crude product was dissolved in THF (30 ml) and added with 1M solution of vinylmagnesium bromide (5.5 mmol) in THF at 0° C. After 10 min stirring, the mixture was warmed to room temperature and stirred for 1 h, followed by the addition of 4-amino-5-chloro-2-methoxy-N-((piperidin-4-yl)methyl)benzamide (7.5 mmol) and water (7.5 ml) at room temperature. After 30 min stirring at room temperature, water and ethylacetate added and organic layer was washed with brine, dried, and concentrated in vacuo. The residue was purified by column chromatography. This was dissolved in ethanol (10 mL) and was added with sodium borohydride (10.0 mmol) at 0° C. and stirred at 25° C. for 2 h. This solution was concentrated on a rotary evaporator and diluted with ethylacetate. This mixture was washed with brine, dried, and concentrated in vacuo. The resulting 4-amino-5-chloro-N-[[1-[3-(2-chlorophenyl)-3-hydroxypropyl]piperidin-4-yl]methyl]-2-methoxybenzamide was dissolved in MC and the solution treated with a solution of HCl in ether. The resulting precipitate was filtered to give the title compound.

1H-NMR (CDCl3, 200 MHz) δ8.05 (s, 1H), 7.8 (m, 1H), 7.7 (m, 1H), 7.4-7.1 (m, 3H), 5.3 (s, 1H), 4.5 (s, 2H), 3.9 (s, 3H), 3.35 (m, 2H), 3.1 (m, 2H), 2.6 (m, 2H), 2.2-1.6 (m, 7H), 1.5-1.3 (m, 2H)

Example 42

4-amino-5-chloro-N-[[1-[3-(3-chlorophenyl)-3-hydroxypropyl]piperidin-4-yl]methyl]-2-methoxybenzamide; hydrochloride The procedure given in Example 41 was followed using 3-chlorobenzoic acid as a reactant, instead of 2-chlorobenzoic acid, to give the title compound.

1H-NMR (CDCl3, 200 MHz) δ 8.05 (s, 1H), 7.8 (m, 1H), 7.4 (s, 1H), 7.3-7.1 (m, 3H), 6.3 (s, 1H), 4.9 (m, 1H), 4.4 (s, 2H), 3.9 (s, 3H), 3.35 (m, 2H), 3.1 (m, 2H), 2.6 (m, 2H), 2.1-1.9 (m, 1H), 1.9-1.5 (m, 6H), 1.5-1.3 (m, 2H)

Example 43

4-amino-5-chloro-N-[[1-[3-(2-fluorophenyl)-3-hydroxypropyl]piperidin-4-yl]methyl]-2-methoxybenzamide; hydrochloride The procedure given in Example 41 was followed using 2-fluorobenzoic acid as a reactant, instead of 2-chlorobenzoic acid, to give the title compound.

1H-NMR (CDCl3, 200 MHz) δ8.05 (s, 1H), 7.8 (m, 1H), 7.6 (m, 1H), 7.2 (m, 2H), 6.95 (m, 1H), 6.3 (s, 1H), 5.2 (m, 1H), 4.4 (s, 2H), 3.9 (s, 3H), 3.3 (m, 2H), 3.1 (m, 2H), 2.6 (m, 2H), 2.2-1.5 (m, 7H), 1.5-1.1 (m, 2H)

Example 44

4-amino-5-chloro-N-[[1-[3-(3-fluorophenyl)-3-hydroxypropyl]piperidin-4-yl]methyl]-2-methoxybenzamide; hydrochloride The procedure given in Example 41 was followed using 3-fluorobenzoic acid as a reactant, instead of 2-chlorobenzoic acid, to give the title compound.

1H-NMR (CDCl3, 200 MHz) δ8.05 (s, 1H), 7.8 (m, 1H), 7.3 (m, 1H), 7.1 (m, 2H), 6.9 (m, 1H), 6.3 (s, 1H), 4.9 (m, 1H), 4.6 (s, 2H), 3.9 (s, 3H), 3.3 (m, 2H), 3.1 (m, 2H), 2.6 (m, 2H), 2.2-1.5 (m, 7H), 1.5-1.2 (m, 2H)

Example 45

4-amino-5-chloro-N-[[1-[3-(2,3-dichlorophenyl)-3-hydroxypropyl]piperidin-4-yl]methyl]-2-methoxybenzamide; hydrochloride The procedure given in Example 41 was followed using 2,3-dichlorobenzoic acid as a reactant, instead of 2-chlorobenzoic acid, to give the title compound.

1H-NMR (CDCl3, 200 MHz) δ 8.1 (s, 1H), 7.8 (m, 1H), 7.6 (m, 1H), 7.3 (m, 4H), 6.35 (s, 1H), 5.2 (m, 1H), 4.5 (m, 2H), 3.9 (s, 3H), 3.35 (m, 2H), 3.1 (m, 2H), 2.8-2.5 (m, 2H), 2.2-1.6 (m, 7H), 1.4 (m, 2H)

Example 46

4-amino-5-chloro-N-[[1-[3-(2,4-dichlorophenyl)-3-hydroxypropyl]piperidin-4-yl]methyl]-2-methoxy-benzamide; hydrochloride The procedure given in Example 41 was followed using 2,4-dichlorobenzoic acid as a reactant, instead of 2-chlorobenzoic acid, to give the title compound.

1H-NMR (CDCl3, 200 MHz) δ 8.1 (s, 1H), 7.8 (m, 1H), 7.6 (m, 1H), 7.4-7.2 (m, 2H), 6.35 (s, 1H), 5.3 (m, 1H), 4.5 (s, 2H), 3.9 (s, 3H), 3.35 (m, 2H), 3.1 (m, 2H), 2.8-2.5 (m, 2H), 2.2-1.6 (m, 7H), 1.4 (m, 2H)

Example 47

4-amino-5-chloro-N-[[1-[3-(3,4-dichlorophenyl)-3-hydroxypropyl]piperidin-4-yl]methyl]-2-methoxy-benzamide; hydrochloride The procedure given in Example 41 was followed using 3,4-dichlorobenzoic acid as a reactant, instead of 2-chlorobenzoic acid, to give the title compound.

1H-NMR (CDCl3, 200 MHz) δ 8.1 (s, 1H), 7.8 (m, 1H), 7.5-7.3 (m, 2H), 7.2 (m, 1H), 6.35 (s, 1H), 4.95 (m, 1H), 4.5 (s, 2H), 3.9 (s, 3H), 3.35 (m, 2H), 3.2 (m, 2H), 2.8-2.6 (m, 2H), 2.2-1.6 (m, 7H), 1.5 (m, 2H)

Example 48

4-amino-5-chloro-N-[[1-[3-(4-isopropylphenyl)-3-hydroxypropyl]piperidin-4-yl]methyl]-2-methoxy-benzamide; hydrochloride The procedure given in Example 41 was followed using 4-isopropylbenzoic acid as a reactant, instead of 2-chlorobenzoic acid, to give the title compound.

1H-NMR (CDCl3, 200 MHz) δ 8.1 (s, 1H), 7.8 (m, 1H), 7.3-7.15 (m, 4H), 7.2 (m, 2H), 6.3 (s, 1H), 4.9 (m, 1H), 4.5 (s, 2H), 3.9 (s, 3H), 3.35 (m, 2H), 3.2 (m, 2H), 2.9 (m, 1H), 2.6 (m, 2H), 2.2-1.6 (m, 7H), 1.4 (m, 2H), 1.3 (m, 6H)

Example 49

4-amino-5-chloro-N-[[1-[3-(3-methoxyphenyl)-3-hydroxypropyl]piperidin-4-yl]methyl]-2-methoxy-benzamide; hydrochloride The procedure given in Example 41 was followed using 3-methoxybenzoic acid as a reactant, instead of 2-chlorobenzoic acid, to give the title compound.

1H-NMR (CDCl3, 200 MHz) δ 8.1 (s, 1H), 7.8 (m, 1H), 7.3-7.2 (m, 1H), 6.9 (m, 2H), 6.8 (m, 1H), 6.3 (s, 1H), 5.7 (br, 1H), 4.9 (m, 1H), 4.55 (s, 2H), 3.9 (s, 3H), 3.85 (s, 3H), 3.3 (m, 2H), 3.1 (m, 2H), 2.65 (m, 2H); 2.1 (m, 2H), 2.0 (m, 1H), 1.9-1.6 (m, 3H), 1.45 (m, 2H)

Example 50

4-amino-5-chloro-N-[[1-(3-hydroxy-3-thiophen-2-ylpropyl)piperidin-4-yl]methyl]-2-methoxybenza-mide; hydrochloride The procedure given in Example 41 was followed using 2-thiophenecarboxylic acid as a reactant, instead of 2-chlorobenzoic acid, to give the title compound.

1H-NMR (CDCl3, 200 MHz) δ 8.1 (s, 1H), 7.8 (m, 1H), 7.3-7.2 (m, 1H), 6.9 (m, 2H), 6.8 (m, 1H), 6.3 (s, 1H), 5.2 (m, 1H), 4.9 (br, 1H), 4.55 (s, 2H), 3.9 (s, 3H), 3.35 (m, 2H), 3.2 (m, 2H), 2.7 (m, 2H), 2.2 (m, 1H), 2.1 (m, 3H), 1.9-1.6 (m, 3H), 1.45 (m, 2H)

Example 51

4-amino-5-chloro-N-[[1-[4-(4-fluorophenyl)-3-hydroxybutyl]piperidin-4-yl]methyl]-2-methoxybenza-mide; hydrochloride The procedure given in Example 41 was followed using 4-fluorophenylacetic acid as a reactant, instead of 2-chlorobenzoic acid, to give the title compound.

1H-NMR (CDCl3, 200 MHz) δ 8.1 (s, 1H), 7.8 (m, 1H), 7.2 (m, 2H), 7.0 (m, 2H), 6.3 (s, 1H), 4.4 (s, 2H), 4.0 (m, 1H), 3.9 (s, 3H), 3.3 (m, 2H), 3.0 (m, 1H), 2.9-2.6 (m, 4H), 2.3-1.3 (m, 11H)

Example 52

4-amino-5-chloro-N-[[1-[5-(4-fluorophenyl)-3-hydroxypentyl]piperidin-4-yl]methyl]-2-methoxyben-zamide; hydrochloride The procedure given in Example 41 was followed using 3-(4-fluorophenyl)propionic acid as a reactant, instead of 2-chlorobenzoic acid, to give the title compound.

1H-NMR (CDCl3, 200 MHz) δ 8.1 (s, 1H), 7.75 (m, 1H), 7.15 (m, 2H), 7.0 (m, 2H), 6.3 (s, 1H), 4.4 (s, 2H), 3.85 (s, 3H), 3.8 (m, 4H), 3.3 (m, H), 3.2 (m, 1H), 3.0-2.6 (m, 6H), 2.1 (m, 1H), 2.0-1.6 (m, 4H), 1.6-1.3 (m, 2H)

Example 53

[3-[4-[[(4-amino-5-chloro-2-methoxybenzoyl)amino]methyl]piperidin-1-yl]-1-phenylpropyl]carbamate; hydrochloride 4-amino-5-chloro-N-[[1-(3-hydroxy-3-phenylpropyl)piperidin-4-yl]methyl]-2-methoxybenzamide (1.5 mmol) from Example 34 was dissolved in 10 mL of THF and added with 1,1'-carbonyl diimidazole (12 mmol) at 0° C. The reaction mixture was stirred at room temperature for 4 h, followed by the addition of excess ammonium hydroxide (3 ml) at 0° C. After 2 h stirring at room temperature, water was added to terminate the reaction. The organic layer was extracted 3 times with dichloromethane, dried, and concentrated in vacuo. The resulting carbamate was dissolved in dichloromethane and the solution treated with a solution of HCl in ether. The resulting precipitate was filtered to give the title compound.

1H-NMR (CDCl3, 200 MHz) δ 8.15 (s, 1H), 7.75 (m, 1H), 7.4-7.3 (m, 5H), 6.3 (s, 1H), 5.7 (m, 1H), 4.6 (m, 2H), 4.4 (s, 2H), 3.9 (s, 3H), 3.35 (m, 2H), 2.9 (m, 2H), 2.4-2.3 (m, 2H), 2.0-1.8 (m, 2H), 1.8-1.5 (m, 3H), 1.4-1.2 (m, 2H)

Example 54

[3-[4-[[(4-amino-5-chloro-2-methoxybenzoyl)amino]methyl]piperidin-1-yl]-1-(4-fluorophenyl)propyl]carbamate; hydrochloride The procedure given in Example 53 was followed using 4-amino-5-chloro-N-[[1-[3-(4-fluorophenyl)-3-hydroxypropyl]piperidin-4-yl]methyl]-2-methoxybenzamide from Example 35 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.4-7.2 (m, 2H), 7.1-7.0 (m, 2H), 6.35 (s, 1H), 5.7 (m, 1H), 4.6 (m, 2H), 4.4 (s, 2H), 3.9 (s, 3H), 3.4-3.2 (m, 2H), 3.0-2.8 (m, 2H), 2.4-2.1 (m, 4H), 2.0-1.5 (m, 5H), 1.5-1.3 (m, 2H)

Example 55

[3-[4-[[(4-amino-5-chloro-2-methoxybenzoyl)amino]methyl]piperidin-1-yl]-1-(4-chlorophenyl)propyl]carbamate; hydrochloride The procedure given in Example 53 was followed using 4-amino-5-chloro-N-[[1-[3-(4-chlorophenyl)-3-hydroxypropyl]piperidin-4-yl]methyl]-2-methoxybenzamide from Example 36 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.15 (s, 1H), 7.8 (m, 1H), 7.4-7.2 (m, 2H), 7.1-7.0 (m, 2H), 6.35 (s, 1H), 5.7 (m, 1H), 4.7 (m, 2H), 4.4 (s, 2H), 3.9 (s, 3H), 3.4 (m, 2H), 3.1-2.9 (m, 2H), 2.4 (m, 2H), 2.3-1.6 (m, 7H), 1.5-1.3 (m, 2H)

Example 56

[3-[4-[[(4-amino-5-chloro-2-methoxybenzoyl)amino]methyl]piperidin-1-yl]-1-(2-chlorophenyl)propyl]carbamate; hydrochloride The procedure given in Example 53 was followed using 4-amino-5-chloro-N-[[1-[3-(2-chlorophenyl)-3-hydroxypropyl]piperidin-4-yl]methyl]-2-methoxybenzamide from Example 39 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.5-7.1 (m, 4H), 6.3 (s, 1H), 6.05 (m, 1H), 5.0 (m, 2H), 4.5 (m, 2H), 3.9 (s, 3H), 3.3 (m, 2H), 3.0 (m, 2H), 2.55 (m, 2H), 2.1 (m, 2H), 1.8-1.2 (m, 5H), 0.9 (m, 2H)

Example 57

[3-[4-[[(4-amino-5-chloro-2-methoxybenzoyl)amino]methyl]piperidin-1-yl]-1-(2-fluorophenyl)propyl]carbamate; hydrochloride The procedure given in Example 53 was followed using 4-amino-5-chloro-N-[[1-[3-(2-fluorophenyl)-3-hydroxypropyl]piperidin-4-yl]methyl]-2-methoxybenzamide from Example 41 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.4-6.9 (m, 4H), 6.3 (s, 1H), 5.95 (m, 1H), 5.0 (s, 2H), 4.5 (m, 2H), 3.85 (s, 3H), 3.3 (m, 2H), 2.95 (m, 2H), 2.45 (m, 2H), 2.1 (m, 2H), 1.8-1.2 (m, 5H), 0.9 (m, 2H)

Example 58

[3-[4-[[(4-amino-5-chloro-2-methoxybenzoyl)amino]methyl]piperidin-1-yl]-1-(3-fluorophenyl)propyl]carbamate; hydrochloride The procedure given in Example 53 was followed using 4-amino-5-chloro-N-[[1-[3-(3-fluorophenyl)-3-hydroxypropyl]piperidin-4-yl]methyl]-2-methoxybenzamide from Example 42 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.3 (m, 1H), 7.1-6.9 (m, 3H), 6.3 (s, 1H), 5.65 (m, 1H), 4.9 (s, 2H), 4.5 (s, 2H), 3.85 (s, 3H), 3.3 (m, 2H), 2.9 (m, 2H), 2.35 (m, 2H), 2.2-1.8 (m, 2H), 1.8-1.2 (m, 5H), 0.9 (m, 2H)

Example 59

[3-[4-[[(4-amino-5-chloro-2-methoxybenzoyl)amino]methyl]piperidin-1-yl]-1-(2,3-dichlorophenyl)propyl]carbamate; hydrochloride The procedure given in Example 53 was followed using 4-amino-5-chloro-N-[[1-[3-(2,3-dichlorophenyl)-3-hydroxypropyl]piperidin-4-yl]methyl]-2-methoxybenzamide from Example 43 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.4-7.15 (m, 3H), 6.3 (s, 1H), 6.05 (m, 1H), 5.05 (m, 2H), 4.5 (s, 2H), 3.9 (s, 3H), 3.3 (m, 2H), 2.95 (m, 2H), 2.5 (m, 2H), 2.1-1.8 (m, 4H), 1.8-1.5 (m, 3H), 1.3 (m, 2H)

Example 60

[3-[4-[[(4-amino-5-chloro-2-methoxybenzoyl)amino]methyl]piperidin-1-yl]-1-(2,4-dichlorophenyl)propyl]carbamate; hydrochloride The procedure given in Example 53 was followed using 4-amino-5-chloro-N-[[1-[3-(2,4-dichlorophenyl)-3-hydroxypropyl]piperidin-4-yl]methyl]-2-methoxybenzamide from Example 44 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.4-7.15 (m, 3H), 6.3 (s, 1H), 6.05 (m, 1H), 5.05 (br, 2H), 4.5 (s, 2H), 3.9 (s, 3H), 3.35 (m, 2H), 3.05 (m, 2H), 2.6 (m, 2H), 2.1-1.8 (m, 4H), 1.8-1.5 (m, 3H), 1.3 (m, 2H)

Example 61

[3-[4-[[(4-amino-5-chloro-2-methoxybenzoyl)amino]methyl]piperidin-1-yl]-1-(3,4-dichlorophenyl)propyl]carbamate; hydrochloride The procedure given in Example 53 was followed using 4-amino-5-chloro-N-[[1-[3-(3,4-dichlorophenyl)-3-hydroxypropyl]piperidin-4-yl]methyl]-2-methoxybenzamide from Example 45 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.45 (m, 2H), 7.2 (m, 1H), 6.3 (s, 1H), 5.6 (m, 1H), 4.95 (br, 2H), 4.45 (s, 2H), 3.9 (s, 3H), 3.53 (m, 2H), 2.9 (m, 2H), 2.3 (m, 4H), 2.2-1.5 (m, 5H), 1.3 (m, 2H)

Example 62

[3-[4-[[(4-amino-5-chloro-2-methoxybenzoyl)amino]methyl]piperidin-1-yl]-1-(4-isopropylphenyl)propyl]carbamate; hydrochloride The procedure given in Example 53 was followed using 4-amino-5-chloro-N-[[1-[3-(4-isopropylphenyl)-3-hydroxypropyl]piperidin-4-yl]methyl]-2-methoxybenzamide from Example 46 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.3-7.1 (m, 4H), 6.3 (s, 1H), 5.65 (s, 1H), 4.95 (s, 2H), 4.5 (s, 2H), 3.85 (s, 3H), 3.3 (m, 2H), 3.1-2.8 (m, 3H), 2.4 (m, 2H), 2.2-1.8 (m, 4H), 1.8-1.5 (m, 3H), 1.4-1.2 (m, 8H)

Example 63

[3-[4-[[(4-amino-5-chloro-2-methoxybenzoyl)amino]methyl]piperidin-1-yl]-1-(3-methoxyphenyl)propyl]carbamate; hydrochloride The procedure given in Example 53 was followed using 4-amino-5-chloro-N-[[1-[3-(3-methoxyphenyl)-3-hydroxypropyl]piperidin-4-yl]methyl]-2-methoxybenzamide from Example 47 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.25 (m, 1H), 6.9 (m, 3H), 6.3 (s, 1H), 5.7 (m, 1H), 4.9 (s, 2H), 4.55 (s, 2H), 3.9 (s, 3H), 3.8 (s, 3H), 3.35 (m, 2H), 2.95 (m, 2H), 2.4 (m, 2H), 2.2-1.9 (m, 4H), 1.8-1.5 (m, 3H), 1.45-1.2 (m, 2H)

Example 64

[3-[4-[[(4-amino-5-chloro-2-methoxybenzoyl)amino]methyl]piperidin-1-yl]-1-thiophen-2-ylpropyl]carbamate; hydrochloride The procedure given in Example 53 was followed using 4-amino-5-chloro-N-[[1-(3-hydroxy-3-thiophen-2-ylpropyl)piperidin-4-yl]methyl]-2-methoxybenzamide from Example 48 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ8.1 (s, 1H), 7.8 (m, 1H), 7.3 (m, 1H), 7.1-6.9 (m, 2H), 6.35 (s, 1H), 4.75 (s, 2H), 4.4 (s, 2H), 3.9 (s, 3H), 3.35 (m, 2H), 3.1 (m, 2H), 2.55 (m, 1H), 2.5-2.0 (m, 5H), 1.9-1.2 (m, 5H)

Example 65

[4-[4-[[(4-amino-5-chloro-2-methoxybenzoyl)amino]methyl]piperidin-1-yl]-1-(4-fluorophenyl)butan-2-yl]carbamate; hydrochloride The procedure given in Example 53 was followed using 4-amino-5-chloro-N-[[1-[4-(4-fluorophenyl)-3-hydroxybutyl]piperidin-4-yl]methyl]-2-methoxybenzamide from Example 51 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ 8.1 (s, 1H), 7.75 (m, 1H), 7.15 (m, 2H), 7.0 (m, 2H), 6.3 (s, 1H), 4.9 (m, 1H), 4.8 (s, 2H), 4.5 (s, 2H), 3.85 (s, 3H), 3.3 (m, 2H), 2.9-2.8 (m, 4H), 2.4 (m, 2H), 1.9 (m, 2H), 1.8-1.5 (m, 5H), 1.3 (m, 2H)

Example 66

[1-[4-[[(4-amino-5-chloro-2-methoxybenzoyl)amino]methyl]piperidin-1-yl]-5-(4-fluorophenyl)pentan-3-yl]carbamate hydrochloride The procedure given in Example 53 was followed using 4-amino-5-chloro-N-[[1-[5-(4-fluorophenyl)-3-hydroxypentyl]piperidin-4-yl]methyl]-2-methoxybenzamide from Example 52 as a reactant, instead of 4-amino-5-chloro-N-[[1-(3-hydroxy-3-phenylpropyl)piperidin-4-yl]methyl]-2-methoxybenzamide, to give the title compound.

1H-NMR (CDCl3, 200 MHz) δ 8.1 (s, 1H), 7.75 (m, 1H), 7.15 (m, 2H), 6.95 (m, 2H), 6.3 (s, 1H), 4.8 (m, 1H), 4.75 (s, 2H), 4.45 (s, 2H), 3.85 (s, 3H), 3.35 (m, 2H), 2.95 (m, 2H), 2.65 (m, 2H), 2.4 (m, 2H), 2.0-1.5 (m, 9H), 1.3 (m, 2H)

Example 67

(S)-4-amino-5-chloro-N-[[1-[3-(4-fluorophenyl)-3-hydroxypropyl]piperidin-4-yl]methyl]-2-methoxybenzamide; hydrochloride A solution of 3-Chloro-4'-fluoropropiophenone (5.4 mmol) was slowly added to 1.6M solution of (−)-chlorodiisopinocampheylborane in Hexane (8.1 mmol) at −25° C. This reaction mixture was stirred at room temperature for 16 h. After 16 h stirring at −25° C., MeOH was added to terminate the reaction, then it was washed with brine, and the resulting organic layer was dried and concentrated in vacuo. The crude product was dissolved in 20 mL of acetonitrile and was added 4-amino-5-chloro-2-methoxy-N-[(piperidin-4-yl)methyl]benzamide (3.6 mmol), potassium carbonate (5.4 mmol), and potassium iodide (5.4 mmol) at 25° C. The reaction mixture was refluxed for 12 h. This solution was then concentrated on a rotary evaporator and diluted with ethylacetate, washed with brine, the resulting organic layer was dried and purified by column chromatography. The resulting (S)-4-amino-5-chloro-N-[[1-[3-(4-fluorophenyl)-3-hydroxypropyl]piperidin-4-yl]methyl]-2-methoxybenzamide was dissolved in MC and the solution treated with a solution of HCl in ether. The resulting precipitate was filtered to give the title compound.

1H-NMR (CDCl3, 200 MHz) δ8.1 (s, 1H), 7.8 (m, 1H), 7.4-7.3 (m, 2H), 7.1-7.0 (m, 2H), 6.35 (s, 1H), 4.9 (m, 1H), 4.4 (s, 2H), 3.9 (s, 3H), 3.4-3.1 (m, 4H), 2.9-2.7 (m, 2H), 2.4-2.0 (m, 2H), 1.9-1.7 (m, 5H), 1.7-1.5 (m, 2H)

Example 68

(S)-[3-[4-[[(4-amino-5-chloro-2-methoxybenzoyl)amino]methyl]piperidin-1-yl]-1-(4-fluorophenyl)propyl]carbamate; hydrochloride (S)-4-amino-5-chloro-N-[[1-[3-(4-fluorophenyl)-3-hydroxypropyl]piperidin-4-yl]methyl]-2-methoxybenzamide (1.5 mmol) from Example 62 was dissolved in 10 mL of THF and added with 1,1'-carbonyldiimidazole (12 mmol) at 0° C. The reaction mixture was stirred at room temperature for 4 h, followed by the addition of excess ammonium hydroxide (3 ml) at 0° C. After 2 h stirring at room temperature, water was added to terminate the reaction. The organic layer was extracted 3 times with dichloromethane, dried, and concentrated in vacuo. The resulting (S)-[3-[4-[[(4-amino-5-chloro-2-methoxybenzoyl)amino]methyl]piperidin-1-yl]-1-(4-fluorophenyl)propyl]carbamate was dissolved in MC and the solution was treated with a solution of HCl in ether. The resulting precipitate was filtered to give the title compound.

1H-NMR (CDCl3, 200 MHz) δ8.1 (s, 1H), 7.8 (m, 1H), 7.4-7.2 (m, 2H), 7.1-7.0 (m, 2H), 6.3 (s, 1H), 5.7 (m, 1H), 4.6 (m, 2H), 4.4 (s, 2H), 3.9 (s, 3H), 3.4-3.1 (m, 4H), 2.8-2.6 (m, 2H), 2.3-2.0 (m, 2H), 2.0-1.6 (m, 5H), 1.5-1.3 (m, 2H)

Example 69

(R)-4-amino-5-chloro-N-[[1-[3-(4-fluorophenyl)-3-hydroxypropyl]piperidin-4-yl]methyl]-2-methoxy-benzamide; hydrochloride The procedure given in Example 67 was followed using (+)-chlorodiisopinocampheylborane as a reactant, instead of (−)-chlorodiisopinocampheylborane, to give the title compound.

1H-NMR (CDCl3, 200 MHz) δ8.1 (s, 1H), 7.8 (m, 1H), 7.4-7.3 (m, 2H), 7.1-7.0 (m, 2H), 6.35 (s, 1H), 4.9 (m, 1H), 4.4 (s, 2H), 3.9 (s, 3H), 3.4-3.1 (m, 4H), 2.9-2.7 (m, 2H), 2.4-2.0 (m, 2H), 1.9-1.7 (m, 5H), 1.7-1.5 (m, 2H)

Example 70

(R)-[3-[4-[[(4-amino-5-chloro-2-methoxybenzoyl)amino]methyl]piperidin-1-yl]-1-(4-fluorophenyl)propyl]carbamate; hydrochloride The procedure given in Example 68 was followed using (R)-4-amino-5-chloro-N-[[1-[3-(4-fluorophenyl)-3-hydroxypropyl]piperidin-4-yl]methyl]-2-methoxybenzamide as a reactant, instead of (S)-4-amino-5-chloro-N-[[1-[3-(4-fluorophenyl)-3-hydroxypropyl]piperidin-4-yl]methyl]-2-methoxybenzamide, to give the title compound 1H-NMR (CDCl3, 200 MHz) δ8.15 (m, 1H), 7.8 (m, 1H), 7.4-7.3 (m, 4H), 6.35 (s, 1H), 4.9 (m, 2H), 4.4 (s, 2H), 3.9 (s, 3H), 3.4 (m, 2H), 3.3-3.1 (m, 2H), 2.7 (m, 2H), 2.2 (m, 1H), 2.1-1.6 (m, 6H), 1.5-1.3 (m, 2H)

Example 71

4-amino-5-chloro-N-[[1-(2-hydroxy-3-phenoxypropyl)piperidin-4-yl]methyl]-2-methoxybenzamide; hydrochloride A mixture of 4-amino-5-chloro-2-methoxy-N-[(piperidin-4-yl)methyl]benzamide (3 mmol) and 1,2-epoxy-3-phenoxypropane (3 mmol) was refluxed in 10 mL of isopropanol for 3 h. This solution was concentrated on a rotary evaporator and the mixture was purified by column chromatography. The resulting 4-amino-5-chloro-N-((1-(2-hydroxy-3-phenoxypropyl)piperidin-4-yl)methyl)-2-methoxybenzamide was dissolved in MC and the solution treated with a solution of HCl in ether. The resulting precipitate was filtered to give the title compound.

1H NMR (DMSO, 200 MHz), ppm (δ): (HCl salt form) 9.75 (br, 1H), 8.0 (m, 1H), 7.66 (s, 1H), 7.30 (m, 2H), 6.96 (m, 3H), 6.48 (s, 1H), 5.96 (s, 2H), 4.35 (m, 1H), 3.95 (m, 2H), 3.83 (m, 3H), 3.54 (m, 2H), 3.17 (m, 4H), 3.0 (m, 2H), 1.9-1.5 (m, 5H)

Example 72

4-amino-5-chloro-N-[[1-[3-(4-fluorophenoxy)-2-hydroxypropyl]piperidin-4-yl]methyl]-2-methoxy-benzamide; hydrochloride The procedure given in Example 71 was followed using 4-fluorophenyl glycidyl ether as a reactant, instead of 1,2-epoxy-3-phenoxypropane, to give the title compound.

1H NMR (DMSO, 500 MHz), ppm (δ): (HCl salt form) 9.3 (m, 1H), 8.0 (s, 1H), 7.67 (s, 1H), 7.13 (m, 2H), 6.96 (m, 2H), 6.48 (s, 1H), 5.93 (s, 2H), 4.3 (m, 1H), 3.92 (s, 2H), 3.83 (s, 3H), 3.55 (m, 2H), 3.3-3.2 (m, 4H), 3.0 (m, 2H), 1.77 (m, 3H), 1.6 (m, 1H), 1.5 (m, 1H)

Example 73

4-amino-5-chloro-N-[[1-[3-(4-chlorophenoxy)-2-hydroxypropyl]piperidin-4-yl]methyl]-2-methoxy-benzamide; hydrochloride The procedure given in Example 71 was followed using 4-chlorophenyl glycidyl ether as a reactant, instead of 1,2-epoxy-3-phenoxypropane, to give the title compound.

1H NMR (DMSO, 200 MHz), ppm (δ): (free amine form) 7.9 (m, 1H), 7.65 (s, 1H), 7.3 (m, 2H), 6.95 (m, 2H), 6.46 (s, 1H), 5.93 (s, 2H), 4.85 (m, 1H), 4.0-3.8 (m, 5H), 3.3-3.1 (m, 4H), 2.9 (m, 2H), 2.4 (m, 1H), 2.0 (m, 2H), 1.7-1.4 (m, 3H), 1.2 (m, 2H)

Example 74

4-amino-5-chloro-N-[[1-[2-hydroxy-3-(4-methoxyphenoxy)propyl]piperidin-4-yl]methyl]-2-methoxy-benzamide; hydrochloride The procedure given in Example 71 was followed using glycidyl 4-methoxyphenyl ether as a reactant, instead of 1,2-epoxy-3-phenoxypropane, to give the title compound.

1H NMR (DMSO, 500 MHz), ppm (δ): (HCl salt form) 9.4 (m, 1H), 8.00 (m, 1H), 7.67 (s, 1H), 6.86 (m, 4H), 6.48 (m, 1H), 5.91 (m, 2H), 4.29 (m, 1H), 3.9) m, 2H), 3.83 (s, 3H), 3.52 (m, 2H), 3.21 (m, 4H), 2.90 (m, 2H), 1.75 (m, 3H), 1.56 (m, 1H), 1.47 (m, 1H)

Example 75

4-amino-5-chloro-N-[[1-[3-(2,3-dichlorophenoxy)-2-hydroxypropyl]piperidin-4-yl]methyl]-2-methoxy-benzamide; hydrochloride The procedure given in Example 71 was followed using 2,3-dichlorophenyl glycidyl ether as a reactant, instead of 1,2-epoxy-3-phenoxypropane, to give the title compound.

1H-NMR (CDCl3, 200 MHz) δ8.1 (s, 1H), 7.9-7.85 (m, 1H), 7.25 (s, 1H), 7.20-7.05 (m, 2H), 6.95 (m, 1H), 6.35 (s, 1H), 4.4 (m, 2H), 4.2 (m, 1H), 4.05 (m, 2H), 3.9 (s, 3H), 3.3 (m, 2H), 3.1 (m, 1H), 3.0 (m, 1H), 2.7 (m, 2H), 2.4 (m, 1H), 2.2 (m, 1H), 1.97-1.8 (m, 3H), 1.6-1.4 (m, 2H)

Example 76

4-amino-5-chloro-N-[[1-[3-(2,4-dichlorophenoxy)-2-hydroxypropyl]piperidin-4-yl]methyl]-2-methoxy-benzamide; hydrochloride The procedure given in Example 71 was followed using 2,4-dichlorophenyl glycidyl ether as a reactant, instead of 1,2-epoxy-3-phenoxypropane, to give the title compound.

1H-NMR (CDCl3, 200 MHz) (s, 1H), 7.9-7.85 (m, 1H), 7.4 (s, 1H), 7.20 (m, 1H), 6.9 (m, 1H), 6.35 (s, 1H), 4.4 (m, 2H), 4.2 (m, 1H), 4.05 (m, 2H), 3.9 (s, 3H), 3.4 (m, 2H), 3.1 (m, 1H), 2.9 (m, 1H), 2.65 (m, 2H), 2.4 (m, 1H), 2.1 (m, 1H), 1.9-1.65 (m, 3H), 1.6-1.25 (m, 2H)

Example 77

4-amino-5-chloro-N-[[1-[3-(2,5-dichlorophenoxy)-2-hydroxypropyl]piperidin-4-yl]methyl]-2-methoxy-benzamide; hydrochloride The procedure given in Example 71 was followed using 2,5-dichlorophenyl glycidyl ether as a reactant, instead of 1,2-epoxy-3-phenoxypropane, to give the title compound.

1H-NMR (CDCl3, 200 MHz) δ8.1 (s, 1H), 7.8 (m, 1H), 7.3 (M, 1H), 6.95 (m, 2H), 6.3 (s, 1H), 4.4 (s, 2H), 4.2 (m, 1H), 4.0 (m, 2H), 3.9 (s, 3H), 3.4 (t, 2H), 3.1 (m, 1H), 2.9 (m, 1H), 2.6 (t, 2H), 2.4 (m, 1H), 2.1 (m, 1H), 1.9-1.8 (m, 3H), 1.5-1.3 (m, 2H)

Example 78

4-amino-5-chloro-N-[[1-[3-(2,6-dichlorophenoxy)-2-hydroxypropyl]piperidin-4-yl]methyl]-2-methoxy-benzamide; hydrochloride The procedure given in Example 71 was followed using 2,6-dichlorophenyl glycidyl ether as a reactant, instead of 1,2-epoxy-3-phenoxypropane, to give the title compound.

1H-NMR (CDCl3, 200 MHz) δ8.8 (m, 1H), 8.1 (s, 1H), 7.3 (2H), 7.0 (t, 1H), 6.35 (s, 1H), 4.4 (s, 2H), 4.2 (s, 1H), 4.1 (t, 2H), 3.95 (s, 3H), 3.4 (t, 2H), 3.15 (m, 1H), 3.0 (m, 1H), 2.75 (m, 2H), 2.4 (m, 1H), 2.2 (m, 1H), 1.8 (m, 3H), 1.6-1.3 (m, 2H)

Example 79

4-amino-5-chloro-N-[[1-[3-(3,4-dichlorophenoxy)-2-hydroxypropyl]piperidin-4-yl]methyl]-2-methoxy-benzamide; hydrochloride The procedure given in Example 71 was followed using 3,4-dichlorophenyl glycidyl ether as a reactant, instead of 1,2-epoxy-3-phenoxypropane, to give the title compound.

1H-NMR (CDCl3, 200 MHz) δ 8.15 (m, 1H), 7.8 (m, 1H), 7.4-7.3 (m, 1H), 7.1 (m, 1H), 6.9 (m, 1H), 6.3 (m, 1H), 4.4 (s, 2H), 4.1 (m, 1H), 4.0-3.9 (m, 5H), 3.4 (m, 2H), 3.1 (m, 1H), 2.9 (m, 1H), 2.6 (m, 2H), 2.4 (m, 1H), 2.2-2.05 (m, 1H), 1.9-1.6 (m, 3H), 1.5-1.3 (m, 2H)

Example 80

4-amino-5-chloro-N-[[1-[3-(2-chlorophenoxy)-2-hydroxypropyl]piperidin-4-yl]methyl]-2-methoxy-benzamide; hydrochloride The procedure given in Example 71 was followed using 2-chlorophenyl glycidyl ether as a reactant, instead of 1,2-epoxy-3-phenoxypropane, to give the title compound.

1H-NMR (CDCl3, 200 MHz) δ8.1 (m, 1H), 7.8 (m, 1H), 7.4-7.2 (m, 2H), 7.0-6.9 (m, 2H), 6.9-6.8 (m, 1H), 6.4 (s, 1H), 4.5-4.4 (m, 2H), 43-4.1 (m, 3H), 3.9 (m, 3H), 3.4 (m, 2H), 3.1 (m, 1H0), 2.9 (m, 1H), 2.6 (m, 2H), 2.4 (m, 1H), 2.1 (m, 1H) 1.9-1.6 (m, 3H), 1.5-1.3 (m, 2H)

Example 81

4-amino-5-chloro-N-[[1-[3-(4-methylphenoxy)-2-hydroxypropyl]piperidin-4-yl]methyl]-2-methoxy-benzamide; hydrochloride The procedure given in Example 71 was followed using glycidyl 4-methylphenyl ether as a reactant, instead of 1,2-epoxy-3-phenoxypropane, to give the title compound.

1H-NMR (CDCl3, 200 MHz) δ 8.15 (m, 1H), 7.8 (m, 1H), 7.1 (m, 2H), 6.8 (m, 2H), 6.4 (s, 1H), 4.4 (m, 2H), 4.1 (m, 1H), 4.0-3.9 (m, 5H), 3.4 (m, 2H), 3.1 (m, 1H), 2.9 (m, 1H), 2.6 (m, 2H), 2.3 (m, 4H), 2.1 (m, 1H), 1.9-1.6 (m, 3H), 1.4 (m, 2H)

Example 82

4-amino-5-chloro-N-[[1-[3-(3,4-difluorophenoxy)-2-hydroxypropyl]piperidin-4-yl]methyl]-2-methoxy-benzamide; hydrochloride The procedure given in Example 71 was followed using 3,4-difluorophenyl glycidyl ether as a reactant, instead of 1,2-epoxy-3-phenoxypropane, to give the title compound.

1H-NMR (CDCl3, 200 MHz) δ8.15 (s, 1H), 7.8 (m, 1H), 7.2-7.0 (m, 1H), 6.9-6.6 (m, 2H), 6.35 (s, 1H), 4.4 (s, 2H), 4.1 (m, 1H), 3.9 (m, 5H), 3.4 (m, 2H), 3.1-2.9 (m, 2H), 2.6 (m, 2H), 2.4 (m, 1H), 2.1 (m, 1H), 1.9-1.6 (m, 3H), 1.5-1.3 (m, 2H)

Example 83

4-amino-5-chloro-N-[[1-[2-hydroxy-3-[4-(trifluoromethyl)phenoxy]propyl]piperidin-4-yl]methyl]-2-methoxybenzamide; hydrochloride The procedure given in Example 71 was followed using glycidyl 4-trifluoromethylphenyl ether as a reactant, instead of 1,2-epoxy-3-phenoxypropane, to give the title compound.

1H-NMR (CDCl3, 200 MHz) δ8.15 (s, 1H), 7.75 (m, 1H), 7.6-7.5 (m, 2H), 7.0 (m, 2H), 6.3 (s, 1H), 4.4 (s, 2H), 4.2-4.0 (m, 3H), 3.9 (s, 3H), 3.35 (m, 2H), 3.1 (m, 1H), 2.9 (m, 1H), 2.5 (m, 2H), 2.35 (m, 1H), 2.1 (m, 1H), 1.9-1.6 (m, 3H), 1.5-1.3 (m, 2H)

Example 84

4-amino-5-chloro-N-[[1-[2-hydroxy-3-(4-phenylphenoxy)propyl]piperidin-4-yl]methyl]-2-methoxybenzamide; hydrochloride The procedure given in Example 71 was followed using glycidyl 4-phenylphenyl ether as a reactant, instead of 1,2-epoxy-3-phenoxypropane, to give the title compound.

1H-NMR (CDCl3, 200 MHz) δ8.15 (s, 1H), 7.75 (m, 1H), 7.5-6.9 (m, 9H), 6.3 (s, 1H), 5.7 (m, 1H), 4.6 (m, 2H), 4.4 (s, 2H), 3.9 (s, 3H), 3.35 (m, 2H), 2.9 (m, 2H), 2.4-2.3 (m, 2H), 2.0-1.8 (m, 2H), 1.8-1.5 (m, 3H), 1.4-1.2 (m, 2H)

Example 85

4-amino-5-chloro-N-[[1-(2-hydroxy-3-naphthalen-2-yloxypropyl)piperidin-4-yl]methyl]-2-methoxybenzamide; hydrochloride The procedure given in Example 71 was followed using 2-(Naphthalen-2-yloxymethyl)-oxirane as a reactant, instead of 1,2-epoxy-3-phenoxypropane, to give the title compound.

1H-NMR (CDCl3, 200 MHz) δ 8.15 (s, 1H), 7.8 (m, 1H), 7.6-7.3 (m, 5H), 7.0 (m, 2H), 6.3 (s, 1H), 4.4 (s, 2H), 4.3 (m, 1H), 4.1-4.0 (m, 2H), 3.9 (s, 3H), 3.3 (m, 1H), 3.1 (m, 1H), 2.7 (m, 2H), 2.5 (m, 1H), 2.35 (m, 1H), 1.9-1.6 (m, 3H), 1.6-1.4 (m, 2H)

Example 86

4-amino-5-chloro-N-[[1-(2-hydroxy-3-phenylpropyl) piperidin-1-ium-4-yl]methyl]-2-methoxybenzamide; hydrochloride The procedure given in Example 71 was followed using (2,3-epoxypropyl)benzene as a reactant, instead of 1,2-epoxy-3-phenoxypropane, to give the title compound.

1H-NMR (CDCl3, 200 MHz) δ 8.1 (s, 1H), 7.8 (m, 1H), 7.3 (m, 5H), 6.35 (s, 1H), 4.45 (s, 2H), 4.0 (m, 1H), 3.95 (s, 3H), 3.35 (m, 2H), 3.05 (m, 1H), 2.9 (m, 2H), 2.7 (m, 1H), 2.5-2.3 (m, 3H), 2.0 (m, 1H), 1.8-1.6 (m, 3H), 1.4 (m, 2H)

Example 87

[1-[4-[[(4-amino-5-chloro-2-methoxybenzoyl) amino]methyl]piperidin-1-yl]-3-phenoxypropan-2-yl]carbamate; hydrochloride 4-amino-5-chloro-N-[[1-(2-hydroxy-3-phenoxypropyl) piperidin-4-yl]methyl]-2-methoxybenzamide (1 mmol) was dissolved in 10 mL of THF and added with 1,1'-carbonyl diimidazole (1.5 mmol) at 0° C. The reaction mixture was stirred at room temperature for 2 h, followed by the addition of excess ammonium hydroxide (3 mL) at room temperature. After 2 h stirring at room temperature, water was added to terminate the reaction. The organic layer was extracted 3 times with dichloromethane, dried, and concentrated in vacuo. The resulting carbamate was dissolved in MC and the solution treated with a solution of HCl in ether. The resulting precipitate was filtered to give the title compound.

1H NMR (DMSO, 200 MHz), ppm (δ): (HCl salt form)
8.0 (m, 1H), 7.66 (s, 1H), 7.29 (m, 2H), 6.96 (m, 2H), 6.90 (m, 1H), 6.48 (s, 1H), 5.98 (s, 2H), 5.35 (m, 1H), 4.15 (m, 2H), 3.83 (s, 3H), 3.3-2.1 (m, 6H), 3.0 (m, 2H), 1.78 (m, 3H), 1.5 (m, 2H)

Example 88

[1-[4-[[(4-amino-5-chloro-2-methoxybenzoyl) amino]methyl]piperidin-1-yl]-3-phenoxypropan-2-yl]piperidine-1-carboxylate; hydrochloride The title compound was obtained by the method described in Example 87, except using piperidine (2 mmol) instead of ammonium hydroxide.

1H NMR (DMSO, 200 MHz), ppm (δ): (HCl salt form)
9.95 (m, 1H), 8.05 (m, 1H), 7.66 (s, 1H), 7.31 (m, 2H), 6.96 (m, 3H), 6.48 (s, 1H), 6.0 (br, 2H), 5.4 (m, 1H), 4.2 (m, 2H), 3.83 (s, 3H), 3.7-3.4 (m, 6H), 3.18 (m, 4H), 3.0 (m, 2H), 1.77 (m, 3H), 1.7-1.3 (m, 8H)

Example 89

[1-[4-[[(4-amino-5-chloro-2-methoxybenzoyl) amino]methyl]piperidin-1-yl]-3-(4-fluorophenoxy) propan-2-yl]3,5-dimethylpiperidine-1-carboxylate; hydrochloride 4-amino-5-chloro-N-[[1-[3-(4-fluorophenoxy)-2-hydroxypropyl]piperidin-4-yl]methyl]-2-methoxybenzamide (1 mmol) was dissolved in 10 mL of THF and added with 1,1'-carbonyl diimidazole (1.5 mmol) at 0° C. The reaction mixture was stirred at room temperature for 2 h, followed by the addition of 3,5-dimethylpiperidine (2 mmol) at room temperature. After 2 h stirring at room temperature, water was added to terminate the reaction. The organic layer was extracted 3 times with dichloromethane, dried, and concentrated in vacuo. The resulting carbamate was dissolved in MC and the solution treated with a solution of HCl in ether. The resulting precipitate was filtered to give the title compound.

1H NMR (DMSO, 200 MHz), ppm (δ): (HCl salt form)
8.0 (s, 1H), 7.66 (s, 1H), 7.09 (m, 2H), 7.01 (m, 2H), 6.48 (s, 1H), 5.96 (s, 2H), 5.35 (br, 1H), 4.17 (s, 2H), 4.0-3.8 (m, 7H), 3.46 (m, 2H), 3.18 (m, 4H), 3.0 (m, 2H), 2.22 (m, 2H), 1.9-1.3 (m, 7H), 0.81 (m, 6H)

Example 90

[1-[4-[[(4-amino-5-chloro-2-methoxybenzoyl) amino]methyl]piperidin-1-yl]-3-(4-chlorophenoxy) propan-2-yl]3,5-dimethylpiperidine-1-carboxylate; hydrochloride The title compound was obtained by the method described in Example 89 except that 4-amino-5-chloro-N-[[1-[3-(4-chlorophenoxy)-2-hydroxypropyl]piperidin-4-yl]methyl]-2-methoxybenzamide was used as a starting material instead of 4-amino-5-chloro-N-[[1-[3-(4-fluorophenoxy)-2-hydroxypropyl]piperidin-4-yl]methyl]-2-methoxybenzamide.

1H NMR (DMSO, 200 MHz), ppm (δ): (HCl salt form)
10.1 (br, 1H), 8.0 (m, 1H), 7.66 (s, 1H), 7.34 (m, 2H), 7.00 (m, 2H), 6.48 (s, 1H), 5.96 (s, 2H), 5.35 (m, 1H), 4.2 (m, 2H), 4.0=3.7 (m, 7H), 3.6-3.4 (m, 2H), 3.18 (m, 4H), 3.0 (m, 2H), 2.2 (m, 2H), 1.9-1.2 (m, 7H), 0.9-0.6 (m, 6H)

Example 91

[1-[4-[[(4-amino-5-chloro-2-methoxybenzoyl) amino]methyl]piperidin-1-yl]-3-(4-methoxyphenoxy)propan-2-yl]carbamate; hydrochloride The procedure given in Example 87 was followed using 4-amino-5-chloro-N-[[1-[3-(4-methoxyphenoxy)-2-hydroxypropyl]piperidin-4-yl]methyl]-2-methoxybenzamide from Example 74 as a reactant, instead of 4-amino-5-chloro-N-[[1-(2-hydroxy-3-phenoxypropyl)piperidin-4-yl]methyl]-2-methoxybenzamide, to give the title compound.

1H NMR (DMSO, 200 MHz), ppm (δ): (HCl salt form)
9.95 (m, 1H), 8.0 (m, 1H), 7.66 (s, 1H), 6.88 (m, 6H), 6.48 (s, 1H), 5.35 (m, 1H), 4.07 (m, 2H), 3.83 (s, 3H), 3.69 (s, 3H), 3.6 (m, 2H), 3.25 (m, 5H), 3.0 (m, 2H), 2.0-1.5 (m, 5H)

Example 92

[1-[4-[[(4-amino-5-chloro-2-methoxybenzoyl) amino]methyl]piperidin-1-yl]-3-(2,3-dichlorophenoxy)propan-2-yl]carbamate; hydrochloride The procedure given in Example 87 was followed using 4-amino-5-chloro-N-[[1-[3-(2,3-dichlorophenoxy)-2-hydroxypropyl]piperidin-4-yl]methyl]-2-methoxybenzamide from Example 75 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ8.1 (s, 1H), 7.8 (m, 1H), 7.3 (m, 1H), 7.1 (m, 1H), 6.9 (m, 1H), 6.35 (s, 1H), 5.3 (m, 1H), 4.4 (m, 2H), 4.3 (m, 2H), 3.95 (m, 3H), 3.8 (m, 2H), 3.4 (m, 2H), 3.1 (m, 1H), 2.9 (m, 1H), 2.3-2.2 (m, 2H), 1.9-1.3 (m, 5H)

Example 93

[1-[4-[[(4-amino-5-chloro-2-methoxybenzoyl) amino]methyl]piperidin-1-yl]-3-(2,3-dichlorophenoxy)propan-2-yl]pyrrolidine-1-carboxylate; hydrochloride 4-amino-5-chloro-N-[[1-[3-(2,3-dichlorophenoxy)-2-hydroxypropyl]piperidin-4-yl]methyl]-2-methoxybenzamide (1 mmol) was dissolved in 10 mL of THF and added with 1,1'-carbonyl diimidazole (1.5 mmol) at 0° C. The reaction mixture was stirred at room temperature for 2 h, followed by the addition of pyrrolidine (2 mmol) at room temperature. After 2 h stirring at room temperature, water was added to terminate the reaction. The organic layer was extracted 3 times with dichloromethane, dried, and concentrated in vacuo. The resulting carbamate was dissolved in MC and the solution treated with a solution of HCl in ether. The resulting precipitate was filtered to give the title compound.

1H-NMR (CDCl3, 200 MHz) δ8.1 (s, 1H), 7.9 (m, 1H), 7.2-7.1 (m, 2H), 7.0-6.9 (m, 1H), 6.4 (s, 1H), 5.6 (m, 1H), 4.5-4.3 (m, 2H), 3.9 (m, 3H), 3.6 (m, 1H), 3.55-3.3 (m, 5H), 2.8 (m, 2H), 2.55 (m, 3H), 2.1 (m, 1H), 2.0-1.8 (m, 7H), 1.4-1.2 (m, 2H)

Example 94

[1-[4-[[(4-amino-5-chloro-2-methoxybenzoyl) amino]methyl]piperidin-1-yl]-3-(2,3-dichlorophenoxy)propan-2-yl]piperidine-1-carboxylate; hydrochloride The title compound was obtained by the method described in Example 93 except using piperidine instead of pyrrolidine.

1H-NMR (CDCl3, 200 MHz) δ8.1 (s, 1H), 7.3 (s, 1H), 7.2-7.1 (m, 2H), 7.0 (m, 1H), 6.4 (s, 1H), 5.6 (m, 1H), 4.5 (m, 1H), 4.3 (m, 1H), 3.9 (m, 3H), 33.6 (m, 1H), 3.5-3.3 (m, 5H), 2.9-2.7 (m, 2H), 2.5 (m, 4H), 2.2-1.9 (m, 4H), 1.8-1.5 (m, 7H)

Example 95

[1-[4-[[(4-amino-5-chloro-2-methoxybenzoyl) amino]methyl]piperidin-1-yl]-3-(2,3-dichlorophenoxy)propan-2-yl]azepane-1-carboxylate; hydrochloride The title compound was obtained by the method described in Example 93 except using hexamethyleneamine instead of pyrrolidine.

1H-NMR (CDCl3, 200 MHz) δ8.1 (s, 1H), 7.9 (m, 1H), 7.3 (m, 1H), 7.2-7.1 (m, 2H), 7.0-6.9 (m, 1H), 6.4 (s, 1H), 5.6 (m, 1H), 4.5 (m, 1H), 4.35 (m, 1H), 4.2-4.0 (m, 2H), 3.95 (s, 3H), 3.7-3.3 (m, 6H), 2.8 (m, 2H), 2.7-2.4 (m, 4H), 2.2-1.8 (m, 4H), 1.8-1.5 (m, 9H)

Example 96

[1-[4-[[(4-amino-5-chloro-2-methoxybenzoyl) amino]methyl]piperidin-1-yl]-3-(2,4-dichlorophenoxy)propan-2-yl]carbamate; hydrochloride The procedure given in Example 87 was followed using 4-amino-5-chloro-N-[[1-[3-(2,4-dichlorophenoxy)-2-hydroxypropyl]piperidin-4-yl]methyl]-2-methoxybenzamide from Example 76 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ8.1 (m, 1H), 7.9 (m, 1H), 7.4 (m, 1H), 7.1 (m, 1H), 6.9 (m, 1H), 6.35 (m, 1H), 5.2 (m, 1H), 4.8 (m, 2H), 4.4 (m, 2H), 4.2 (m, 2H), 3.9 (m, 3H), 3.4 (m, 2H), 3.0 (m, 2H), 2.75 (m, 2H), 2.2 (m, 2H), 1.9-1.5 (m, 3H), 1.5-1.3 (m, 2H)

Example 97

[1-[4-[[(4-amino-5-chloro-2-methoxybenzoyl) amino]methyl]piperidin-1-yl]-3-(2,5-dichlorophenoxy)propan-2-yl]carbamate; hydrochloride The procedure given in Example 87 was followed using 4-amino-5-chloro-N-[[1-[3-(2,5-dichlorophenoxy)-2-hydroxypropyl]piperidin-4-yl]methyl]-2-methoxybenzamide from Example 77 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ8.1 (m, 1H), 7.8 (m, 1H), 7.3 (m, 1H), 7.0-6.9 (m, 2H), 6.3 (m, 1H), 5.2 (m, 1H), 4.8 (m, 2H), 4.4 (m, 2H), 4.3-4.1 (m, 2H), 3.9 (m, 3H), 3.3 (m, 2H), 3.0 (m, 2H), 2.7 (m, 2H), 2.2 (m, 2H), 1.9-1.6 (m, 3H), 1.4-1.3 (m, 2H)

Example 98

[1-[4-[[(4-amino-5-chloro-2-methoxybenzoyl) amino]methyl]piperidin-1-yl]-3-(2,6-dichlorophenoxy)propan-2-yl]carbamate; hydrochloride The procedure given in Example 87 was followed using 4-amino-5-chloro-N-[[1-[3-(2,6-dichlorophenoxy)-2-hydroxypropyl]piperidin-4-yl]methyl]-2-methoxybenzamide from Example 78 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ 8.1 (m, 1H), 7.9 (m, 1H), 7.4 (m, 1H), 7.05 (m, 1H), 6.8 (m, 1H), 6.4 (m, 1H), 5.2 (m, 1H), 4.8 (s, 2H), 4.4 (s, 2H), 4.2 (m, 2H), 3.9 (m, 3H), 3.4 (m, 2H), 3.0 (m, 2H), 2.8 (m, 2H), 2.1 (m, 2H), 1.8-1.5 (m, 3H), 1.4-1.2 (m, 2H)

Example 99

[1-[4-[[(4-amino-5-chloro-2-methoxybenzoyl) amino]methyl]piperidin-1-yl]-3-(3,4-dichlorophenoxy)propan-2-yl]carbamate; hydrochloride The procedure given in Example 87 was followed using 4-amino-5-chloro-N-[[1-[3-(3,4-dichlorophenoxy)-2-hydroxypropyl]piperidin-4-yl]methyl]-2-methoxybenzamide from Example 79 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ8.1 (s, 1H), 7.9 (m, 1H), 7.4-7.3 (m, 1H), 7.1 (m, 1H), 6.9 (m, 1H), 6.35 (s, 1H), 5.2 (m, 1H), 4.8 (m 2H), 4.4 (m, 2H), 4.2-4.0 (m, 2H), 3.95 (s, 3H), 3.35 (m, 2H), 3.1-2.9 (m, 2H), 2.6 (m, 2H), 2.2-2.1 (m, 2H), 1.8-1.5 (m, 3H), 1.4-1.2 (m, 3H)

Example 100

[1-[4-[[(4-amino-5-chloro-2-methoxybenzoyl)amino]methyl]piperidin-1-yl]-3-[4-(trifluoromethyl)phenoxy]propan-2-yl]carbamate; hydrochloride The procedure given in Example 87 was followed using 4-amino-5-chloro-N-[[1-[2-hydroxy-3-[4-(trifluoromethyl)phenoxy]propyl]piperidin-4-yl]methyl]-2-methoxybenzamide from Example 83 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ 8.15 (s, 1H), 7.75 (m, 1H), 7.7-7.5 (m, 2H), 7.0 (m, 2H), 6.3 (s, 1H), 5.2 (m, 1H), 4.7 (m, 2H), 4.4 (s, 2H), 4.2 (m, 2H), 3.9 (s, 3H), 3.35 (m, 2H), 2.9 (m, 2H), 2.7-2.6 (m, 2H), 2.2-2.05 (m, 2H), 1.85 (m, 2H), 1.7 (m, 1H), 1.4-1.2 (m, 2H)

Example 101

[1-[4-[[(4-amino-5-chloro-2-methoxybenzoyl)amino]methyl]piperidin-1-yl]-3-(4-phenylphenoxy)propan-2-yl]carbamate; hydrochloride The procedure given in Example 87 was followed using 4-amino-5-chloro-N-[[1-[2-hydroxy-3-(4-phenylphenoxy)propyl]piperidin-4-yl]methyl]-2-methoxybenzamide from Example 84 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ 8.15 (s, 1H), 7.8-7.7 (m, 5H), 7.5-7.1 (m, 5H), 6.3 (s, 1H), 5.25 (m, 1H), 4.7 (m, 2H), 4.4-4.2 (m, 4H), 3.9 (s, 3H), 3.35 (m, 2H), 3.1-2.9 (m, 2H), 2.7 (m, 2H), 2.2-2.1 (m, 2H), 1.8-1.5 (m, 3H), 1.4-1.2 (m, 2H)

Example 102

[1-[4-[[(4-amino-5-chloro-2-methoxybenzoyl)amino]methyl]piperidin-1-yl]-3-naphthalen-2-yloxypropan-2-yl]carbamate; hydrochloride The procedure given in Example 87 was followed using 4-amino-5-chloro-N-[[1-(2-hydroxy-3-naphthalen-2-yloxypropyl)piperidin-4-yl]methyl]-2-methoxybenzamide from Example 85 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ 8.15 (s, 1H), 7.8 (m, 1H), 7.6-7.3 (m, 5H), 7.0 (m, 2H), 6.3 (s, 1H), 5.25 (m, 1H), 4.9-4.7 (br, 2H), 4.4 (s, 2H), 4.2 (m, 2H), 3.9 (s, 3H), 3.4-3.3 (m, 2H), 3.2-3.1 (m, 2H), 2.9-2.8 (m, 2H), 2.4-2.15 (m, 2H), 1.9-1.6 (m, 3H), 1.6-1.4 (m, 2H)

Example 103

[1-[4-[[(4-amino-5-chloro-2-methoxybenzoyl)amino]methyl]piperidin-1-yl]-3-phenylpropan-2-yl]carbamate; hydrochloride The procedure given in Example 87 was followed using 4-amino-5-chloro-N-[[1-(2-hydroxy-3-phenylpropyl)piperidin-1-ium-4-yl]methyl]-2-methoxybenzamide from Example 86 as a reactant, instead of 4-amino-5-chloro-N-[[1-(2-hydroxy-3-phenoxypropyl)piperidin-4-yl]methyl]-2-methoxybenzamide, to give the title compound.

1H-NMR (CDCl3, 200 MHz) δ 8.1 (s, 1H), 7.8 (m, 1H), 7.3-7.1 (m, 5H), 6.3 (s, 1H), 5.1 (m, 1H), 4.95 (s, 2H), 4.6 (s, 2H), 4.0 (m, 1H), 3.85 (s, 3H), 3.35 (m, 2H), 3.0-2.6 (m, 4H), 2.5-2.2 (m, 2H), 2.1-1.9 (m, 2H), 1.8-1.5 (m, 3H), 1.3 (m, 2H)

Example 104

N-[[1-(2-hydroxy-3-phenoxypropyl)piperidin-4-yl]methyl]-2-oxo-3-propan-2-ylbenzimidazole-1-carboxamide; hydrochloride A mixture of 3-isopropyl-2-oxo-2,3-dihydro-benzimidazole-1-carboxylic acid (piperidin-4-ylmethyl)-amide (3 mmol) and 1,2-epoxy-3-phenoxypropane (3 mmol) was refluxed in 10 mL of isopropanol for 3 h. This solution was concentrated on a rotary evaporator and the mixture was purified by column chromatography. The resulting N-[[1-(2-hydroxy-3-phenoxypropyl)piperidin-4-yl]methyl]-2-oxo-3-propan-2-ylbenzimidazole-1-carboxamide was dissolved in MC and the solution treated with a solution of HCl in ether. The resulting precipitate was filtered to give the title compound.

1H NMR (DMSO, 200 MHz), ppm (δ): (free amine form) 8.83 (m, 1H), 8.05 (m, 1H), 7.44 (m, 1H), 7.4-7.1 (m, 4H), 6.93 (m, 3H), 4.84 (m, 1H), 4.67 (m, 1H), 3.88 (m, 2H), 3.22 (m, 2H), 2.92 (m, 2H), 2.4 (m, 2H), 1.99 (m, 2H), 1.64 (m, 3H), 1.48 (m, 6H), 1.22 (m, 2H)

Example 105

N-[[1-[2-hydroxy-3-(4-nitrophenoxy)propyl]piperidin-4-yl]methyl]-2-oxo-3-propan-2-ylbenzimidazole-1-carboxamide; hydrochloride The procedure given in Example 104 was followed using glycidyl 4-nitrophenyl ether as a reactant, instead of 1,2-epoxy-3-phenoxypropane, to give the title compound.

1H-NMR (CDCl3, 200 MHz) δ 9.0 (m, 1H), 8.35-8.2 (m, 3H), 7.2 (m, 3H), 7.0 (m, 2H), 4.75 (m, 1H), 4.2-4.05 (m, 3H), 3.4 (t, 2H), 3.1 (m, 1H), 2.9 (m, 1H), 2.55 (m, 2H), 2.4 (m, 1H), 2.05 (m, 1H), 1.85 (m, 2H), 1.7 (m, 1H), 1.6 (d, 6H), 1.4 (m, 2H)

Example 106

N-[[1-[2-hydroxy-3-(4-methoxyphenoxy)propyl]piperidin-4-yl]methyl]-2-oxo-3-propan-2-ylbenzimidazole-1-carboxamide; hydrochloride The procedure given in Example 104 was followed using glycidyl 4-methoxyphenyl ether as a reactant, instead of 1,2-epoxy-3-phenoxypropane, to give the title compound.

1H NMR (DMSO, 200 MHz), ppm (δ): (free amine form) 8.83 (m, 1H), 8.07 (m, 1H), 7.44 (m, 1H), 7.15 (m, 2H), 6.85 (m, 4H), 4.78 (m, 1H), 4.66 (m, 1H), 3.91-3.77 (m, 2H), 3.68 (s, 3H), 3.22 (m, 2H), 2.87 (m, 2H), 2.36 (m, 2H), 1.96 (m, 2H), 1.60 (m, 2H), 1.48 (m, 7H), 1.23 (m, 2H)

Example 107

N-[[1-[3-(4-fluorophenoxy)-2-hydroxypropyl]piperidin-4-yl]methyl]-2-oxo-3-propan-2-ylbenzimidazole-1-carboxamide; hydrochloride The procedure given in Example 104 was followed using 4-fluorophenyl glycidyl ether as a reactant, instead of 1,2-epoxy-3-phenoxypropane, to give the title compound.

1H NMR (DMSO, 200 MHz), ppm (δ): (HCl salt form)
9.65 (m, 1H), 8.88 (m, 1H), 8.07 (m, 1H), 7.45 (m, 1H), 7.16 (m, 4H), 6.96 (m, 2H), 5.96 (m, 1H), 4.67 (m, 1H), 4.34 (m, 1H), 3.94 (m, 2H), 3.56 (m, 2H), 3.26 (m, 4H), 2.99 (m, 2H), 1.86 (m, 3H), 1.7-1.4 (m, 8H)

Example 108

N-[[1-[2-hydroxy-3-(2-methylphenoxy)propyl]piperidin-4-yl]methyl]-2-oxo-3-propan-2-ylbenzimidazole-1-carboxamide; hydrochloride The procedure given in Example 104 was followed using glycidyl 2-methylphenyl ether as a reactant, instead of 1,2-epoxy-3-phenoxypropane, to give the title compound.
1H NMR (DMSO, 200 MHz), ppm (δ): (HCl salt form)
9.3 (m, 1H), 8.87 (m, 1H), 8.07 (m, 1H), 7.45 (m, 1H), 7.18 (m, 5H), 6.90 (m, 2H), 5.94 (m, 1H), 4.7 (m, 1H), 4.35 (m, 1H), 3.95 (m, 2H), 3.59 (m, 2H), 3.4-2.8 (m, 6H), 2.18 (s, 3H), 1.87 (m, 3H), 1.7-1.4 (m, 8H)

Example 109

N-[[1-[3-(4-chlorophenoxy)-2-hydroxypropyl]piperidin-4-yl]methyl]-2-oxo-3-propan-2-ylbenzimidazole-1-carboxamide; hydrochloride The procedure given in Example 104 was followed using 4-chlorophenyl glycidyl ether as a reactant, instead of 1,2-epoxy-3-phenoxypropane, to give the title compound.
1H NMR (DMSO, 200 MHz), ppm (δ): (HCl salt form)
9.5 (m, 1H), 8.87 (m, 1H), 8.07 (m, 1H), 7.5-6.9 (m, 6H), 5.97 (m, 1H), 4.67 (m, 1H), 4.35 (m, 1H), 3.96 (m, 2H), 3.55 (m, 2H), 3.27 (m, 4H), 2.99 (m, 2H), 1.87 (m, 3H), 1.7-1.4 (m, 8H)

Example 110

N-[[1-[3-(4-tert-butylphenoxy)-2-hydroxypropyl]piperidin-4-yl]methyl]-2-oxo-3-propan-2-ylbenzimidazole-1-carboxamide; hydrochloride The procedure given in Example 104 was followed using 4-tert-butylphenyl glycidyl ether as a reactant, instead of 1,2-epoxy-3-phenoxypropane, to give the title compound.
1H NMR (DMSO, 200 MHz), ppm (δ): (HCl salt form)
9.32 (m, 1H), 8.87 (m, 1H), 8.07 (m, 1H), 7.45 (m, 1H), 7.29 (m, 1H), 7.19 (m, 1H), 6.87 (m, 2H), 5.95 (m, 1H), 4.65 (m, 1H), 4.29 (m, 1H), 3.93 (m, 2H), 3.54 (m, 2H), 3.5-3.1 (m, 4H), 2.99 (m, 2H), 1.87 (m, 3H), 1.7-1.47 (m, 8H), 1.25 (s, 9H)

Example 111

N-[[1-(2-hydroxy-3-phenoxypropyl)piperidin-4-yl]methyl]-3-methyl-2-oxobenzimidazole-1-carboxamide; hydrochloride The procedure given in Example 104 was followed using 3-methyl-2-oxo-2,3-dihydro-benzimidazole-1-carboxylic acid (piperidin-4-ylmethyl)-amide as a reactant, instead of 3-isopropyl-2-oxo-2,3-dihydro-benzimidazole-1-carboxylic acid (piperidin-4-ylmethyl)-amide, to give the title compound.
1H NMR (DMSO, 200 MHz), ppm (δ): (HCl salt form)
9.3 (m, 1H), 8.83 (m, 1H), 8.03 (m, 1H), 7.29-7.16 (m, 5H), 6.97 (m, 3H), 5.98 (m, 1H), 4.30 (m, 1H), 3.96 (m, 2H), 3.61 (m, 2H), 3.5-3.1 (m, 5H), 2.93 (m, 2H), 2.6 (m, 2H), 1.87 (m, 3H), 1.6 (m, 2H)

Example 112

N-[[1-[3-(4-chlorophenoxy)-2-hydroxypropyl]piperidin-4-yl]methyl]-3-methyl-2-oxobenzimidazole-1-carboxamide; hydrochloride The procedure given in Example 104 was followed using 3-methyl-2-oxo-2,3-dihydro-benzimidazole-1-carboxylic acid (piperidin-4-ylmethyl)-amide and 4-chlorophenyl glycidyl ether as a reactant, instead of 3-isopropyl-2-oxo-2,3-dihydro-benzimidazole-1-carboxylic acid (piperidin-4-ylmethyl)-amide and 1,2-epoxy-3-phenoxypropane, to give the title compound.
1H NMR (DMSO, 200 MHz), ppm (δ): (HCl salt form)
9.6 (m, 1H), 8.82 (m, 1H), 8.02 (m, 1H), 7.4-6.9 (m, 7H), 5.98 (m, 1H), 4.35 (m, 1H), 3.95 (m, 2H), 3.54 (m, 2H), 3.4-2.9 (m, 9H), 1.87 (m, 3H), 1.63 (m, 2H)

Example 113

N-[[1-[3-(4-tert-butylphenoxy)-2-hydroxypropyl]piperidin-4-yl]methyl]-3-methyl-2-oxobenzimidazole-1-carboxamide; hydrochloride The procedure given in Example 104 was followed using 3-methyl-2-oxo-2,3-dihydro-benzimidazole-1-carboxylic acid (piperidin-4-ylmethyl)-amide and 4-tert-butylphenyl glycidyl ether as a reactant, instead of 3-isopropyl-2-oxo-2,3-dihydro-benzimidazole-1-carboxylic acid (piperidin-4-ylmethyl)-amide and 1,2-epoxy-3-phenoxypropane, to give the title compound.
1H NMR (DMSO, 200 MHz), ppm (δ): (HCl salt form)
9.64 (m, 1H), 8.82 (m, 1H), 8.02 (m, 1H), 7.4-7.12 (m, 5H), 6.87 (m, 2H), 5.95 (m, 1H), 4.34 (m, 1H), 3.93 (m, 2H), 3.58 (m, 2H), 3.5-3.1 (m, 7H), 3.0 (m, 2H), 1.87 (m, 3H), 1.53 (m, 2H), 1.25 (s, 9H)

Example 114

N-[[1-[2-hydroxy-3-(4-methoxyphenoxy)propyl]piperidin-4-yl]methyl]-3-methyl-2-oxobenzimidazole-1-carboxamide; hydrochloride The procedure given in Example 104 was followed using 3-methyl-2-oxo-2,3-dihydro-benzimidazole-1-carboxylic acid (piperidin-4-ylmethyl)-amide and glycidyl 4-methoxyphenyl ether as a reactant, instead of 3-isopropyl-2-oxo-2,3-dihydro-benzimidazole-1-carboxylic acid (piperidin-4-ylmethyl)-amide and 1,2-epoxy-3-phenoxypropane, to give the title compound.
1H NMR (DMSO, 200 MHz), ppm (δ): (HCl salt form)
9.45 (m, 1H), 8.82 (m, 1H), 8.02 (m, 1H), 7.35-7.1 (m, 3H), 6.88 (m, 4H), 5.95 (m, 1H), 4.29 (m, 1H), 3.89 (m, 2H), 3.69 (s, 3H), 3.6-3.1 (m, 7H), 2.99 (m, 4H), 1.87 (m, 3H), 1.6 (m, 2H)

Example 115

N-[[1-[3-(4-fluorophenoxy)-2-hydroxypropyl]piperidin-4-yl]methyl]-3-methyl-2-oxobenzimidazole-1-carboxamide; hydrochloride The procedure given in Example 104 was followed using 3-methyl-2-oxo-2,3-dihydro-benzimidazole-1-carboxylic acid (piperidin-4-ylmethyl)-amide and 4-fluorophenyl glycidyl ether as a reactant, instead of 3-isopropyl-2-oxo-2,3-dihydro-benzimidazole-1-carboxylic acid (piperidin-4-ylmethyl)-amide and 1,2-epoxy-3-phenoxypropane, to give the title compound.

1H NMR (DMSO, 200 MHz), ppm (δ): (HCl salt form)
9.5 (m, 1H), 8.82 (m, 1H), 8.02 (m, 1H), 7.35-7.05 (m, 5H), 6.98 (m, 2H), 5.94 (m, 1H), 4.32 (m, 1H), 3.94 (m, 2H), 3.55 (m, 2H), 3.5-3.1 (m, 7H), 2.98 (m, 2H), 1.87 (m, 3H), 1.6 (m, 2H)

Example 116

3-ethyl-N-[[1-(2-hydroxy-3-phenoxypropyl)piperidin-4-yl]methyl]-2-oxobenzimidazole-1-carboxamide; hydrochloride The procedure given in Example 104 was followed using 3-ethyl-2-oxo-2,3-dihydro-benzimidazole-1-carboxylic acid (piperidin-4-ylmethyl)-amide as a reactant, instead of 3-isopropyl-2-oxo-2,3-dihydro-benzimidazole-1-carboxylic acid (piperidin-4-ylmethyl)-amide, to give the title compound.

1H-NMR (CDCl3, 200 MHz) δ 8.95 (m, 1H), 8.25 (m, 1H), 7.4-7.15 (m, 3H), 7.1-6.9 (m, 5H), 4.1 (m, 2H), 4.0 (m, 2H), 3.55 (m, 1H), 3.4 (t, 2H), 3.1 (m, 1H), 3.0 (m, 1H), 2.6 (m, 2H), 2.4 (m, 1H), 2.1 (m, 1H), 1.9-1.6 (m, 3H), 1.5-1.3 (m, 5H)

Example 117

3-ethyl-N-[[1-[2-hydroxy-3-(4-methoxyphenoxy)propyl]piperidin-4-yl]methyl]-2-oxobenzimidazole-1-carboxamide; hydrochloride The procedure given in Example 104 was followed using 3-ethyl-2-oxo-2,3-dihydro-benzimidazole-1-carboxylic acid (piperidin-4-ylmethyl)-amide and glycidyl 4-methoxyphenyl ether as a reactant, instead of 3-isopropyl-2-oxo-2,3-dihydro-benzimidazole-1-carboxylic acid (piperidin-4-ylmethyl)-amide and 1,2-epoxy-3-phenoxypropane, to give the title compound.

1H-NMR (CDCl3, 200 MHz) δ 8.95 (m, 1H), 8.2 (m, 1H), 7.3-7.0 (m, 3H), 6.8 (m, 4H), 4.25 (m, 1H), 4.0 (m, 4H), 3.8 (s, 3H), 3.5-3.3 (m, 4H), 2.9 (m, 2H), 2.6 (m, 1H), 2.4 (m, 1H), 1.9 (m, 2H), 1.8-1.6 (m, 3H), 1.4 (t, 3H)

Example 118

3-ethyl-N-[[1-[2-hydroxy-3-(2-methylphenoxy)propyl]piperidin-4-yl]methyl]-2-oxobenzimidazole-1-carboxamide; hydrochloride The procedure given in Example 104 was followed using 3-ethyl-2-oxo-2,3-dihydro-benzimidazole-1-carboxylic acid (piperidin-4-ylmethyl)-amide and glycidyl 2-methylphenyl ether as a reactant, instead of 3-isopropyl-2-oxo-2,3-dihydro-benzimidazole-1-carboxylic acid (piperidin-4-ylmethyl)-amide and 1,2-epoxy-3-phenoxypropane, to give the title compound.

1H-NMR (CDCl3, 200 MHz) δ 8.95 (m, 1H), 8.25 (m, 1H), 7.3-7.0 (m, 6H), 6.85 (m, 2H), 4.3-3.9 (m, 5H), 3.4 (m, 2H), 3.2 (m, 1H), 3.05 (m, 1H), 2.65 (m, 2H), 2.4 (m, 1H), 2.3 (s, 3H), 2.15 (m, 1H), 1.85 (m, 2H), 1.75 (m, 1H), 1.6-1.3 (m, 5H)

Example 119

N-[[1-[3-(4-chlorophenoxy)-2-hydroxypropyl]piperidin-4-yl]methyl]-3-ethyl-2-oxobenzimidazole-1-carboxamide; hydrochloride The procedure given in Example 104 was followed using 3-ethyl-2-oxo-2,3-dihydro-benzimidazole-1-carboxylic acid (piperidin-4-ylmethyl)-amide and 4-chlorophenyl glycidyl ether as a reactant, instead of 3-isopropyl-2-oxo-2,3-dihydro-benzimidazole-1-carboxylic acid (piperidin-4-ylmethyl)-amide and 1,2-epoxy-3-phenoxypropane, to give the title compound.

1H-NMR (CDCl3, 200 MHz) δ 8.95 (m, 1H), 8.25 (m, 1H), 7.2-7.0 (m, 4H), 7.05 (m, 1H), 6.9 (m, 2H), 4.2 (m, 1H), 4.0 (m, 4H), 3.4 (m, 2H), 3.2 (m, 1H), 3.05 (m, 1H), 2.65 (m, 2H), 2.4 (m, 1H), 2.0-1.7 (m, 3H), 1.6-1.3 (m, 5H)

Example 120

[1-[4-[[(2-oxo-3-propan-2-ylbenzimidazole-1-carbonyl)amino]methyl]piperidin-1-yl]-3-phenoxypropan-2-yl]carbamate:hydrochloride N-[[1-(2-hydroxy-3-phenoxypropyl)piperidin-4-yl]methyl]-2-oxo-3-propan-2-ylbenzimidazole-1-carboxamide (1 mmol) was dissolved in 10 mL of THF and added with 1,1'-carbonyl diimidazole (1.5 mmol) at 0° C. The reaction mixture was stirred at room temperature for 2 h, followed by the addition of excess ammonium hydroxide (3 mL) at room temperature. After 2 h stirring at room temperature, water was added to terminate the reaction. The organic layer was extracted 3 times with dichloromethane, dried, and concentrated in vacuo. The resulting carbamate was dissolved in MC and the solution treated with a solution of HCl in ether. The resulting precipitate was filtered to give the title compound.

1H NMR (DMSO, 200 MHz), ppm (δ): (HCl salt form)
10.2 (m, 1H), 8.88 (m, 1H), 8.07 (m, 1H), 7.6-6.8 (m, 10H), 5.34 (m, 1H), 4.66 (m, 1H), 4.15 (m, 2H), 3.55 (m, 2H), 3.26 (m, 4H), 3.04 (m, 2H), 1.85 (m, 3H), 1.59 (m, 2H), 1.48 (m, 6H)

Example 121

[1-(4-methoxyphenoxy)-3-[4-[[(2-oxo-3-propan-2-ylbenzimidazole-1-carbonyl)amino]methyl]piperidin-1-yl]propan-2-yl]carbamate; hydrochloride The procedure given in Example 120 was followed using N-[[1-[2-hydroxy-3-(4-methoxyphenoxy)propyl]piperidin-4-yl]methyl]-2-oxo-3-propan-2-ylbenzimidazole-1-carboxamide from Example 106 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.7 (m, 1H), 8.80 (m, 1H), 8.07 (m, 1H), 7.45 (m, 1H), 7.18 (m, 2H), 6.88 (m, 4H), 5.28 (m, 1H), 4.65 (m, 1H), 4.07 (s, 2H), 3.69 (s, 3H), 3.58 (m, 2H), 3.5-3.2 (m, 2H), 3.03 (m, 4H), 1.86 (m, 3H), 1.49 (m, 8H)

Example 122

[1-(4-fluorophenoxy)-3-[4-[[(2-oxo-3-propan-2-ylbenzimidazole-1-carbonyl)amino]methyl]piperidin-1-yl]propan-2-yl]carbamate; hydrochloride The procedure given in Example 120 was followed using N-[[1-[3-(4-fluorophenoxy)-2-hydroxypropyl]piperidin-4- yl]methyl]-2-oxo-3-propan-2-ylbenzimidazole-1-carboxamide from Example 107 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.5 (m, 1H), 8.88 (m, 1H), 8.07 (m, 1H), 7.45 (m, 1H), 7.16 (m, 4H), 7.0-6.8 (m, 4H), 5.31 (m, 1H), 4.66 (m, 1H), 4.11 (m, 2H), 3.60 (m, 2H), 3.5-3.2 (m, 4H), 3.00 (m, 2H), 1.87 (m, 3H), 1.7-1.4 (m, 8H)

Example 123

[1-(2-methylphenoxy)-3-[4-[[(2-oxo-3-propan-2-ylbenzimidazole-1-carbonyl)amino]methyl]piperidin-1-yl]propan-2-yl]carbamate; hydrochloride The procedure given in Example 120 was followed using N-[[1-[2-hydroxy-3-(2-methylphenoxy)propyl]piperidin-4-yl]methyl]-2-oxo-3-propan-2-ylbenzimidazole-1-carboxamide from Example 108 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.8 (m, 1H), 8.88 (m, 1H), 8.04 (m, 1H), 7.45 (m, 1H), 7.18 (m, 5H), 6.90 (m, 4H), 5.35 (m, 1H), 4.7 (m, 1H), 4.15 (m, 2H), 3.56 (m, 2H), 3.4-2.9 (m, 6H), 2.18 (s, 3H), 1.86 (m, 3H), 1.7-1.4 (m, 8H)

Example 124

[1-(4-chlorophenoxy)-3-[4-[[(2-oxo-3-propan-2-ylbenzimidazole-1-carbonyl)amino]methyl]piperidin-1-yl]propan-2-yl]carbamate; hydrochloride The procedure given in Example 120 was followed using N-[[1-[3-(4-chlorophenoxy)-2-hydroxypropyl]piperidin-4-yl]methyl]-2-oxo-3-propan-2-ylbenzimidazole-1-carboxamide from Example 109 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.35 (m, 1H), 8.88 (m, 1H), 8.07 (m, 1H), 7.5-6.9 (m, 9H), 5.3 (m, 1H), 4.65 (m, 1H), 4.13 (m, 2H), 3.60 (m, 2H), 3.0 (m, 4H), 2.84 (m, 2H), 1.87 (m, 3H), 1.7-1.1 (m, 8H)

Example 125

[1-(4-tert-butylphenoxy)-3-[4-[[(3-methyl-2-oxobenzimidazole-1-carbonyl)amino]methyl]piperidin-1-yl]propan-2-yl]carbamate; hydrochloride The procedure given in Example 120 was followed using N-[[1-[3-(4-tert-butylphenoxy)-2-hydroxypropyl]piperidin-4-yl]methyl]-2-oxo-3-propan-2-ylbenzimidazole-1-carboxamide from Example 110 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.64 (m, 1H), 8.82 (m, 1H), 8.02 (m, 1H), 7.3-7.1 (m, 5H), 6.87 (m, 4H), 5.35 (m, 1H), 4.1 (m, 2H), 3.58 (m, 2H), 3.5-3.1 (m, 7H), 3.0 (m, 2H), 1.87 (m, 3H), 1.53 (m, 2H), 1.25 (s, 9H)

Example 126

[1-[4-[[(3-methyl-2-oxobenzimidazole-1-carbonyl)amino]methyl]piperidin-1-yl]-3-phenoxypropan-2-yl]carbamate; hydrochloride The procedure given in Example 120 was followed using N-[[1-(2-hydroxy-3-phenoxypropyl)piperidin-4-yl]methyl]-3-methyl-2-oxobenzimidazole-1-carboxamide from Example 111 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.3 (m, 1H), 8.83 (m, 1H), 8.02 (m, 1H), 7.4-6.8 (m, 8H), 5.31 (m, 1H), 4.12 (m, 2H), 3.61 (m, 2H), 3.5-2.81 (m, 7H), 2.4-2.1 (m, 2H), 1.81 (m, 3H), 1.52 (m, 2H)

Example 127

[1-(4-chlorophenoxy)-3-[4-[[(3-methyl-2-oxobenzimidazole-1-carbonyl)amino]methyl]piperidin-1-yl]propan-2-yl]carbamate; hydrochloride The procedure given in Example 120 was followed using N-[[1-[3-(4-chlorophenoxy)-2-hydroxypropyl]piperidin-4-yl]methyl]-3-methyl-2-oxobenzimidazole-1-carboxamide from Example 112 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.5 (m, 1H), 8.83 (m, 1H), 8.02 (m, 1H), 7.4-6.9 (m, 7H), 6.87 (m, 2H), 5.3 (m, 1H), 4.14 (m, 2H), 3.6 (m, 2H), 3.4-3.1 (m, 5H), 3.0 (m, 4H), 1.87 (m, 3H), 1.63 (m, 2H)

Example 128

[1-(4-tert-butylphenoxy)-3-[4-[[(3-methyl-2-oxobenzimidazole-1-carbonyl)amino]methyl]piperidin-1-yl]propan-2-yl]carbamate; hydrochloride The procedure given in Example 120 was followed using N-[[1-[3-(4-tert-butylphenoxy)-2-hydroxypropyl]piperidin-4-yl]methyl]-3-methyl-2-oxobenzimidazole-1-carboxamide from Example 113 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H-NMR (DMSO-d6, 200 MHz, HCl form) δ 9.64 (m, 1H), 8.82 (m, 1H), 8.02 (m, 1H), 7.3-7.1 (m, 5H), 6.87 (m, 4H), 5.35 (m, 1H), 4.1 (m, 2H), 3.58 (m, 2H), 3.5-3.1 (m, 7H), 3.0 (m, 2H), 1.87 (m, 3H), 1.53 (m, 2H), 1.25 (s, 9H)

Example 129

[1-(4-methoxyphenoxy)-3-[4-[[(3-methyl-2-oxobenzimidazole-1-carbonyl)amino]methyl]piperidin-1-ium-1-yl]propan-2-yl]carbamate; hydrochloride The procedure given in Example 120 was followed using N-[[1-[2-hydroxy-3-(4-methoxyphenoxy)propyl]piperidin-4-yl]methyl]-3-methyl-2-oxobenzimidazole-1-carboxamide from Example 114 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form)
9.65 (m, 1H), 8.82 (m, 1H), 8.02 (m, 1H), 7.35-7.1 (m, 3H), 6.88 (m, 6H), 5.35 (m, 1H), 4.06 (m, 2H), 3.69 (s, 3H), 3.6-3.1 (m, 7H), 3.04 (m, 4H), 1.87 (m, 3H), 1.6 (m, 2H)

Example 130

[1-(4-fluorophenoxy)-3-[4-[[(3-methyl-2-oxobenzimidazole-1-carbonyl)amino]methyl]piperidin-1-yl]propan-2-yl]carbamate; hydrochloride The procedure given in Example 120 was followed using N-[[1-[3-(4-fluorophenoxy)-2-hydroxypropyl]piperidin-4-yl]methyl]-3-methyl-1-oxobenzimidazole-1-carboxamide from Example 115 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H NMR (DMSO, 200 MHz), ppm (δ): (HCl salt form) 9.45 (m, 1H), 8.83 (m, 1H), 8.02 (m, 1H), 7.35-7.05 (m, 5H), 6.99 (m, 2H), 6.88 (m, 2H), 5.35 (m, 1H), 4.11 (m, 2H), 3.60 (m, 2H), 3.5-3.1 (m, 7H), 3.04 (m, 2H), 1.87 (m, 3H), 1.49 (m, 2H)

Example 131

[1-[4-[[(3-ethyl-2-oxobenzimidazole-1-carbonyl)amino]methyl]piperidin-1-yl]-3-phenoxypropan-2-yl]carbamate; hydrochloride The procedure given in Example 120 was followed using 3-ethyl-N-[[1-(2-hydroxy-3-phenoxypropyl)piperidin-4-yl]methyl]-2-oxobenzimidazole-1-carboxamide from Example 116 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H-NMR (CDCl3, 200 MHz) δ 8.9 (m, 1H), 8.25 (m, 1H), 7.4-6.9 (m, 8H), 5.3 (s, 2H), 5.2 (m, 1H), 4.15 (m, 2H), 4.0 (m, 2H), 3.35 (t, 2H), 3.0 (m, 2H), 2.65 (m, 2H), 2.1 (m, 2H), 1.75 (m, 2H), 1.6 (m, 1H), 1.5-1.2 (m, 5H)

Example 132

[1-[4-[[(3-ethyl-2-oxobenzimidazole-1-carbonyl)amino]methyl]piperidin-1-ium-1-yl]-3-(4-methoxyphenoxy)propan-2-yl]carbamate; hydrochloride The procedure given in Example 120 was followed using 3-ethyl-N-[[1-[2-hydroxy-3-(4-methoxyphenoxy)propyl]piperidin-4-yl]methyl]-2-oxobenzimidazole-1-carboxamide from Example 117 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H-NMR (CDCl3, 200 MHz) δ 8.9 (m, 1H), 8.25 (m, 1H), 7.2 (m, 2H), 7.05 (m, 1H), 6.85 (m, 4H), 5.15 (m, 1H), 5.0 (s, 2H), 4.15 (m, 2H), 4.0 (m, 2H), 3.8 (s, 3H), 3.35 (t, 2H), 3.0 (m, 2H), 2.65 (m, 2H), 2.1 (m, 2H), 1.75 (m, 2H), 1.6 (m, 1H), 1.5-1.2 (m, 5H)

Example 133

[1-[4-[[(3-ethyl-2-oxobenzimidazole-1-carbonyl)amino]methyl]piperidin-1-yl]-3-(2-methylphenoxy)propan-2-yl]carbamate; hydrochloride The procedure given in Example 120 was followed using 3-ethyl-N-[[1-[2-hydroxy-3-(2-methylphenoxy)propyl]piperidin-4-yl]methyl]-2-oxobenzimidazole-1-carboxamide from Example 118 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H-NMR (CDCl3, 200 MHz) δ 8.9 (m, 1H), 8.25 (m, 1H), 7.3-7.0 (m, 5H), 6.85 (m, 2H), 5.25 (m, 1H), 5.05 (s, 2H), 4.15 (m, 2H), 4.0 (m, 2H), 3.35 (t, 2H), 3.0 (m, 2H), 2.7 (d, 2H), 2.2 (s, 3H), 2.1 (m, 2H), 1.8 (m, 2H), 1.6 (m, 1H), 1.5-1.2 (m, 5H)

Example 134

[1-(4-chlorophenoxy)-3-[4-[[(3-ethyl-2-oxobenzimidazole-1-carbonyl)amino]methyl]piperidin-1-yl]propan-2-yl]carbamate; hydrochloride The procedure given in Example 120 was followed using N-[[1-[3-(4-chlorophenoxy)-2-hydroxypropyl]piperidin-4-yl]methyl]-3-ethyl-2-oxobenzimidazole-1-carboxamide from Example 119 as a reactant, instead of N-[[1-(2-hydroxy-3-phenoxypropyl)piperidin-4-yl]methyl]-2-oxo-3-propan-2-ylbenzimidazole-1-carboxamide, to give the title compound.

1H-NMR (CDCl3, 200 MHz) δ 8.9 (m, 1H), 8.25 (m, 1H), 7.3-7.0 (m, 5H), 6.9 (m, 2H), 5.2 (m, 1H), 5.0 (s, 2H), 4.15 (m, 2H), 4.0 (m, 2H), 3.35 (t, 2H), 2.95 (m, 2H), 2.6 (d, 2H), 2.1 (m, 2H), 1.75 (m, 2H), 1.6 (m, 1H), 1.5-1.2 (m, 5H)

Example 135

3-cyclopropyl-N-[[1-(3-hydroxy-3-phenylpropyl)piperidin-4-yl]methyl]-2-oxobenzimidazole-1-carboxamide; hydrochloride A mixture of 3-cyclopropyl-2-oxo-2,3-dihydro-benzimidazole-1-carboxylic acid (piperidin-4-ylmethyl)-amide (5.0 mmol), 3-chloropropiophenone (6.0 mmol), potassium carbonate (7.6 mmol) and potassium iodide (7.6 mmol) was refluxed in 15 mL of acetonitrile for 12 h. This solution was then concentrated on a rotary evaporator and diluted with ethyl acetate. This mixture was then washed with brine, and the resulting organic layer was dried and purified by column chromatography. This was dissolved in ethanol (10 mL) and was added with sodium borohydride (10.0 mmol) at 0° C. and stirred at 25° C. for 2 h. This solution was concentrated on a rotary evaporator and diluted with ethylacetate. This mixture was washed with brine, dried, and concentrated in vacuo. The residue was purified by column chromatography. The resulting 3-cyclopropyl-N-[[1-(3-hydroxy-3-phenylpropyl)piperidin-4-yl]methyl]-2-oxobenzimidazole-1-carboxamide was dissolved in MC and the solution treated with a solution of HCl in ether. The resulting precipitate was filtered to give the title compound.

1H-NMR (CDCl3, 200 MHz) δ 8.95 (m, 1H), 8.35 (m, 1H), 7.5-7.1 (m, 9H), 4.95 (m, 1H), 3.35-3.1 (m, 4H), 2.9 (m, 1H), 2.7 (m, 2H), 2.2 (m, 1H), 2.1-1.6 (m, 5H), 1.5 (m, 2H), 1.3-1.0 (m, 5H)

Example 136

N-[[1-(3-hydroxy-3-phenylpropyl)piperidin-4-yl]methyl]-2-oxo-3-propan-2-ylbenzimidazole-1-carboxamide; hydrochloride The procedure given in Example 135 was followed using 3-isopropyl-2-oxo-2,3-dihydro-benzimidazole-1-carboxylic acid (piperidin-4-ylmethyl)-amide as a reactant, instead of 3-cyclopropyl-2-oxo-2,3-dihydro-benzimidazole-1-carboxylic acid (piperidin-4-ylmethyl)-amide, to give the title compound.

1H-NMR (CDCl3, 200 MHz) δ 9.0 (m, 1H), 8.25 (m, 1H), 7.5-7.1 (m, 9H), 4.95 (m, 1H), 4.75 (m, 1H), 3.35 (m, 2H), 3.15 (m, 2H), 2.8-2.55 (m, 2H), 2.1 (m, 1H), 1.9 (m, 4H), 1.8-1.4 (m, 10H)

Example 137

N-[[1-[3-(4-fluorophenyl)-3-hydroxypropyl]piperidin-1-ium-4-yl]methyl]-2-oxo-3-propan-2-ylbenzimidazole-1-carboxamide; hydrochloride The procedure given in Example 135 was followed using 3-isopropyl-2-oxo-2,3-dihydro-benzimidazole-1-carboxylic acid (piperidin-4-ylmethyl)-amide and 3-chloro-4'-fluoropropiophenone as a reactant, instead of 3-cyclopropyl-2-oxo-2,3-dihydro-benzimidazole-1-carboxylic acid (piperidin-4-ylmethyl)-amide and 3-chloropropiophenone, to give the title compound.

1H-NMR (CDCl3, 500 MHz) δ 9.00 (m, 1H), 8.28 (s, 1H), 7.36 (m, 2H), 7.20 (m, 3H), 7.03 (m, 2H), 4.95 (m, 1H), 4.72 (m, 1H), 3.37 (m, 2H), 3.35 (m, 1H), 3.22 (m, 1H), 2.81 (m, 1H), 2.71 (m, 1H), 2.28 (m, 1H), 2.11 (m, 1H), 1.93 (m, 4H), 1.79 (m, 1H), 1.58 (m, 8H)

Example 138

3-cyclopropyl-N-[[1-[3-(4-fluorophenyl)-3-hydroxypropyl]piperidin-1-ium-4-yl]methyl]-2-oxobenzimidazole-1-carboxamide; hydrochloride The procedure given in Example 135 was followed using 3-chloro-4'-fluoropropiophenone as a reactant, instead of 3-chloropropiophenone, to give the title compound.

1H-NMR (CDCl3, 500 MHz) δ 9.00 (m, 1H), 8.20 (s, 1H), 7.36 (m, 2H), 7.20 (m, 3H), 7.05 (m, 2H), 4.96 (m, 1H), 3.37 (m, 3H), 3.30 (m, 1H), 2.92 (m, 2H), 2.80 (m, 1H), 2.35 (m, 1H), 2.2 (m, 1H), 1.96 (m, 2H), 1.79 (m, 2H), 1.65 (m, 3H), 1.20 (m, 2H), 1.05 (m, 2H)

Example 139

N-[[1-[3-(4-chlorophenyl)-3-hydroxypropyl]piperidin-1-ium-4-yl]methyl]-2-oxo-3-propan-2-ylbenzimidazole-1-carboxamide; hydrochloride The procedure given in Example 135 was followed using 3-isopropyl-2-oxo-2,3-dihydro-benzimidazole-1-carboxylic acid (piperidin-4-ylmethyl)-amide and 3-chloro-4'-chloropropiophenone as a reactant, instead of 3-cyclopropyl-2-oxo-2,3-dihydro-benzimidazole-1-carboxylic acid (piperidin-4-ylmethyl)-amide and 3-chloropropiophenone, to give the title compound.

1H-NMR (CDCl3, 500 MHz) δ 9.00 (m, 1H), 8.27 (m, 1H), 7.33 (m, 4H), 7.18 (m, 3H), 4.96 (m, 1H), 4.72 (m, 1H), 3.37 (m, 3H), 3.25 (m, 1H), 2.87-2.70 (m, 2H), 2.40 (m, 1H), 2.13 (m, 1H), 1.95 (m, 5H), 1.78 (m, 2H), 1.58 (m, 6H)

Example 140

N-[[1-[3-(4-chlorophenyl)-3-hydroxypropyl]piperidin-1-ium-4-yl]methyl]-3-cyclopropyl-2-oxobenzimidazole-1-carboxamide; hydrochloride The procedure given in Example 135 was followed using 3-chloro-4'-chloropropiophenone as a reactant, instead of 3-chloropropiophenone, to give the title compound.

1H-NMR (CDCl3, 500 MHz) δ 8.94 (m, 1H), 8.20 (m, 1H), 7.33-7.19 (m, 7H), 4.96 (m, 1H), 3.37 (m, 3H), 3.26 (m, 1H), 2.91 (m, 2H), 2.81 (m, 1H), 2.32 (m, 1H), 2.15 (m, 1H), 1.95 (m, 4H), 1.77 (m, 2H), 1.62 (m, 3H), 1.18 (m, 2H), 1.05 (m, 2H)

Example 141

N-[[1-[3-hydroxy-3-(4-methylphenyl)propyl]piperidin-1-ium-4-yl]methyl]-2-oxo-3-propan-2-ylbenzimidazole-1-carboxamide; hydrochloride The procedure given in Example 135 was followed using 3-isopropyl-2-oxo-2,3-dihydro-benzimidazole-1-carboxylic acid (piperidin-4-ylmethyl)-amide and 3-chloro-4'-methylpropiophenone as a reactant, instead of 3-cyclopropyl-2-oxo-2,3-dihydro-benzimidazole-1-carboxylic acid (piperidin-4-ylmethyl)-amide and 3-chloropropiophenone, to give the title compound.

1H-NMR (CDCl3, 500 MHz) δ 9.01 (m, 1H), 8.26 (m, 1H), 7.37-7.15 (m, 7H), 4.95 (m, 1H), 4.75 (m, 1H), 3.38 (m, 4H), 2.90 (m, 2H), 2.36 (s, 3H), 2.10-1.65 (m, 9H), 1.60 (m, 6H)

Example 142

3-cyclopropyl-N-[[1-[3-hydroxy-3-(4-methylphenyl)propyl]piperidin-1-ium-4-yl]methyl]-2-oxobenzimidazole-1-carboxamide; hydrochloride The procedure given in Example 135 was followed using 3-chloro-4'-methylpropiophenone as a reactant, instead of 3-chloropropiophenone, to give the title compound.

1H-NMR (CDCl3, 500 MHz) δ 8.95 (m, 1H), 8.20 (m, 1H), 7.42-7.13 (m, 7H), 4.75 (m, 1H), 3.42-3.20 (m, 4H), 2.90 (m, 1H), 2.81 (m, 2H), 2.32 (m, 3H), 2.18 (m, 1H), 1.95 (m, 3H), 1.80 (m, 2H), 1.65 (m, 3H), 1.20 (m, 2H), 1.06 (m, 2H)

Example 143

N-[[1-[3-hydroxy-3-(4-methoxyphenyl)propyl]piperidin-1-ium-4-yl]methyl]-2-oxo-3-propan-2-ylbenzimidazole-1-carboxamide; hydrochloride The procedure given in Example 135 was followed using 3-isopropyl-2-oxo-2,3-dihydro-benzimidazole-1-carboxylic acid (piperidin-4-ylmethyl)-amide and 3-chloro-4'-methoxypropiophenone as a reactant, instead of 3-cyclopropyl-2-oxo-2,3-dihydro-benzimidazole-1-carboxylic acid (piperidin-4-ylmethyl)-amide and 3-chloropropiophenone, to give the title compound.

1H-NMR (CDCl3, 200 MHz) δ 9.05 (m, 1H), 8.25 (m, 1H), 7.35 (m, 3H), 7.2 (m, 3H), 6.9 (m, 2H), 6.85 (m, 1H), 5.0 (m, 1H), 4.7 (m, 1H), 3.85 (s, 3H), 3.7 (m, 1H), 3.5 (m, 1H), 3.4 (m, 2H), 3.25 (m, 2H), 3.0 (m, 3H), 2.65 (m, 2H), 2.3 (m, 2H), 2.1 (m, 2H), 1.6 (m, 6H)

Example 144

3-cyclopropyl-N-[[1-[3-hydroxy-3-(4-methoxyphenyl)propyl]piperidin-1-ium-4-yl]methyl]-2-oxobenzimidazole-1-carboxamide; hydrochloride The procedure given in Example 135 was followed using 3-chloro-4'-methoxypropiophenone as a reactant, instead of 3-chloropropiophenone, to give the title compound.

1H-NMR (CDCl3, 200 MHz) δ 8.95 (m, 1H), 8.2 (m, 1H), 7.4-7.2 (m, 5H), 6.9 (m, 2H), 4.9 (m, 1H), 3.8 (s, 3H), 3.35 (m,

2H), 3.2 (m, 2H), 2.9 (m, 1H), 2.75 (m, 2H), 2.3-2.0 (m, 2H), 1.9 (m, 4H), 1.7 (m, 1H), 1.55 (m, 2H), 1.2-1.0 (m, 4H)

Example 145

[3-[4-[[(3-cyclopropyl-2-oxobenzimidazole-1-carbonyl)amino]methyl]piperidin-1-ium-1-yl]-1-phenylpropyl]carbamate; hydrochloride 3-cyclopropyl-N-[[1-(3-hydroxy-3-phenylpropyl)piperidin-4-yl]methyl]-2-oxobenzimidazole-1-carboxamide (1 mmol) was dissolved in 10 mL of THF and added with 1,1'-carbonyl diimidazole (1.5 mmol) at 0° C. The reaction mixture was stirred at room temperature for 2 h, followed by the addition of excess ammonium hydroxide (3 mL) at room temperature. After 2 h stirring at room temperature, water was added to terminate the reaction. The organic layer was extracted 3 times with dichloromethane, dried, and concentrated in vacuo. The resulting carbamate was dissolved in MC and the solution treated with a solution of HCl in ether. The resulting precipitate was filtered to give the title compound.
1H-NMR (CDCl3, 200 MHz) δ 9.00 (m, 1H), 8.20 (m, 1H), 7.31-7.18 (m, 8H), 5.71 (m, 1H), 4.73 (br, 2H), 3.35 (m, 2H), 3.12 (br, 2H), 2.90 (m, 2H), 2.80 (m, 1H), 2.30 (m, 2H), 2.07 (m, 2H), 1.86 (m, 2H), 1.75 (m, 1H), 1.60 (m, 2H), 1.20 (m, 2H), 1.05 (m, 2H)

Example 146

[3-[4-[[(2-oxo-3-propan-2-ylbenzimidazole-1-carbonyl)amino]methyl]piperidin-1-yl]-1-phenylpropyl]carbamate; hydrochloride The procedure given in Example 145 was followed using N-[[1-(3-hydroxy-3-phenylpropyl)piperidin-4-yl]methyl]-2-oxo-3-propan-2-ylbenzimidazole-1-carboxamide from Example 136 as a reactant, instead of 3-cyclopropyl-N-[[1-(3-hydroxy-3-phenylpropyl)piperidin-4-yl]methyl]-2-oxobenzimidazole-1-carboxamide, to give the title compound.
1H-NMR (CDCl3, 200 MHz) δ 9.0 (m, 1H), 8.3 (m, 1H), 7.8 (m, 1H), 7.4-7.1 (m, 9H), 5.75 (m, 1H), 4.8-4.6 (m, 3H), 3.35 (m, 2H), 3.1 (m, 2H), 2.55 (m, 3H), 2.4-2.0 (m, 5H), 1.9-1.6 (m, 4H), 1.5 (m, 6H)

Example 147

[1-(4-fluorophenyl)-3-[4-[[(2-oxo-3-propan-2-ylbenzimidazole-1-carbonyl)amino]methyl]piperidin-1-ium-1-yl]propyl]carbamate; hydrochloride The procedure given in Example 145 was followed using N-[[1-[3-(4-fluorophenyl)-3-hydroxypropyl]piperidin-1-ium-4-yl]methyl]-2-oxo-3-propan-2-ylbenzimidazole-1-carboxamide from Example 137 as a reactant, instead of 3-cyclopropyl-N-[[1-(3-hydroxy-3-phenylpropyl)piperidin-4-yl]methyl]-2-oxobenzimidazole-1-carboxamide, to give the title compound.
1H-NMR (CDCl3, 500 MHz) δ 9.00 (m, 1H), 8.25 (s, 1H), 7.36 (m, 2H), 7.20 (m, 3H), 7.05 (m, 2H), 5.69 (m, 1H), 4.72 (m, 1H), 3.36 (m, 2H), 3.20 (m, 2H), 2.65 (m, 2H), 2.3 (m, 2H), 1.93 (m, 3H), 1.79 (m, 2H), 1.65 (m, 2H), 1.58 (m, 6H)

Example 148

[3-[4-[[(3-cyclopropyl-2-oxobenzimidazole-1-carbonyl)amino]methyl]piperidin-1-ium-1-yl]-1-(4-fluorophenyl)propyl]carbamate; hydrochloride The procedure given in Example 145 was followed using 3-cyclopropyl-N-[[1-[3-(4-fluorophenyl)-3-hydroxypropyl] piperidin-1-ium-4-yl]methyl]-2-oxobenzimidazole-1-carboxamide from Example 138 as a reactant, instead of 3-cyclopropyl-N-[[1-(3-hydroxy-3-phenylpropyl)piperidin-4-yl]methyl]-2-oxobenzimidazole-1-carboxamide, to give the title compound.
1H-NMR (CDCl3, 200 MHz) δ 8.89 (m, 1H), 8.20 (m, 1H), 7.35-7.19 (m, 5H), 7.03 (m, 2H), 5.68 (m, 1H), 4.78 (br, 2H), 3.33 (m, 2H), 3.03 (m, 2H), 2.90 (m, 1H), 2.47 (m, 2H), 2.20 (m, 1H), 2.06 (m, 3H), 1.81 (m, 2H), 1.65 (m, 1H), 1.45 (m, 2H), 1.17 (m, 2H), 1.05 (m, 2H)

Example 149

[1-(4-chlorophenyl)-3-[4-[[(2-oxo-3-propan-2-ylbenzimidazole-1-carbonyl)amino]methyl]piperidin-1-ium-1-yl]propyl]carbamate; hydrochloride The procedure given in Example 145 was followed using N-[[1-[3-(4-chlorophenyl)-3-hydroxypropyl]piperidin-1-ium-4-yl]methyl]-2-oxo-3-propan-2-ylbenzimidazole-1-carboxamide from Example 139 as a reactant, instead of 3-cyclopropyl-N-[[1-(3-hydroxy-3-phenylpropyl)piperidin-4-yl]methyl]-2-oxobenzimidazole-1-carboxamide, to give the title compound.
1H-NMR (CDCl3, 200 MHz) δ 8.98 (m, 1H), 8.26 (m, 1H), 7.34-7.17 (m, 7H), 5.67 (m, 1H), 4.72 (m, 3H), 3.35 (m, 2H), 3.06 (m, 2H), 2.50 (m, 2H), 2.25 (m, 1H), 2.12 (m, 1H), 2.05 (m, 2H), 1.85 (m, 2H), 1.80 (m, 1H), 1.58 (m, 6H), 1.28 (m, 2H)

Example 150

[1-(4-chlorophenyl)-3-[4-[[(3-cyclopropyl-2-oxobenzimidazole-1-carbonyl)amino]methyl]piperidin-1-ium-1-yl]propyl]carbamate; hydrochloride The procedure given in Example 145 was followed using N-[[1-[3-(4-chlorophenyl)-3-hydroxypropyl]piperidin-1-ium-4-yl]methyl]-3-cyclopropyl-2-oxobenzimidazole-1-carboxamide from Example 140 as a reactant, instead of 3-cyclopropyl-N-[[1-(3-hydroxy-3-phenylpropyl)piperidin-4-yl]methyl]-2-oxobenzimidazole-1-carboxamide, to give the title compound.
1H-NMR (CDCl3, 500 MHz) δ 8.93 (m, 1H), 8.19 (m, 1H), 7.35-7.20 (m, 7H), 5.68 (m, 1H), 4.78 (m, 2H), 3.36 (m, 2H), 3.18 (m, 2H), 2.91 (m, 2H), 2.65 (m, 2H), 2.31 (m, 2H), 2.15 (m, 2H), 1.89 (m, 2H), 1.75 (m, 2H), 1.63 (m, 3H), 1.19 (m, 2H), 1.06 (m, 2H)

Example 151

[1-(4-methylphenyl)-3-[4-[[(2-oxo-3-propan-2-ylbenzimidazole-1-carbonyl)amino]methyl]piperidin-1-ium-1-yl]propyl]carbamate; hydrochloride The procedure given in Example 145 was followed using N-[[1-[3-hydroxy-3-(4-methylphenyl)propyl]piperidin-1-ium-4-yl]methyl]-2-oxo-3-propan-2-ylbenzimidazole-1-carboxamide from Example 141 as a reactant, instead of 3-cyclopropyl-N-[[1-(3-hydroxy-3-phenylpropyl)piperidin-4-yl]methyl]-2-oxobenzimidazole-1-carboxamide, to give the title compound.
1H-NMR (CDCl3, 200 MHz) δ 8.97 (m, 1H), 8.25 (m, 1H), 7.30-7.13 (m, 7H), 5.67 (m, 1H), 4.73 (m, 3H), 3.50 (m, 1H), 3.32 (m, 2H), 3.10 (m, 2H), 2.58 (m, 2H), 2.37 (m, 3H), 2.28 (m, 1H), 2.11 (m, 3H), 1.85 (m, 3H), 1.72 (m, 1H), 1.58 (m, 6H)

Example 152

[3-[4-[[(3-cyclopropyl-2-oxobenzimidazole-1-carbonyl)amino]methyl]piperidin-1-ium-1-yl]-1-(4-methylphenyl)propyl]carbamate; hydrochloride The procedure given in Example 145 was followed using 3-cyclopropyl-N-[[1-[3-hydroxy-3-(4-methylphenyl)propyl]piperidin-1-ium-4-yl]methyl]-2-oxobenzimidazole-1-carboxamide from Example 142 as a reactant, instead of 3-cyclopropyl-N-[[1-(3-hydroxy-3-phenylpropyl)piperidin-4-yl]methyl]-2-oxobenzimidazole-1-carboxamide, to give the title compound.

1H-NMR (CDCl3, 200 MHz) δ 8.90 (m, 1H), 8.20 (s, 1H), 7.32-7.13 (m, 7H), 5.66 (m, 1H), 4.73 (br, 2H), 3.35 (m, 2H), 3.12 (m, 2H), 2.91 (m, 1H), 2.60 (m, 2H), 2.40 (s, 3H), 2.27 (m, 2H), 1.61 (m, 2H), 1.87 (m, 2H), 1.72 (m, 1H), 1.59 (m, 2H), 1.20 (m, 2H), 1.06 (m, 2H)

Example 153

[1-(4-methoxyphenyl)-3-[4-[[(2-oxo-3-propan-2-ylbenzimidazole-1-carbonyl)amino]methyl]piperidin-1-ium-1-yl]propyl]carbamate; hydrochloride The procedure given in Example 145 was followed using N-[[1-[3-hydroxy-3-(4-methoxyphenyl)propyl]piperidin-1-ium-4-yl]methyl]-2-oxo-3-propan-2-ylbenzimidazole-1-carboxamide from Example 143 as a reactant, instead of 3-cyclopropyl-N-[[1-(3-hydroxy-3-phenylpropyl)piperidin-4-yl]methyl]-2-oxobenzimidazole-1-carboxamide, to give the title compound.

1H-NMR (CDCl3, 200 MHz) δ 9.0 (m, 1H), 8.25 (m, 1H), 7.35 (m, 3H), 7.2 (m, 3H), 6.9 (m, 2H), 5.65 (m, 1H), 4.95 (m, 2H), 4.7 (m, 1H), 3.8 (s, 3H), 3.4 (m, 2H), 3.2 (m, 2H), 2.7 (m, 2H), 2.4-2.1 (m, 4H), 1.9 (m, 3H), 1.7 (m, 2H), 1.6 (m, 6H)

Example 154

[3-[4-[[(3-cyclopropyl-2-oxobenzimidazole-1-carbonyl)amino]methyl]piperidin-1-ium-1-yl]-1-(4-methoxyphenyl)propyl]carbamate; hydrochloride The procedure given in Example 145 was followed using 3-cyclopropyl-N-[[1-[3-hydroxy-3-(4-methoxyphenyl)propyl]piperidin-1-ium-4-yl]methyl]-2-oxobenzimidazole-1-carboxamide from Example 144 as a reactant, instead of 3-cyclopropyl-N-[[1-(3-hydroxy-3-phenylpropyl)piperidin-4-yl]methyl]-2-oxobenzimidazole-1-carboxamide, to give the title compound.

1H-NMR (CDCl3, 200 MHz) δ 8.95 (m, 1H), 8.2 (m, 1H), 7.4-7.2 (m, 5H), 6.95 (m, 2H), 5.65 (m, 1H), 4.8 (m, 2H), 3.8 (s, 3H), 3.4 (m, 2H), 3.2 (m, 2H), 2.9 (m, 1H), 2.7 (m, 2H), 2.5-2.1 (m, 4H), 1.9 (m, 3H), 1.75 (m, 2H), 1.4-1.0 (m, 4H)

Example 155

N-[[1-[2-(4-fluorophenyl)-2-hydroxyethyl]piperidin-4-yl]methyl]-2-oxo-3-propan-2-ylbenzimidazole-1-carboxamide; hydrochloride A mixture of 3-isopropyl-2-oxo-2,3-dihydro-benzimidazole-1-carboxylic acid (piperidin-4-ylmethyl)-amide (5.0 mmol), 2-bromo-4'-fluoroacetophenone (6.0 mmol) and potassium carbonate (7.6 mmol) was stirred in 15 mL of acetonitrile for 2 h. This solution was then concentrated on a rotary evaporator and diluted with ethyl acetate. This mixture was then washed with brine, and the resulting organic layer was dried and purified by column chromatography. This was dissolved in ethanol (10 mL) and was added with sodium borohydride (10.0 mmol) at 0° C. and stirred at 25° C. for 2 h. This solution was concentrated on a rotary evaporator and diluted with ethylacetate. This mixture was washed with brine, dried, and concentrated in vacuo. The residue was purified by column chromatography. The resulting N-[[1-[2-(4-fluorophenyl)-2-hydroxyethyl]piperidin-1-ium-4-yl]methyl]-2-oxo-3-propan-2-ylbenzimidazole-1-carboxamide was dissolved in MC and the solution treated with a solution of HCl in ether. The resulting precipitate was filtered to give the title compound.

1H-NMR (CDCl3, 500 MHz) δ 9.01 (m, 1H), 8.26 (m, 1H), 7.37 (m, 2H), 7.20 (m, 3H), 7.05 (m, 2H), 4.90 (br, 2H), 3.38 (m, 2H), 3.30 (m, 1H), 3.08 (m, 1H), 2.63 (m, 2H), 2.50 (m, 1H), 2.25 (m, 1H), 1.91 (m, 2H), 1.80 (m, 1H), 1.59 (m, 8H)

Example 156

N-[[1-[2-hydroxy-2-(3-methoxyphenyl)ethyl]piperidin-1-ium-4-yl]methyl]-2-oxo-3-propan-2-ylbenzimidazole-1-carboxamide; hydrochloride The procedure given in Example 155 was followed using 2-bromo-3'-methoxyacetophenone as a reactant, instead of 2-bromo-4'-fluoroacetophenone, to give the title compound.

1H-NMR (CDCl3, 200 MHz) δ 9.05 (m, 1H), 8.3 (m, 1H), 7.35-7.1 (m, 5H), 7.0 (m, 2H), 6.85 (m, 1H), 4.9 (m, 1H), 4.85 (m, 1H), 3.95 (s, 3H), 3.4 (m, 3H), 3.1 (m, 1H), 2.85 (m, 2H), 2.5 (m, 1H), 2.3 (m, 1H), 1.95-1.8 (m, 3H), 1.6-1.5 (m, 8H)

Example 157

3-cyclopropyl-N-[[1-[2-hydroxy-2-(3-methoxyphenyl)ethyl]piperidin-1-ium-4-yl]methyl]-2-oxobenzimidazole-1-carboxamide; hydrochloride The procedure given in Example 155 was followed using 3-cyclopropyl-2-oxo-2,3-dihydro-benzimidazole-1-carboxylic acid (piperidin-4-ylmethyl)-amide and 2-bromo-3'-methoxyacetophenone as a reactant, instead of 3-isopropyl-2-oxo-2,3-dihydro-benzimidazole-1-carboxylic acid (piperidin-4-ylmethyl)-amide and 2-bromo-4'-fluoroacetophenone, to give the title compound.

1H-NMR (CDCl3, 200 MHz) δ 8.95 (m, 1H), 8.25 (m, 1H), 7.35-7.2 (m, 4H), 7.0 (m, 2H), 6.85 (m, 1H), 4.85 (m, 1H), 3.95 (s, 3H), 3.35 (m, 3H), 2.95 (m, 2H), 2.6 (m, 2H), 2.45 (M, 1H), 2.2 (m, 1H), 1.9 (m, 2H), 1.85 (m, 1H), 1.5 (m, 2H), 1.3-1.0 (m, 4H)

Example 158

[1-(4-fluorophenyl)-2-[4-[[(2-oxo-3-propan-2-ylbenzimidazole-1-carbonyl)amino]methyl]piperidin-1-ium-1-yl]ethyl]carbamate; hydrochloride The procedure given in Example 145 was followed using N-[[1-[2-(4-fluorophenyl)-2-hydroxyethyl]piperidin-4-yl]methyl]-2-oxo-3-propan-2-ylbenzimidazole-1-carboxamide from Example 155 as a reactant, instead of 3-cyclopropyl-N-[[1-(3-hydroxy-3-phenylpropyl)piperidin-4-yl]methyl]-2-oxobenzimidazole-1-carboxamide, to give the title compound.

1H-NMR (CDCl3, 500 MHz) δ 8.97 (m, 1H), 8.26 (m, 1H), 7.37 (m, 2H), 7.18 (m, 3H), 7.05 (m, 2H), 5.82 (m, 1H), 5.00 (m, 1H), 4.72 (m, 1H), 3.35 (m, 2H), 3.15-2.95 (m, 2H), 2.71

(m, 1H), 2.62 (m, 1H), 2.26 (m, 2H), 1.95 (m, 1H), 1.85 (m, 2H), 1.70 (m, 2H), 1.58 (m, 6H)

Example 159

[1-(3-methoxyphenyl)-2-[4-[[(2-oxo-3-propan-2-ylbenzimidazole-1-carbonyl)amino]methyl]piperidin-1-ium-1-yl]ethyl]carbamate; hydrochloride The procedure given in Example 145 was followed using N-[[1-[2-hydroxy-2-(3-methoxyphenyl)ethyl]piperidin-1-ium-4-yl]methyl]-2-oxo-3-propan-2-ylbenzimidazole-1-carboxamide from Example 156 as a reactant, instead of 3-cyclopropyl-N-[[1-(3-hydroxy-3-phenylpropyl)piperidin-4-yl]methyl]-2-oxobenzimidazole-1-carboxamide, to give the title compound.

1H-NMR (CDCl3, 200 MHz) δ 9.05 (m, 1H), 8.25 (m, 1H), 7.35-7.1 (m, 4H), 7.0-6.85 (m, 3H), 5.9 (m, 1H), 4.7 (m, 1H), 3.8 (s, 3H), 3.5-3.1 (m, 4H), 2.8 (m, 1H), 2.5 (m, 2H), 2.1-1.85 (m, 6H), 1.6 (m, 6H)

Example 160

[[2-[4-[[(3-cyclopropyl-2-oxobenzimidazole-1-carbonyl)amino]methyl]piperidin-1-ium-1-yl]-1-(3-methoxyphenyl)ethyl]carbamate; hydrochloride The procedure given in Example 145 was followed using 3-cyclopropyl-N-[[1-[2-hydroxy-2-(3-methoxyphenyl)ethyl]piperidin-1-ium-4-yl]methyl]-2-oxobenzimidazole-1-carboxamide from Example 157 as a reactant, instead of 3-cyclopropyl-N-[[1-(3-hydroxy-3-phenylpropyl)piperidin-4-yl]methyl]-2-oxobenzimidazole-1-carboxamide, to give the title compound.

1H-NMR (CDCl3, 200 MHz) δ 9.0 (m, 1H), 8.2 (m, 1H), 7.4-7.2 (m, 4H), 7.05-6.9 (m, 3H), 5.95 (m, 1H), 3.85 (s, 3H), 3.6-3.4 (m, 3H), 2.95 (m, 2H), 2.7 (m, 2H), 2.2-1.8 (m, 5H), 1.7 (m, 2H), 1.4-1.0 (m, 4H)

Example 161

Gastric Emptying Enhancing Activity

ICR CD strain male mice (body weight, 25-0.30 g; 8 mice per one group) were fasted for 24 h but allowed free access to water until 3 hours before the test.

Compounds to be tested for promoting GI motility were injected intraperitoneally or given orally at 30 min or 60 min prior to phenol red meal administration. Fifteen (15) min after administration of a test meal (0.5% Phenol red in 1.5% methylcellulose solution), mice were sacrificed and the stomach (pylorus~cardia) was removed and collected to vial. The stomach was homogenized with its contents in 0.1N NaOH and the mixture was centrifuged (700*g) for 20 min. 2.5 mL of the supernatant was added to 0.25 mL of trichloroacetic acid solution (20% w/v) to precipitate proteins. After centrifuging (2600*g) for 20 min, 0.5 mL of the supernatant was added to 0.25 mL of 1N NaOH. The mixture was homogenized and its absorbance (Abs) was read at 560 nm.

In each experiment, one group was sacrificed just after the administration of the test meal and was considered as a standard (0% emptying). The gastric emptying (GE) at the 15 min period was calculated according to the following formula.

$$GE(\%) = (1 - Abs_{test}/Abs_{standard}) \times 100$$

$$Increase(\%) = (GE\%_{test} - GE\%_{vehicle})/GE\%_{vehicle} \times 100$$

As shown in Table 1, most compounds of this invention exhibited a potent gastric emptying enhancing effect at a dose of 3 mg/kg.

As is clear from the above experimental result, the compounds of the structural formula (I) and pharmaceutically useful salts have excellent gastrointestinal motility enhancing activity, and hence are useful for treating the diseases of the gastrointestinal tract such as irritable bowel syndrome (IBS), specifically constipation-predominant IBS, and gastric motility disorder.

5-Hydroxytryptamine (5-HT) released from enterochromaffin cells regulate gastrointestinal function in either an excitatory or inhibitory manner. The gastrointestinal motility enhancing activity is characteristic of agonism on 5-HT4 receptors. 5-HT4 receptor agonists can stimulate upper or lower gut motility while 5-HT4 antagonists inhibit the enhanced gut motility by 5-HT4 agonists.

The compounds of the structural formula (I) have 5-HT4 receptor binding activity and stimulate gut motility (see Table 1). Therefore, enhancing gut motility of the compounds of the structural formula (I) is believed to be mediated by agonism on 5-HT4 receptors.

TABLE 1

| Gastric Emptying Enhancing Activity (3.0 mg/kg i.p.) | |
|---|---|
| Example | Increase % |
| 2 | 42.6% |
| 3 | 71.1% |
| 4 | 74.1% |
| 5 | 76.1% |
| 8 | 51.6% |
| 9 | 55.8% |
| 13 | 14.0% |
| 15 | 78.7% |
| 16 | 53.6% |
| 17 | 22.1% |
| 23 | 55.8% |
| 24 | 71.1% |
| 27 | 48.5% |
| 29 | 61.3% |
| 31 | 79.3% |
| 32 | 40.0% |
| 33 | 115.2% |
| 35 | 105.5% |
| 36 | 55.2% |
| 37 | 70.7% |
| 38 | 49.1% |
| 39 | 40.0% |
| 40 | 51.6% |
| 41 | 24.3% |
| 42 | 42.7% |
| 43 | 46.1% |
| 45 | 51.4% |
| 46 | 45.9% |
| 47 | 25.9% |
| 48 | 3.5% |
| 49 | 17.8% |
| 50 | 3.9% |
| 51 | 122.1% |
| 52 | 131.0% |
| 53 | 28.4% |
| 54 | 89.2% |
| 55 | 66.7% |
| 56 | 134.7% |
| 57 | 29.0% |
| 58 | 48.3% |
| 59 | 48.0% |
| 60 | 14.2% |
| 61 | 44.3% |
| 62 | 17.9% |
| 63 | 24.4% |
| 64 | 7.3% |
| 65 | 93.1% |

TABLE 1-continued

Gastric Emptying Enhancing Activity (3.0 mg/kg i.p.)

| Example | Increase % |
|---------|------------|
| 66 | 84.1% |
| 68 | 52.9 |
| 70 | 67.5% |
| 71 | 63.7% |
| 72 | 48.1% |
| 74 | 46.7% |
| 83 | 42.5% |
| 88 | 44.1% |
| 89 | 45.3% |
| 96 | 105.0% |
| 97 | 71.4% |
| 98 | 63.6% |
| 99 | 47.5% |
| 100 | 46.1% |
| 103 | 88.8% |
| 104 | 81.0% |
| 111 | 37.2% |
| 121 | 46.8% |
| 122 | 6.8% |
| 123 | 56.8% |
| 124 | 45.6% |
| 126 | 93.3% |
| 127 | 11.3% |
| 129 | 5.4% |
| 135 | 90.3% |
| 136 | 64.1% |
| 146 | 83.0% | abdomen. Electrodes were exteriorized on the back of the neck and protected by a glass tube attached to the skin.

Colorectal distension (CRD) was performed with balloon inflated by 5 min steps of 15 mmHg from 0 to 60 mmHg by connecting the balloon to computerized barostat. Rats were submitted to CRD 1 day before (basal condition) and 3 days after intra-rectal administration of trinitrobenzene sulfonic acid (TNBS 80 mg/kg intrarectally). Colonic pressure and balloon volume were continuously monitored on a potentiometric recorder (L6514, Linseis, Selb, Germany) with a paper speed of 1 cm·min−1.

Five day after the administration of TNBS, rats were treated with test article or their vehicle (carboxymethyl cellulose 0.5%, 1 mL po) one hour before distension. The number of spike bursts that correspond to abdominal contractions was determined per 5 min periods. Values are expressed as means±SEM. Statistical analysis was performed using the Student's "t" test and criterion for statistical significance was $p<0.05$.

Table 2 summarizes the result of the activity of the compound obtained in Example 68 as a test compound in the TNBS-induced colorectal hypersensitivity model. Significant decreases in abdominal contraction are observed at 10 mg/kg and 30 mg/kg of test compound. This result shows that the compound according to one embodiment of the present invention has visceral pain reducing activity in rat preclinical model.

TABLE 2

Effect of a test compound on TNBS-induced colorectal hypersensitivity in rats

| | Number of abdominal contraction/5 min | | | | |
|---|---|---|---|---|---|
| | 0 mmHg[a] | 15 mmHg[a] | 30 mmHg[a] | 45 mmHg[a] | 60 mmHg[a] |
| Vehicle | 1.1 ± 0.6 | 5.3 ± 1.6 | 14.0 ± 2.9 | 25.7 ± 2.9 | 30.7 ± 2.7 |
| TNBS + Vehicle | 3.2 ± 1.1 | 13.3 ± 1.6 | 27.5 ± 4.0 | 39.0 ± 5.2 | 45.5 ± 4.7 |
| TNBS + test compound (10 mg/kg, po) | 4.7 ± 1.2 | 14.7 ± 2.5 | 19.9* ± 2.5 | 31.0 ± 3.9 | 37.1 ± 6.0 |
| TNBS + test compound (30 mg/kg, po) | 2.1 ± 0.7 | 7.3* ± 1.8 | 15.3* ± 3.0 | 21.4* ± 2.1 | 28.3* ± 3.1 |

[a]Pressure of distension
*p < 0.05 significantly different from "TNBS + Vehicle"

Hypersensitivity to colorectal distension is common in patients with IBS and may be responsible for the major symptom of visceral pain. Both inflammatory and non-inflammatory animal models of visceral hyperalgesia to distension as will be described in Example 162 and 163, respectively, have been developed to investigate the effect of a compound on visceral pain in IBS.

Example 162

TNBS-Induced Colorectal Hypersensitivity Test

Wistar rats (body weight, 200-225 g; 8-10 rats per a group) were surgically prepared for electromyographic recording to a previously described technique (Morteau et al., Dig Dis Sci, 1994, 39(6):1239-1248). After laparotomy, three groups of three electrodes were implanted in the striated muscles of the Example 163

PRS (Partial Restraint Stress)-Induced Colorectal Hypersensitivity Test

Adult female Wistar rats (body weight, 225-250 g; 6-7 rats per group) were prepared for electromyography. After anaesthetization, three pairs of nichrome wire electrodes were implanted bilaterally in the striated muscles at 3 cm laterally from the midline. The free ends of electrodes were exteriorized on the back of the neck and protected by a glass tube attached to the skin.

PRS, a relatively mild stress, was performed as previously described in Bradesi S, Eutamene H, Garcia-Villar R, Fioramonti J, Bueno L; 'Acute and chronic stress differently affect visceral sensitivity to rectal distension in female rats.' Neurogastroenterol. Mot. (2002) 14, 75-82.

Rats were placed in a plastic tunnel, where they are not allowed to move or escape several days before colorectal distension (CRD). The balloon, connected to a barostat was inflated progressively by steps of 15 mmHg, from 0, 15, 30, 45 and 60 mmHg, each step of inflation lasting 5 min. To determine the antinoiciceptive effect of a test compound on PRS-induced visceral hypersensitivity, the test compound or vehicle (CMC 0.5%) was given orally (PO), 1 hr 15 min after the beginning of the PRS. Three hours before and 15 min after the stress session, a CRD was performed.

The number of spike bursts corresponding to abdominal contractions per 5 min periods was determined for each volume of distension. Colonic pressure and balloon volume were continuously monitored on a potentiometric recorder (L6514, Linseis, Selb, Germany). Values are expressed as means±SEM.

Statistical analysis was performed by a one way analysis of variance (ANOVA) followed by a Dunnett test. p<0.05 was considered as significant.

Table 3 summarizes the results of the activity of the compound obtained in Example 68 as a test compound in the PRS-induced colorectal hypersensitivity model. Significant decreases in abdominal contraction are observed at 30 mg/kg. This result shows that the compound according to one embodiment of the present invention has visceral pain reducing activity.

TABLE 3

Effect of a test compound on PRS-induced colorectal hypersensitivity in rats

| | Number of abdominal contraction/5 min | | | | |
|---|---|---|---|---|---|
| | 0 mmHg[a] | 15 mmHg[a] | 30 mmHg[a] | 45 mmHg[a] | 60 mmHg[a] |
| Vehicle | 0.7 ± 0.3 | 3.7 ± 1.4 | 13.3 ± 2.2 | 18.8 ± 4.1 | 23.3 ± 3.9 |
| PRS + vehicle | 2.0 ± 0.8 | 7.0 ± 3.1 | 33.2 ± 7.9 | 54.2 ± 6.5 | 57.8 ± 6.3 |
| PRS + Test compound (30 mg/kg, po) | 4.9 ± 1.1 | 2.7 ± 0.9 | 11.9* ± 2.3 | 35.3* ± 5.3 | 46.0 ± 3.3 |

[a]Pressure of distension
*p < 0.05 compared to "PRS + vehicle"

What is claimed is:

1. A compound of Formula (I):

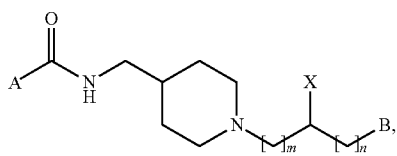

Formula (I)

or a pharmaceutically acceptable salt thereof, wherein
m is 1 or 2;
n is 0, 1 or 2;
A is a substitution group of Formula (II):

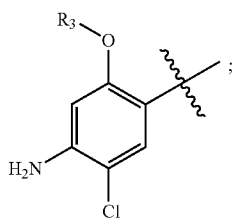

Formula (II)

X is hydroxy or —OCONR₁R₂;
R₁ and R₂ are independently selected from the group consisting of —H, $C_1$-$C_6$ linear or branched alkyl, benzyl, and five- to seven-membered cyclyl or heterocyclyl substituted with one or more groups independently selected from $C_1$-$C_6$ linear or branched alkyl, or R₁ and R₂, together with a nitrogen atom to which they are attached, form five- to seven-membered heterocyclyl;

R₃ is $C_1$-$C_6$ linear or branched alkyl; and

B is phenyl, phenoxy, thienyl or naphthyl, wherein B is substituted with one or more groups independently selected from —H, halo, nitro, cyano, —SO₂CH₃, trifluoromethyl, trifluoromethoxy, difluoromethoxy, phenyl, $C_1$-$C_6$ linear or branched alkyl, and $C_1$-$C_6$ linear or branched alkoxy.

2. The compound of claim 1, wherein the compound is selected from the group consisting of:

4-amino-5-chloro-N-[[1-(2-hydroxy-2-phenylethyl)piperidin-4-yl]methyl]-2-methoxybenzamide, 4-amino-5-chloro-N-[[1-[[2-(4-fluorophenyl)-2-hydroxyethyl]piperidin-4-yl]methyl]-2-methoxybenzamide, 4-amino-5-chloro-N-[[1-[[2-hydroxy-2-(4-methylphenyl)ethyl]piperidin-4-yl]methyl]-2-methoxybenzamide, 4-amino-5-chloro-N-[[1-[[2-hydroxy-2-(4-methoxyphenyl)ethyl]piperidin-4-yl]-methyl]-2-methoxybenzamide, 4-amino-5-chloro-N-[[1-[[2-(4-cyanophenyl)-2-hydroxyethyl]piperidin-4-yl]methyl]-2-methoxybenzamide, 4-amino-5-chloro-N-[[1-[[2-(4-chlorophenyl)-2-hydroxyethyl]piperidin-4-yl]methyl]-2-methoxybenzamide, 4-amino-5-chloro-N-[[1-[[2-hydroxy-2-(4-phenylphenyl)ethyl]piperidin-4-yl]methyl]-2-methoxybenzamide, 4-amino-5-chloro-N-[[1-[[2-hydroxy-2-(2-methoxyphenyl)ethyl]piperidin-4-yl]-methyl]-2-methoxybenzamide, 4-amino-5-chloro-N-[[1-[[2-hydroxy-2-(3-methoxyphenyl)ethyl]piperidin-4-yl]-methyl]-2-methoxybenzamide, 4-amino-5-chloro-N-[[1-[[2-(3,4-dichlorophenyl)-2-hydroxyethyl]piperidin-4-yl]methyl]-2-methoxybenzamide, 4-amino-5-chloro-N-[[1-[[2-(2,4-difluorophenyl)-2-hydroxyethyl]piperidin-4-yl]methyl]-2-methoxybenzamide, 4-amino-N-[[1-[2-(4-tert-butylphenyl)-2-hydroxyethyl]piperidin-4-yl]methyl]-5-chloro-2-methoxybenzamide, 4-amino-5-chloro-N-[[1-[[2-(2-chlorophenyl)-2-hydroxyethyl]piperidin-4-yl]methyl]-2-methoxybenzamide, 4-amino-5-chloro-N-[[1-[[2-(2,4-dimethylphenyl)-2-hydroxyethyl]piperidin-4-yl]methyl]-2-methoxybenzamide, 4-amino-5-chloro-N-[[1-[2-(2,5-dimethoxyphenyl)-2-hydroxyethyl]piperidin-4-yl]methyl]-2-methoxybenzamide,
4-amino-5-chloro-N-[[1-[2-[4-(difluoromethoxy)phenyl]-2-hydroxyethyl]piperidin-4-yl]methyl]-2-methoxybenzamide,
4-amino-5-chloro-N-[[1-[2-(3,4-difluorophenyl)-2-hydroxyethyl]piperidin-4-yl]methyl]-2-methoxybenzamide,
4-amino-5-chloro-N-[[1-[2-hydroxy-2-[4-(trifluoromethyl)phenyl]ethyl]piperidin-4-yl]methyl]-2-methoxybenzamide,
4-amino-5-chloro-N-[[1-[2-(2,4-dichlorophenyl)-2-hydroxyethyl]piperidin-4-yl]methyl]-2-methoxybenzamide,
4-amino-5-chloro-N-[[1-[(2S)-2-hydroxy-2-phenylethyl]piperidin-4-yl]methyl]-2-methoxybenzamide,
4-amino-5-chloro-N-[[1-[(2R)-2-hydroxy-2-phenylethyl]piperidin-4-yl]methyl]-2-methoxybenzamide,
[2-[4-[[(4-amino-5-chloro-2-methoxybenzoyl)amino]methyl]piperidin-1-yl]-1-phenylethyl]carbamate,
[2-[4-[[(4-amino-5-chloro-2-methoxybenzoyl)amino]methyl]piperidin-1-yl]-1-(4-fluorophenyl)ethyl]carbamate,
[2-[4-[[(4-amino-5-chloro-2-methoxybenzoyl)amino]methyl]piperidin-1-yl]-1-(4-methylphenyl)ethyl]carbamate,
[2-[4-[[(4-amino-5-chloro-2-methoxybenzoyl)amino]methyl]piperidin-1-yl]-1-(4-cyanophenyl)ethyl]carbamate,
[2-[4-[[(4-amino-5-chloro-2-methoxybenzoyl)amino]methyl]piperidin-1-yl]-1-(4-phenylphenyl)ethyl]carbamate,
[2-[4-[[(4-amino-5-chloro-2-methoxybenzoyl)amino]methyl]piperidin-1-yl]-1-(3-methoxy phenyl)ethyl]carbamate,
[2-[4-[[(4-amino-5-chloro-2-methoxybenzoyl)amino]methyl]piperidin-1-yl]-1-(3,4-dichlorophenyl)ethyl]carbamate,
[2-[4-[[(4-amino-5-chloro-2-methoxybenzoyl)amino]methyl]piperidin-1-yl]-1-(2-chlorophenyl)ethyl]carbamate,
[2-[4-[[(4-amino-5-chloro-2-methoxybenzoyl)amino]methyl]piperidin-1-yl]-1-(2,4-dimethyl phenyl)ethyl]carbamate,
[2-[4-[[(4-amino-5-chloro-2-methoxybenzoyl)amino]methyl]piperidin-1-yl]-1-(2,5-dimethoxy phenyl)ethyl]carbamate,
[2-[4-[[(4-amino-5-chloro-2-methoxybenzoyl)amino]methyl]piperidin-1-yl]-1-[4-(difluoromethoxy)phenyl]ethyl]carbamate,
[2-[4-[[(4-amino-5-chloro-2-methoxybenzoyl)amino]methyl]piperidin-1-yl]-1-(3,4-difluorophenyl)ethyl]carbamate,
[2-[4-[[(4-amino-5-chloro-2-methoxybenzoyl)amino]methyl]piperidin-1-yl]-1-[4-(trifluoromethyl)phenyl]ethyl]carbamate,
[2-[4-[[(4-amino-5-chloro-2-methoxybenzoyl)amino]methyl]piperidin-1-yl]-1-(2,4-dichlorophenyl)ethyl]carbamate,
4-amino-5-chloro-N-[[1-(3-hydroxy-3-phenylpropyl)piperidin-4-yl]methyl]-2-methoxybenzamide,
4-amino-5-chloro-N-[[1-[3-(4-fluorophenyl)-3-hydroxypropyl]piperidin-4-yl]-methyl]-2-methoxybenzamide,
4-amino-5-chloro-N-[[1-[3-(4-chlorophenyl)-3-hydroxypropyl]piperidin-4-yl]-methyl]-2-methoxybenzamide,
4-amino-5-chloro-N-[[1-[3-hydroxy-3-(4-methylphenyl)propyl]piperidin-4-yl]-methyl]-2-methoxybenzamide,
4-amino-5-chloro-N-[[1-[3-hydroxy-3-(4-methoxyphenyl) propyl]piperidin-4-yl]methyl]-2-methoxybenzamide,
4-amino-5-chloro-N-[[1-[3-(2-chlorophenyl)-3-hydroxypropyl]piperidin-4-yl]-methyl]-2-methoxybenzamide,
4-amino-5-chloro-N-[[1-[3-(3-chlorophenyl)-3-hydroxypropyl]piperidin-4-yl]-methyl]-2-methoxybenzamide,
4-amino-5-chloro-N-[[1-[3-(2-fluorophenyl)-3-hydroxypropyl]piperidin-4-yl]-methyl]-2-methoxybenzamide,
4-amino-5-chloro-N-[[1-[3-(3-fluorophenyl)-3-hydroxypropyl]piperidin-4-yl]-methyl]-2-methoxybenzamide,
4-amino-5-chloro-N-[[1-[3-(2,3-dichlorophenyl)-3-hydroxypropyl]piperidin-4-yl]methyl]-2-methoxybenzamide,
4-amino-5-chloro-N-[[1-[3-(2,4-dichlorophenyl)-3-hydroxypropyl]piperidin-4-yl]methyl]-2-methoxybenzamide,
4-amino-5-chloro-N-[[1-[3-(3,4-dichlorophenyl)-3-hydroxypropyl]piperidin-4-yl]methyl]-2-methoxybenzamide,
4-amino-5-chloro-N-[[1-[3-(4-isopropylphenyl)-3-hydroxypropyl]piperidin-4-yl]methyl]-2-methoxybenzamide,
4-amino-5-chloro-N-[[1-[3-(3-methoxyphenyl)-3-hydroxypropyl]piperidin-4-yl]methyl]-2-methoxybenzamide,
4-amino-5-chloro-N-[[1-(3-hydroxy-3-thiophen-2-ylpropyl)piperidin-4-yl]methyl]-2-methoxybenzamide,
4-amino-5-chloro-N-[[1-[4-(4-fluorophenyl)-3-hydroxybutyl]piperidin-4-yl]methyl]-2-methoxybenzamide,
4-amino-5-chloro-N-[[1-[5-(4-fluorophenyl)-3-hydroxypentyl]piperidin-4-yl]-methyl]-2-methoxybenzamide,
[3-[4-[[(4-amino-5-chloro-2-methoxybenzoyl)amino]methyl]piperidin-1-yl]-1-phenylpropyl]carbamate,
[3-[4-[[(4-amino-5-chloro-2-methoxybenzoyl)amino]methyl]piperidin-1-yl]-1-(4-fluorophenyl)propyl]carbamate,
[3-[4-[[(4-amino-5-chloro-2-methoxybenzoyl)amino]methyl]piperidin-1-yl]-1-(4-chlorophenyl)propyl]carbamate,
[3-[4-[[(4-amino-5-chloro-2-methoxybenzoyl)amino]methyl]piperidin-1-yl]-1-(2-chlorophenyl)propyl]carbamate,
[3-[4-[[(4-amino-5-chloro-2-methoxybenzoyl)amino]methyl]piperidin-1-yl]-1-(2-fluorophenyl)propyl]carbamate,
[3-[4-[[(4-amino-5-chloro-2-methoxybenzoyl)amino]methyl]piperidin-1-yl]-1-(3-fluorophenyl)propyl]carbamate,
[3-[4-[[(4-amino-5-chloro-2-methoxybenzoyl)amino]methyl]piperidin-1-yl]-1-(2,3-dichlorophenyl)propyl]carbamate,
[3-[4-[[(4-amino-5-chloro-2-methoxybenzoyl)amino]methyl]piperidin-1-yl]-1-(2,4-dichlorophenyl)propyl]carbamate,
[3-[4-[[(4-amino-5-chloro-2-methoxybenzoyl)amino]methyl]piperidin-1-yl]-1-(3,4-dichlorophenyl)propyl]carbamate,

[3-[4-[[(4-amino-5-chloro-2-methoxybenzoyl)amino]methyl]piperidin-1-yl]-1-(4-isopropylphenyl)propyl]carbamate,
[3-[4-[[(4-amino-5-chloro-2-methoxybenzoyl)amino]methyl]piperidin-1-yl]-1-(3-methoxy phenyl)propyl]carbamate,
[3-[4-[[(4-amino-5-chloro-2-methoxybenzoyl)amino]methyl]piperidin-1-yl]-1-thiophen-2-ylpropyl]carbamate,
[4-[4-[[(4-amino-5-chloro-2-methoxybenzoyl)amino]methyl]piperidin-1-yl]-1-(4-fluorophenyl)butan-2-yl]carbamate,
[1-[4-[[(4-amino-5-chloro-2-methoxybenzoyl)amino]methyl]piperidin-1-yl]-5-(4-fluorophenyl)pentan-3-yl]carbamate,
(S)-4-amino-5-chloro-N-[[1-[3-(4-fluorophenyl)-3-hydroxypropyl]piperidin-4-yl]methyl]-2-methoxybenzamide,
(S)-3-[4-[[(4-amino-5-chloro-2-methoxybenzoyl)amino]methyl]piperidin-1-yl]-1-(4-fluorophenyl)propyl carbamate,
(R)-4-amino-5-chloro-N-[[1-[3-(4-fluorophenyl)-3-hydroxypropyl]piperidin-4-yl]methyl]-2-methoxybenzamide,
(R)-[3-[4-[[(4-amino-5-chloro-2-methoxybenzoyl)amino]methyl]piperidin-1-yl]-1-(4-fluorophenyl)propyl]carbamate,
4-amino-5-chloro-N-[[1-(2-hydroxy-3-phenoxypropyl)piperidin-4-yl]methyl]-2-methoxybenzamide,
4-amino-5-chloro-N-[[1-[3-(4-fluorophenoxy)-2-hydroxypropyl]piperidin-4-yl]methyl]-2-methoxybenzamide,
4-amino-5-chloro-N-[[1-[3-(4-chlorophenoxy)-2-hydroxypropyl]piperidin-4-yl]methyl]-2-methoxybenzamide,
4-amino-5-chloro-N-[[1-[2-hydroxy-3-(4-methoxyphenoxy) propyl]piperidin-4-yl]methyl]-2-methoxybenzamide,
4-amino-5-chloro-N-[[1-[3-(2,3-dichlorophenoxy)-2-hydroxypropyl]piperidin-4-yl]methyl]-2-methoxybenzamide,
4-amino-5-chloro-N-[[1-[3-(2,4-dichlorophenoxy)-2-hydroxypropyl]piperidin-4-yl]methyl]-2-methoxybenzamide,
4-amino-5-chloro-N-[[1-[3-(2,5-dichlorophenoxy)-2-hydroxypropyl]piperidin-4-yl]methyl]-2-methoxybenzamide,
4-amino-5-chloro-N-[[1-[3-(2,6-dichlorophenoxy)-2-hydroxypropyl]piperidin-4-yl]methyl]-2-methoxybenzamide,
4-amino-5-chloro-N-[[1-[3-(3,4-dichlorophenoxy)-2-hydroxypropyl]piperidin-4-yl]methyl]-2-methoxybenzamide,
4-amino-5-chloro-N-[[1-[3-(2-chlorophenoxy)-2-hydroxypropyl]piperidin-4-yl]methyl]-2-methoxybenzamide,
4-amino-5-chloro-N-[[1-[3-(4-methylphenoxy)-2-hydroxypropyl]piperidin-4-yl-]methyl]-2-methoxybenzamide,
4-amino-5-chloro-N-[[1-[3-(3,4-difluorophenoxy)-2-hydroxypropyl]piperidin-4-yl]methyl]-2-methoxybenzamide,
4-amino-5-chloro-N-[[1-[2-hydroxy-3-[4-(trifluoromethyl)phenoxy]propyl]piperidin-4-yl]methyl]-2-methoxybenzamide,
4-amino-5-chloro-N-[[1-[2-hydroxy-3-(4-phenylphenoxy)propyl]piperidin-4-yl]methyl]-2-methoxybenzamide,
4-amino-5-chloro-N-[[1-(2-hydroxy-3-naphthalen-2-yloxypropyl)piperidin-4-yl]methyl]-2-methoxybenzamide,
4-amino-5-chloro-N-[[1-(2-hydroxy-3-phenylpropyl)piperidin-1-ium-4-yl]methyl]-2-methoxybenzamide,
[1-[4-[[(4-amino-5-chloro-2-methoxybenzoyl)amino]methyl]piperidin-1-yl]-3-phenoxypropan-2-yl]carbamate,
[1-[4-[[(4-amino-5-chloro-2-methoxybenzoyl)amino]methyl]piperidin-1-yl]-3-phenoxypropan-2-yl]piperidine-1-carboxylate,
[1-[4-[[(4-amino-5-chloro-2-methoxybenzoyl)amino]methyl]piperidin-1-yl]-3-(4-fluorophenoxy)propan-2-yl] 3,5-dimethylpiperidine-1-carboxylate,
[1-[4-[[(4-amino-5-chloro-2-methoxybenzoyl)amino]methyl]piperidin-1-yl]-3-(4-chlorophenoxy)propan-2-yl] 3,5-dimethylpiperidine-1-carboxylate,
[1-[4-[[(4-amino-5-chloro-2-methoxybenzoyl)amino]methyl]piperidin-1-yl]-3-(4-methoxyphenoxy)propan-2-yl]carbamate,
[1-[4-[[(4-amino-5-chloro-2-methoxybenzoyl)amino]methyl]piperidin-1-yl]-3-(2,3-dichlorophenoxy)propan-2-yl]carbamate,
[1-[4-[[(4-amino-5-chloro-2-methoxybenzoyl)amino]methyl]piperidin-1-yl]-3-(2,3-dichlorophenoxy)propan-2-yl]pyrrolidine-1-carboxylate,
[1-[4-[[(4-amino-5-chloro-2-methoxybenzoyl)amino]methyl]piperidin-1-yl]-3-(2,3-dichlorophenoxy)propan-2-yl]piperidine-1-carboxylate,
[1-[4-[[(4-amino-5-chloro-2-methoxybenzoyl)amino]methyl]piperidin-1-yl]-3-(2,3-dichlorophenoxy)propan-2-yl]azepane-1-carboxylate,
[1-[4-[[(4-amino-5-chloro-2-methoxybenzoyl)amino]methyl]piperidin-1-yl]-3-(2,4-dichlorophenoxy)propan-2-yl]carbamate,
[1-[4-[[(4-amino-5-chloro-2-methoxybenzoyl)amino]methyl]piperidin-1-yl]-3-(2,5-dichlorophenoxy)propan-2-yl]carbamate,
[1-[4-[[(4-amino-5-chloro-2-methoxybenzoyl)amino]methyl]piperidin-1-yl]-3-(2,6-dichlorophenoxy)propan-2-yl]carbamate,
[1-[4-[[(4-amino-5-chloro-2-methoxybenzoyl)amino]methyl]piperidin-1-yl]-3-(3,4-dichlorophenoxy)propan-2-yl]carbamate,
[1-[4-[[(4-amino-5-chloro-2-methoxybenzoyl)amino]methyl]piperidin-1-yl]-3-[4-(trifluoromethyl)phenoxy]propan-2-yl]carbamate,
[1-[4-[[(4-amino-5-chloro-2-methoxybenzoyl)amino]methyl]piperidin-1-yl]-3-(4-phenylphenoxy)propan-2-yl]carbamate,
[1-[4-[[(4-amino-5-chloro-2-methoxybenzoyl)amino]methyl]piperidin-1-yl]-3-naphthalen-2-yloxypropan-2-yl]carbamate, and
[1-[4-[[(4-amino-5-chloro-2-methoxybenzoyl)amino]methyl]piperidin-1-yl]-3-phenylpropan-2-yl]carbamate.

3. The compound of claim 1, wherein X is —OH.

4. The compound of claim 3, wherein m is 2, and n is 0.

5. The compound of claim 3, wherein B is phenyl substituted with one or more groups independently selected from —H, halo, nitro, cyano, —$SO_2CH_3$, trifluoromethyl, trifluoromethoxy, difluoromethoxy, phenyl, $C_1$-$C_6$ linear or branched alkyl, and $C_1$-$C_6$ linear or branched alkoxy.

6. The compound of claim 3, wherein B is phenyl substituted with one or more halo.

7. The compound of claim 3, wherein the compound is selected from the group consisting of:
4-amino-5-chloro-N-[[1-(2-hydroxy-2-phenylethyl)piperidin-4-yl]methyl]-2-methoxybenzamide,
4-amino-5-chloro-N-[[1-[2-(4-fluorophenyl)-2-hydroxyethyl]piperidin-4-yl]methyl]-2-methoxybenzamide, 4-amino-5-chloro-N-[[1-[2-hydroxy-2-(4-methylphenyl) ethyl]piperidin-4-yl]methyl]-2-methoxybenzamide,
4-amino-5-chloro-N-[[1-[2-hydroxy-2-(4-methoxyphenyl)ethyl]piperidin-4-yl]-methyl]-2-methoxybenzamide,
4-amino-5-chloro-N-[[1-[2-(4-cyanophenyl)-2-hydroxyethyl]piperidin-4-yl]methyl]-2-methoxybenzamide,
4-amino-5-chloro-N-[[1-[2-(4-chlorophenyl)-2-hydroxyethyl]piperidin-4-yl]methyl]-2-methoxybenzamide,
4-amino-5-chloro-N-[[1-[2-hydroxy-2-(4-phenylphenyl) ethyl]piperidin-4-yl]methyl]-2-methoxybenzamide,
4-amino-5-chloro-N-[[1-[2-hydroxy-2-(2-methoxyphenyl)ethyl]piperidin-4-yl]-methyl]-2-methoxybenzamide,
4-amino-5-chloro-N-[[1-[2-hydroxy-2-(3-methoxyphenyl)ethyl]piperidin-4-yl]-methyl]-2-methoxybenzamide,
4-amino-5-chloro-N-[[1-[[2-(3,4-dichlorophenyl)-2-hydroxyethyl]piperidin-4-yl]methyl]-2-methoxybenzamide,
4-amino-5-chloro-N-[[1-[[2-(2,4-difluorophenyl)-2-hydroxyethyl]piperidin-4-yl]methyl]-2-methoxybenzamide,
4-amino-N-[[1-[2-(4-tert-butylphenyl)-2-hydroxyethyl] piperidin-4-yl]methyl]-5-chloro-2-methoxybenzamide,
4-amino-5-chloro-N-[[1-[[2-(2-chlorophenyl)-2-hydroxyethyl]piperidin-4-yl]methyl]-2-methoxybenzamide,
4-amino-5-chloro-N-[[1-[[2-(2,4-dimethylphenyl)-2-hydroxyethyl]piperidin-4-yl]methyl]-2-methoxybenzamide,
4-amino-5-chloro-N-[[1-[[2-(2,5-dimethoxyphenyl)-2-hydroxyethyl]piperidin-4-yl]methyl]-2-methoxybenzamide,
4-amino-5-chloro-N-[[1-[[2-[4-(difluoromethoxy)phenyl]-2-hydroxyethyl]piperidin-4-yl]methyl]-2-methoxybenzamide,
4-amino-5-chloro-N-[[1-[[2-(3,4-difluorophenyl)-2-hydroxyethyl]piperidin-4-yl]methyl]-2-methoxybenzamide,
4-amino-5-chloro-N-[[1-[[2-hydroxy-2-[4-(trifluoromethyl)phenyl]ethyl]piperidin-4-yl]methyl]-2-methoxybenzamide,
4-amino-5-chloro-N-[[1-[[2-(2,4-dichlorophenyl)-2-hydroxyethyl]piperidin-4-yl]methyl]-2-methoxybenzamide,
4-amino-5-chloro-N-[[1-[(2S)-2-hydroxy-2-phenylethyl] piperidin-4-yl]methyl]-2-methoxybenzamide,
4-amino-5-chloro-N-[[1-[(2R)-2-hydroxy-2-phenylethyl] piperidin-4-yl]methyl]-2-methoxybenzamide,
4-amino-5-chloro-N-[[1-(3-hydroxy-3-phenylpropyl)piperidin-4-yl]methyl]-2-methoxybenzamide,
4-amino-5-chloro-N-[[1-[3-(4-fluorophenyl)-3-hydroxypropyl]piperidin-4-yl]-methyl]-2-methoxybenzamide,
4-amino-5-chloro-N-[[1-[3-(4-chlorophenyl)-3-hydroxypropyl]piperidin-4-yl]-methyl]-2-methoxybenzamide,
4-amino-5-chloro-N-[[1-[3-hydroxy-3-(4-methylphenyl) propyl]piperidin-4-yl]-methyl]-2-methoxybenzamide,
4-amino-5-chloro-N-[[1-[3-hydroxy-3-(4-methoxyphenyl) propyl]piperidin-4-yl]-methyl]-2-methoxybenzamide,
4-amino-5-chloro-N-[[1-[3-(2-chlorophenyl)-3-hydroxypropyl]piperidin-4-yl]-methyl]-2-methoxybenzamide,
4-amino-5-chloro-N-[[1-[3-(3-chlorophenyl)-3-hydroxypropyl]piperidin-4-yl]-methyl]-2-methoxybenzamide,
4-amino-5-chloro-N-[[1-[3-(2-fluorophenyl)-3-hydroxypropyl]piperidin-4-yl]-methyl]-2-methoxybenzamide,
4-amino-5-chloro-N-[[1-[3-(3-fluorophenyl)-3-hydroxypropyl]piperidin-4-yl]-methyl]-2-methoxybenzamide,
4-amino-5-chloro-N-[[1-[3-(2,3-dichlorophenyl)-3-hydroxypropyl]piperidin-4-yl]methyl]-2-methoxybenzamide,
4-amino-5-chloro-N-[[1-[3-(2,4-dichlorophenyl)-3-hydroxypropyl]piperidin-4-yl]methyl]-2-methoxybenzamide,
4-amino-5-chloro-N-[[1-[3-(3,4-dichlorophenyl)-3-hydroxypropyl]piperidin-4-yl]methyl]-2-methoxybenzamide,
4-amino-5-chloro-N-[[1-[3-(4-isopropylphenyl)-3-hydroxypropyl]piperidin-4-yl]methyl]-2-methoxybenzamide,
4-amino-5-chloro-N-[[1-[3-(3-methoxyphenyl)-3-hydroxypropyl]piperidin-4-yl-]methyl]-2-methoxybenzamide,
4-amino-5-chloro-N-[[1-(3-hydroxy-3-thiophen-2-ylpropyl)piperidin-4-yl]methyl]-2-methoxybenzamide,
4-amino-5-chloro-N-[[1-[4-(4-fluorophenyl)-3-hydroxybutyl]piperidin-4-yl]methyl]-2-methoxybenzamide,
4-amino-5-chloro-N-[[1-[5-(4-fluorophenyl)-3-hydroxypentyl]piperidin-4-yl]-methyl]-2-methoxybenzamide,
(S)-4-amino-5-chloro-N-[[1-[3-(4-fluorophenyl)-3-hydroxypropyl]piperidin-4-yl]methyl]-2-methoxybenzamide,
(R)-4-amino-5-chloro-N-[[1-[3-(4-fluorophenyl)-3-hydroxypropyl]piperidin-4-yl]methyl]-2-methoxybenzamide,
4-amino-5-chloro-N-[[1-(2-hydroxy-3-phenoxypropyl) piperidin-4-yl]methyl]-2-methoxybenzamide,
4-amino-5-chloro-N-[[1-[3-(4-fluorophenoxy)-2-hydroxypropyl]piperidin-4-yl]methyl]-2-methoxybenzamide,
4-amino-5-chloro-N-[[1-[3-(4-chlorophenoxy)-2-hydroxypropyl]piperidin-4-yl]methyl]-2-methoxybenzamide,
4-amino-5-chloro-N-[[1-[2-hydroxy-3-(4-methoxyphenoxy) propyl]piperidin-4-yl]methyl]-2-methoxybenzamide,
4-amino-5-chloro-N-[[1-[3-(2,3-dichlorophenoxy)-2-hydroxypropyl]piperidin-4-yl]methyl]-2-methoxybenzamide,
4-amino-5-chloro-N-[[1-[3-(2,4-dichlorophenoxy)-2-hydroxypropyl]piperidin-4-yl]methyl]-2-methoxybenzamide,
4-amino-5-chloro-N-[[1-[3-(2,5-dichlorophenoxy)-2-hydroxypropyl]piperidin-4-yl]methyl]-2-methoxybenzamide,
4-amino-5-chloro-N-[[1-[3-(2,6-dichlorophenoxy)-2-hydroxypropyl]piperidin-4-yl]methyl]-2-methoxybenzamide,
4-amino-5-chloro-N-[[1-[3-(3,4-dichlorophenoxy)-2-hydroxypropyl]piperidin-4-yl]methyl]-2-methoxybenzamide,
4-amino-5-chloro-N-[[1-[3-(2-chlorophenoxy)-2-hydroxypropyl]piperidin-4-yl]methyl]-2-methoxybenzamide,
4-amino-5-chloro-N-[[1-[3-(4-methylphenoxy)-2-hydroxypropyl]piperidin-4-yl-]methyl]-2-methoxybenzamide, 4-amino-5-chloro-N-[[1-[3-(3,4-difluorophenoxy)-2-hydroxypropyl]piperidin-4-yl]methyl]-2-methoxybenzamide, 4-amino-5-chloro-N-[[1-[2-hydroxy-3-[4-(trifluoromethyl)phenoxy]propyl]piperidin-4-yl]methyl]-2-methoxybenzamide, 4-amino-5-chloro-N-[[1-[2-hydroxy-3-(4-phenylphenoxy)propyl]piperidin-4-yl]methyl]-2-methoxybenzamide, 4-amino-5-chloro-N-[[1-(2-hydroxy-3-naphthalen-2-yloxypropyl)piperidin-4-yl]methyl]-2-methoxybenzamide, and 4-amino-5-chloro-N-[[1-(2-hydroxy-3-phenylpropyl)piperidin-1-ium-4-yl]methyl]-2-methoxybenzamide.

8. The compound of claim 3, wherein the compound is selected from the group consisting of:

4-amino-5-chloro-N-[[1-(2-hydroxy-2-phenylethyl)piperidin-4-yl]methyl]-2-methoxybenzamide, 4-amino-5-chloro-N-[[1-(3-hydroxy-3-phenylpropyl)piperidin-4-yl]methyl]-2-methoxybenzamide, and 4-amino-5-chloro-N-[[1-[3-(4-chlorophenyl)-3-hydroxypropyl]piperidin-4-yl]-methyl]-2-methoxybenzamide.

9. The compound of claim 1, wherein X is —OCONR$_1$R$_2$, and R$_1$ and R$_2$, together with a nitrogen atom to which they are attached, form five- to seven-membered heterocyclyl.

10. The compound of claim 9, wherein the compound is selected from the group consisting of:

[1-[4-[[(4-amino-5-chloro-2-methoxybenzoyl)amino]methyl]piperidin-1-yl]-3-phenoxypropan-2-yl]piperidine-1-carboxylate,

[1-[4-[[(4-amino-5-chloro-2-methoxybenzoyl)amino]methyl]piperidin-1-yl]-3-(4-fluorophenoxy)propan-2-yl] 3,5-dimethylpiperidine-1-carboxylate,

[1-[4-[[(4-amino-5-chloro-2-methoxybenzoyl)amino]methyl]piperidin-1-yl]-3-(4-chlorophenoxy)propan-2-yl] 3,5-dimethylpiperidine-1-carboxylate,

[1-[4-[[(4-amino-5-chloro-2-methoxybenzoyl)amino]methyl]piperidin-1-yl]-3-(2,3-dichlorophenoxy)propan-2-yl]pyrrolidine-1-carboxylate,

[1-[4-[[(4-amino-5-chloro-2-methoxybenzoyl)amino]methyl]piperidin-1-yl]-3-(2,3-dichlorophenoxy)propan-2-yl]piperidine-1-carboxylate, and

[1-[4-[[(4-amino-5-chloro-2-methoxybenzoyl)amino]methyl]piperidin-1-yl]-3-(2,3-dichlorophenoxy)propan-2-yl]azepane-1-carboxylate.

11. The compound of claim 1, wherein X is —O(CO)NH$_2$.

12. The compound of claim 11, wherein m is 2, and n is 0.

13. The compound of claim 11, wherein B is phenyl substituted with one or more groups independently selected from —H, halo, nitro, cyano, —SO$_2$CH$_3$, trifluoromethyl, trifluoromethoxy, difluoromethoxy, phenyl, C$_1$-C$_6$ linear or branched alkyl, and C$_1$-C$_6$ linear or branched alkoxy.

14. The compound of claim 11, wherein B is phenyl substituted with one or more halo.

15. The compound of claim 11, wherein the compound is selected from the group consisting of:

[2-[4-[[(4-amino-5-chloro-2-methoxybenzoyl)amino]methyl]piperidin-1-yl]-1-phenylethyl]carbamate,

[2-[4-[[(4-amino-5-chloro-2-methoxybenzoyl)amino]methyl]piperidin-1-yl]-1-(4-fluorophenyl)ethyl]carbamate,

[2-[4-[[(4-amino-5-chloro-2-methoxybenzoyl)amino]methyl]piperidin-1-yl]-1-(4-methylphenyl)ethyl]carbamate,

[2-[4-[[(4-amino-5-chloro-2-methoxybenzoyl)amino]methyl]piperidin-1-yl]-1-(4-cyanophenyl)ethyl]carbamate,

[2-[4-[[(4-amino-5-chloro-2-methoxybenzoyl)amino]methyl]piperidin-1-yl]-1-(4-phenylphenyl)ethyl]carbamate,

[2-[4-[[(4-amino-5-chloro-2-methoxybenzoyl)amino]methyl]piperidin-1-yl]-1-(3-methoxyphenyl)ethyl]carbamate,

[2-[4-[[(4-amino-5-chloro-2-methoxybenzoyl)amino]methyl]piperidin-1-yl]-1-(3,4-dichlorophenyl)ethyl]carbamate,

[2-[4-[[(4-amino-5-chloro-2-methoxybenzoyl)amino]methyl]piperidin-1-yl]-1-(2-chlorophenyl)ethyl]carbamate,

[2-[4-[[(4-amino-5-chloro-2-methoxybenzoyl)amino]methyl]piperidin-1-yl]-1-(2,4-dimethylphenyl)ethyl]carbamate,

[2-[4-[[(4-amino-5-chloro-2-methoxybenzoyl)amino]methyl]piperidin-1-yl]-1-(2,5-dimethoxy phenyl)ethyl]carbamate,

[2-[4-[[(4-amino-5-chloro-2-methoxybenzoyl)amino]methyl]piperidin-1-yl]-1-[4-(difluoromethoxy)phenyl]ethyl]carbamate,

[2-[4-[[(4-amino-5-chloro-2-methoxybenzoyl)amino]methyl]piperidin-1-yl]-1-(3,4-difluorophenyl)ethyl]carbamate,

[2-[4-[[(4-amino-5-chloro-2-methoxybenzoyl)amino]methyl]piperidin-1-yl]-1-[4-(trifluoromethyl)phenyl]ethyl]carbamate,

[2-[4-[[(4-amino-5-chloro-2-methoxybenzoyl)amino]methyl]piperidin-1-yl]-1-(2,4-dichlorophenyl)ethyl]carbamate,

[3-[4-[[(4-amino-5-chloro-2-methoxybenzoyl)amino]methyl]piperidin-1-yl]-1-phenylpropyl]carbamate,

[3-[4-[[(4-amino-5-chloro-2-methoxybenzoyl)amino]methyl]piperidin-1-yl]-1-(4-fluorophenyl)propyl]carbamate,

[3-[4-[[(4-amino-5-chloro-2-methoxybenzoyl)amino]methyl]piperidin-1-yl]-1-(4-chlorophenyl)propyl]carbamate,

[3-[4-[[(4-amino-5-chloro-2-methoxybenzoyl)amino]methyl]piperidin-1-yl]-1-(2-chlorophenyl)propyl]carbamate,

[3-[4-[[(4-amino-5-chloro-2-methoxybenzoyl)amino]methyl]piperidin-1-yl]-1-(2-fluorophenyl)propyl]carbamate,

[3-[4-[[(4-amino-5-chloro-2-methoxybenzoyl)amino]methyl]piperidin-1-yl]-1-(3-fluorophenyl)propyl]carbamate,

[3-[4-[[(4-amino-5-chloro-2-methoxybenzoyl)amino]methyl]piperidin-1-yl]-1-(2,3-dichlorophenyl)propyl]carbamate,

[3-[4-[[(4-amino-5-chloro-2-methoxybenzoyl)amino]methyl]piperidin-1-yl]-1-(2,4-dichlorophenyl)propyl]carbamate,

[3-[4-[[(4-amino-5-chloro-2-methoxybenzoyl)amino]methyl]piperidin-1-yl]-1-(3,4-dichlorophenyl)propyl]carbamate,

[3-[4-[[(4-amino-5-chloro-2-methoxybenzoyl)amino]methyl]piperidin-1-yl]-1-(4-isopropylphenyl)propyl]carbamate,

[3-[4-[[(4-amino-5-chloro-2-methoxybenzoyl)amino]methyl]piperidin-1-yl]-1-(3-methoxyphenyl)propyl]carbamate,

[3-[4-[[(4-amino-5-chloro-2-methoxybenzoyl)amino]methyl]piperidin-1-yl]-1-thiophen-2-ylpropyl]carbamate,

[4-[4-[[(4-amino-5-chloro-2-methoxybenzoyl)amino]methyl]piperidin-1-yl]-1-(4-fluorophenyl)butan-2-yl]carbamate,
[1-[4-[[(4-amino-5-chloro-2-methoxybenzoyl)amino]methyl]piperidin-1-yl]-5-(4-fluorophenyl)pentan-3-yl] carbamate,
(S)-3-[4-[[(4-amino-5-chloro-2-methoxybenzoyl)amino]methyl]piperidin-1-yl]-1-(4-fluorophenyl)propyl carbamate,
(R)-[3-[4-[[(4-amino-5-chloro-2-methoxybenzoyl)amino]methyl]piperidin-1-yl]-1-(4-fluorophenyl)propyl]carbamate,
[1-[4-[[(4-amino-5-chloro-2-methoxybenzoyl)amino]methyl]piperidin-1-yl]-3-phenoxypropan-2-yl]carbamate,
[1-[4-[[(4-amino-5-chloro-2-methoxybenzoyl)amino]methyl]piperidin-1-yl]-3-(4-methoxyphenoxy)propan-2-yl]carbamate,
[1-[4-[[(4-amino-5-chloro-2-methoxybenzoyl)amino]methyl]piperidin-1-yl]-3-(2,3-dichlorophenoxy)propan-2-yl]carbamate,
[1-[4-[[(4-amino-5-chloro-2-methoxybenzoyl)amino]methyl]piperidin-1-yl]-3-(2,4-dichlorophenoxy)propan-2-yl]carbamate,
[1-[4-[[(4-amino-5-chloro-2-methoxybenzoyl)amino]methyl]piperidin-1-yl]-3-(2,5-dichlorophenoxy)propan-2-yl]carbamate,
[1-[4-[[(4-amino-5-chloro-2-methoxybenzoyl)amino]methyl]piperidin-1-yl]-3-(2,6-dichlorophenoxy)propan-2-yl]carbamate,
[1-[4-[[(4-amino-5-chloro-2-methoxybenzoyl)amino]methyl]piperidin-1-yl]-3-(3,4-dichlorophenoxy)propan-2-yl]carbamate,
[1-[4-[[(4-amino-5-chloro-2-methoxybenzoyl)amino]methyl]piperidin-1-yl]-3-[4-(trifluoromethyl)phenoxy]propan-2-yl]carbamate,
[1-[4-[[(4-amino-5-chloro-2-methoxybenzoyl)amino]methyl]piperidin-1-yl]-3-(4-phenylphenoxy)propan-2-yl]carbamate,
[1-[4-[[(4-amino-5-chloro-2-methoxybenzoyl)amino]methyl]piperidin-1-yl]-3-naphthalen-2-yloxypropan-2-yl]carbamate, and
[1-[4-[[(4-amino-5-chloro-2-methoxybenzoyl)amino]methyl]piperidin-1-yl]-3-phenylpropan-2-yl]carbamate.

16. The compound of claim 11, wherein the compound is selected from the group consisting of:
[2-[4-[[(4-amino-5-chloro-2-methoxybenzoyl)amino]methyl]piperidin-1-yl]-1-(4-fluorophenyl)ethyl]carbamate,
[2-[4-[[(4-amino-5-chloro-2-methoxybenzoyl)amino]methyl]piperidin-1-yl]-1-(3,4-dichlorophenyl)ethyl]carbamate,
[2-[4-[[(4-amino-5-chloro-2-methoxybenzoyl)amino]methyl]piperidin-1-yl]-1-(2-chlorophenyl)ethyl]carbamate,
[2-[4-[[(4-amino-5-chloro-2-methoxybenzoyl)amino]methyl]piperidin-1-yl]-1-(3,4-difluorophenyl)ethyl]carbamate,
[2-[4-[[(4-amino-5-chloro-2-methoxybenzoyl)amino]methyl]piperidin-1-yl]-1-(2,4-dichlorophenyl)ethyl]carbamate,
[3-[4-[[(4-amino-5-chloro-2-methoxybenzoyl)amino]methyl]piperidin-1-yl]-1-(4-fluorophenyl)propyl]carbamate,
[3-[4-[[(4-amino-5-chloro-2-methoxybenzoyl)amino]methyl]piperidin-1-yl]-1-(4-chlorophenyl)propyl]carbamate,
[3-[4-[[(4-amino-5-chloro-2-methoxybenzoyl)amino]methyl]piperidin-1-yl]-1-(2-chlorophenyl)propyl]carbamate,
[3-[4-[[(4-amino-5-chloro-2-methoxybenzoyl)amino]methyl]piperidin-1-yl]-1-(2-fluorophenyl)propyl]carbamate,
[3-[4-[[(4-amino-5-chloro-2-methoxybenzoyl)amino]methyl]piperidin-1-yl]-1-(3-fluorophenyl)propyl]carbamate,
[3-[4-[[(4-amino-5-chloro-2-methoxybenzoyl)amino]methyl]piperidin-1-yl]-1-(2,3-dichlorophenyl)propyl]carbamate,
[3-[4-[[(4-amino-5-chloro-2-methoxybenzoyl)amino]methyl]piperidin-1-yl]-1-(2,4-dichlorophenyl)propyl]carbamate,
[3-[4-[[(4-amino-5-chloro-2-methoxybenzoyl)amino]methyl]piperidin-1-yl]-1-(3,4-dichlorophenyl)propyl]carbamate,
(S)-3-[4-[[(4-amino-5-chloro-2-methoxybenzoyl)amino]methyl]piperidin-1-yl]-1-(4-fluorophenyl)propyl carbamate, and
(R)-[3-[4-[[(4-amino-5-chloro-2-methoxybenzoyl)amino]methyl]piperidin-1-yl]-1-(4-fluorophenyl)propyl]carbamate.

17. The compound of claim 11, wherein the compound is selected from the group consisting of:
[2-[4-[[(4-amino-5-chloro-2-methoxybenzoyl)amino]methyl]piperidin-1-yl]-1-(3-methoxyphenyl)ethyl]carbamate,
3-[4-[[(4-amino-5-chloro-2-methoxybenzoyl)amino]methyl]piperidin-1-yl]-1-(4-fluorophenyl)propyl carbamate,
(S)-3-[4-[[(4-amino-5-chloro-2-methoxybenzoyl)amino]methyl]piperidin-1-yl]-1-(4-fluorophenyl)propyl carbamate,
(R)-[3-[4-[[(4-amino-5-chloro-2-methoxybenzoyl)amino]methyl]piperidin-1-yl]-1-(4-fluorophenyl)propyl]carbamate, and
[1-[4-[[(4-amino-5-chloro-2-methoxybenzoyl)amino]methyl]piperidin-1-yl]-3-phenylpropan-2-yl]carbamate.

18. The compound of claim 1, wherein the compound is selected from the group consisting of:
4-amino-5-chloro-N-[[1-(2-hydroxy-2-phenylethyl)piperidin-4-yl]methyl]-2-methoxybenzamide,
[2-[4-[[(4-amino-5-chloro-2-methoxybenzoyl)amino]methyl]piperidin-1-yl]-1-(3-methoxyphenyl)ethyl]carbamate,
4-amino-5-chloro-N-[[1-(3-hydroxy-3-phenylpropyl)piperidin-4-yl]methyl]-2-methoxybenzamide,
4-amino-5-chloro-N-[[1-[3-(4-chlorophenyl)-3-hydroxypropyl]piperidin-4-yl]-methyl]-2-methoxybenzamide,
3-[4-[[(4-amino-5-chloro-2-methoxybenzoyl)amino]methyl]piperidin-1-yl]-1-(4-fluorophenyl)propyl carbamate,
(S)-3-[4-[[(4-amino-5-chloro-2-methoxybenzoyl)amino]methyl]piperidin-1-yl]-1-(4-fluorophenyl)propyl carbamate,
(R)-[3-[4-[[(4-amino-5-chloro-2-methoxybenzoyl)amino]methyl]piperidin-1-yl]-1-(4-fluorophenyl)propyl]carbamate, and
[1-[4-[[(4-amino-5-chloro-2-methoxybenzoyl)amino]methyl]piperidin-1-yl]-3-phenylpropan-2-yl]carbamate.

19. A pharmaceutical compound comprising a therapeutically effective amount of a compound of claim 1 or a pharmaceutically acceptable salt thereof and a pharmaceutically acceptable carrier.

20. The composition of claim 19, wherein the compound is selected from the group consisting of:
- 4-amino-5-chloro-N-[[1-(2-hydroxy-2-phenylethyl)piperidin-4-yl]methyl]-2-methoxybenzamide,
- [2-[4-[[(4-amino-5-chloro-2-methoxybenzoyl)amino]methyl]piperidin-1-yl]-1-(3-methoxyphenyl)ethyl]carbamate,
- 4-amino-5-chloro-N-[[1-(3-hydroxy-3-phenylpropyl)piperidin-4-yl]methyl]-2-methoxybenzamide,
- 4-amino-5-chloro-N-[[1-[3-(4-chlorophenyl)-3-hydroxypropyl]piperidin-4-yl]-methyl]-2-methoxybenzamide,
- 3-[4-[[(4-amino-5-chloro-2-methoxybenzoyl)amino]methyl]piperidin-1-yl]-1-(4-fluorophenyl)propyl carbamate,
- (S)-3-[4-[[(4-amino-5-chloro-2-methoxybenzoyl)amino]methyl]piperidin-1-yl]-1-(4-fluorophenyl)propyl carbamate,
- (R)-[3-[4-[[(4-amino-5-chloro-2-methoxybenzoyl)amino]methyl]piperidin-1-yl]-1-(4-fluorophenyl)propyl]carbamate, and
- [1-[4-[[(4-amino-5-chloro-2-methoxybenzoyl)amino]methyl]piperidin-1-yl]-3-phenylpropan-2-yl]carbamate.

* * * * *